(12) United States Patent
Cheney et al.

(10) Patent No.: US 11,523,820 B2
(45) Date of Patent: Dec. 13, 2022

(54) SHAPE MEMORY IMPLANTS AND A METHOD AND APPARATUS FOR THE LOADING AND IMPLANTING THEREOF

(71) Applicant: DEPUY SYNTHES PRODUCTS, INC., Raynham, MA (US)

(72) Inventors: Daniel F. Cheney, Downingtown, PA (US); Luke A. Perkins, San Antonio, TX (US); Joseph P. Ritz, Castroville, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 316 days.

(21) Appl. No.: 16/775,680

(22) Filed: Jan. 29, 2020

(65) Prior Publication Data

US 2021/0228206 A1 Jul. 29, 2021

(51) Int. Cl.
*A61B 17/064* (2006.01)
*A61B 17/068* (2006.01)
(Continued)

(52) U.S. Cl.
CPC ...... *A61B 17/0642* (2013.01); *A61B 17/0684* (2013.01); *A61B 17/0644* (2013.01);
(Continued)

(58) Field of Classification Search
CPC . A61B 17/10; A61B 17/0642; A61B 17/0684; A61B 17/0682; A61B 17/068; A61B 17/072; A61B 17/115; A61B 17/0644; A61B 17/07207; A61B 17/105; A61B 2017/00367; A61B 2017/0641;
(Continued)

(56) References Cited

U.S. PATENT DOCUMENTS 1,106,241 A 8/1914 Richardson
2,544,492 A 3/1947 Downing
(Continued)

FOREIGN PATENT DOCUMENTS

EP 0682920 B1 2/1995
EP 0857462 A1 1/1998
(Continued)

OTHER PUBLICATIONS

4-Fusion Shape Memory Implant Training Slide Images, MEMOMETAL, Inc., 2008.
(Continued)

*Primary Examiner* — Marcela I. Shirsat
(74) *Attorney, Agent, or Firm* — Christopher L. Makay

(57) ABSTRACT

An orthopedic fixation system includes an implant and an implant insertion device. The implant transitions between a natural shape and an insertion shape. The implant includes a bridge defining a slot with a first end and a second end and first and second anchoring members extending from the bridge. The implant insertion device moves between a loaded position and an unloaded position. The implant insertion device in its loaded position inserts through the slot of the bridge and engages the bridge at the first and second ends of the slot such that the implant insertion device constrains the implant in its insertion shape. The implant insertion device in its unloaded position releases the implant.

16 Claims, 47 Drawing Sheets

(51) Int. Cl.
*A61B 17/00* (2006.01)
*A61B 17/115* (2006.01)

(52) U.S. Cl.
CPC ......... *A61B 17/0682* (2013.01); *A61B 17/115* (2013.01); *A61B 2017/00867* (2013.01); *A61B 2017/0641* (2013.01); *A61B 2017/0645* (2013.01)

(58) Field of Classification Search
CPC .. A61B 2017/0645; A61B 2017/07214; A61B 50/20; A61B 2017/00867
USPC ............ 606/74–75; 227/175.1, 177.1, 178.1, 227/179.1, 901, 902
See application file for complete search history.

(56) References Cited

U.S. PATENT DOCUMENTS

| | | | |
|---|---|---|---|
| 3,939,828 | A | 2/1976 | Mohr et al. |
| 3,960,147 | A | 6/1976 | Murray |
| 4,269,180 | A | 5/1981 | Dall et al. |
| 4,438,769 | A | 3/1984 | Pratt et al. |
| 4,485,816 | A | 12/1984 | Krumme |
| 4,526,174 | A | 7/1985 | Froehlich |
| 4,570,623 | A | 2/1986 | Ellison et al. |
| 4,592,346 | A | 6/1986 | Jurgutis |
| 4,608,972 | A | 9/1986 | Small |
| 4,665,906 | A | 5/1987 | Jervis |
| 4,713,077 | A | 12/1987 | Small |
| 4,869,243 | A | 9/1989 | Huene |
| 5,067,957 | A | 11/1991 | Jervis |
| 5,112,336 | A | 5/1992 | Krevolin et al. |
| 5,163,557 | A | 11/1992 | Sokolowski |
| 5,171,252 | A | 12/1992 | Friedland |
| 5,246,443 | A | 9/1993 | Mai |
| 5,357,732 | A | 10/1994 | Markle et al. |
| 5,425,489 | A | 6/1995 | Shichman et al. |
| 5,474,557 | A | 12/1995 | Mai |
| 5,478,354 | A | 12/1995 | Tovey et al. |
| 5,769,856 | A | 6/1998 | Dong et al. |
| 5,779,707 | A | 7/1998 | Bertholet et al. |
| 5,785,713 | A | 7/1998 | Jobe |
| 5,976,159 | A | 11/1999 | Bolduc et al. |
| 6,001,110 | A | 12/1999 | Adams |
| 6,187,009 | B1 | 2/2001 | Herzog et al. |
| 6,268,589 | B1 | 7/2001 | Flot |
| 6,323,461 | B2 | 11/2001 | Flot |
| 6,412,639 | B1 | 7/2002 | Hickey |
| 6,607,542 | B1 | 8/2003 | Wild |
| 6,685,708 | B2 | 2/2004 | Monassevitch et al. |
| 6,767,356 | B2 * | 7/2004 | Kanner ................ A61B 17/068 606/220 |
| 6,783,531 | B2 | 8/2004 | Allen |
| 6,827,723 | B2 | 12/2004 | Carson |
| 7,240,677 | B2 | 7/2007 | Fox |
| 7,344,539 | B2 | 3/2008 | Serhan et al. |
| 7,428,807 | B2 | 9/2008 | Vander Bush et al. |
| 7,556,647 | B2 | 7/2009 | Drews et al. |
| 7,678,115 | B2 | 3/2010 | D'Alessio et al. |
| 7,867,265 | B2 | 1/2011 | Beutter |
| 8,057,490 | B2 | 11/2011 | Harris |
| 8,114,138 | B2 | 2/2012 | Nehls |
| 8,118,952 | B2 | 2/2012 | Gall et al. |
| 8,137,351 | B2 | 3/2012 | Prandi |
| 8,191,220 | B2 | 6/2012 | Magnuson et al. |
| 8,211,109 | B2 | 7/2012 | Groiso |
| D669,984 | S | 10/2012 | Cheney et al. |
| D669,985 | S | 10/2012 | Cheney et al. |
| D676,962 | S | 2/2013 | Cheney et al. |
| 8,584,853 | B2 | 11/2013 | Knight et al. |
| 8,596,514 | B2 | 12/2013 | Miller et al. |
| 9,585,656 | B2 | 3/2017 | Taber et al. |
| 9,855,036 | B2 | 1/2018 | Palmer et al. |
| 9,931,115 | B2 | 4/2018 | Morgan et al. |
| 10,080,599 | B2 | 9/2018 | Caldarella et al. |
| 2004/0097970 | A1 | 5/2004 | Hughett |
| 2005/0009660 | A1 | 1/2005 | Allen |
| 2005/0033430 | A1 | 2/2005 | Powers et al. |
| 2005/0043757 | A1 | 2/2005 | Arad et al. |
| 2005/0080454 | A1 | 4/2005 | Drews et al. |
| 2005/0107807 | A1 | 5/2005 | Nakao |
| 2005/0113832 | A1 | 5/2005 | Molz et al. |
| 2005/0143749 | A1 | 6/2005 | Zalenski et al. |
| 2006/0106388 | A1 | 5/2006 | Lococo |
| 2006/0229627 | A1 | 10/2006 | Hunt et al. |
| 2007/0118141 | A1 | 5/2007 | Marchyn et al. |
| 2007/0118224 | A1 | 5/2007 | Shah et al. |
| 2008/0065153 | A1 | 3/2008 | Allard et al. |
| 2008/0110957 | A1 | 5/2008 | McBride et al. |
| 2008/0319443 | A1 | 12/2008 | Focht et al. |
| 2009/0062800 | A1 | 3/2009 | Shano |
| 2009/0062806 | A1 | 3/2009 | Scott et al. |
| 2009/0216285 | A1 | 8/2009 | Ek et al. |
| 2009/0272786 | A1 | 11/2009 | Zeiner et al. |
| 2010/0133316 | A1 | 6/2010 | Lizee et al. |
| 2010/0191258 | A1 | 7/2010 | Harris et al. |
| 2010/0217270 | A1 | 8/2010 | Polinski et al. |
| 2011/0093018 | A1 | 4/2011 | Prasad et al. |
| 2011/0186456 | A1 | 8/2011 | Bertazzoni et al. |
| 2011/0270327 | A1 | 11/2011 | Blakemore et al. |
| 2012/0024937 | A1 | 2/2012 | Allen |
| 2012/0085809 | A1 | 4/2012 | Milo |
| 2012/0209305 | A1 | 8/2012 | Deodhar et al. |
| 2012/0209401 | A1 | 8/2012 | Euteneuer et al. |
| 2012/0228355 | A1 | 9/2012 | Combrowski et al. |
| 2012/0259419 | A1 | 10/2012 | Brown et al. |
| 2013/0026206 | A1 | 1/2013 | Fox |
| 2013/0026207 | A1 | 1/2013 | Fox |
| 2013/0030437 | A1 | 1/2013 | Fox |
| 2013/0030438 | A1 | 1/2013 | Fox |
| 2013/0184476 | A1 | 7/2013 | McIff et al. |
| 2013/0231667 | A1 | 9/2013 | Taylor et al. |
| 2014/0018809 | A1 | 1/2014 | Allen |
| 2014/0097228 | A1 | 4/2014 | Taylor et al. |
| 2014/0175157 | A1 | 6/2014 | Vold et al. |
| 2014/0276830 | A1 | 9/2014 | Cheney |
| 2014/0277516 | A1 | 9/2014 | Miller et al. |
| 2015/0230843 | A1 | 8/2015 | Palmer et al. |
| 2015/0257801 | A1 | 9/2015 | Palmer et al. |
| 2016/0015384 | A1 | 1/2016 | Roedl et al. |
| 2016/0066907 | A1 | 3/2016 | Cheney et al. |
| 2016/0074037 | A1 | 3/2016 | Cheney et al. |
| 2016/0235460 | A1 | 8/2016 | Wahl |
| 2017/0000482 | A1 | 1/2017 | Averous et al. |
| 2017/0065275 | A1 | 3/2017 | Cheney |
| 2017/0209193 | A1 * | 7/2017 | Hartdegen ......... A61B 17/8863 |
| 2017/0252036 | A1 | 9/2017 | Palmer et al. |
| 2017/0281157 | A1 | 10/2017 | Hartdegen et al. |
| 2019/0117219 | A1 | 4/2019 | Ritz et al. |
| 2019/0192140 | A1 | 6/2019 | Ducharme et al. |

FOREIGN PATENT DOCUMENTS

| | | |
|---|---|---|
| EP | 0826340 A2 | 3/1998 |
| EP | 1870042 A1 | 12/2007 |
| EP | 3187134 A1 | 7/2017 |
| EP | 3260053 B1 | 2/2019 |
| FR | 2874166 A1 | 2/2006 |
| WO | 1992017122 A2 | 10/1992 |
| WO | 2008129061 A1 | 10/2008 |
| WO | 2013055824 A1 | 4/2013 |
| WO | 2015131106 A1 | 9/2015 |
| WO | 2015179552 A1 | 11/2015 |
| WO | 2015179652 A1 | 11/2015 |
| WO | 2016007624 A1 | 1/2016 |

OTHER PUBLICATIONS

4-Fusion Shape Memory Implant Brochure, Memometal, Inc., Jun. 23, 2009.

MemoGraph Brochure, M.B.A. (Memory Biological Application), Parc Club de Nancy de Brabois,Batiment B11, 4 allee Vincennes, 54500 Vandceurve, France, 1999.

(56) References Cited

OTHER PUBLICATIONS

OSStaple Brochure Including pictures of staple loaded in shipping block, BioMedical Enterprises, Inc., 14875 Omicron Drive, Suite 205, San Antonio, TX 78245, 2010.
E. A. Van Amerongen et al., "Four-Corner Arthrodesis Using the Quad Memory Staple," Journal of Hand Surgery (European vol. 2008) (Jan. 7, 2009).
U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.
T. F. Smith, "The Bone Staple: Tried and True Superhero of Bone Fixation," Educational Materials Update Chapter 41 (2010) available at www.podiatryinstitute.com/pdfs/Update 2010/2010 41.pdf.
ELEVEST Procedure Kit, Instructions for Use by CooperSurgical (© 2007).
Agee WristJack, Surgeon's Manual by Hand BioMechanics Labs, Inc. (© 1990-2002).
Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).
Superelastic Fixation System Brochure, MEMOMETAL Inc., USA, Aug. 12, 2009.
Shape Memory Staple System for Arthrodesis and Skeletal Fixation of the Hand Brochure, Core Essence Orhtopaedics, Inc., 2009.
ENTact™ Septal Stapler, Product brochure by ENTrigue Surgical, Inc. (© 2009).
R. M. Sloan et al., "Orthopedic Fixation Devices," RADIOGRAPHICS at 823 (Sep. 1991).
J. Arthur, "Improving Operating Efficiency in Five Days," Lean Six Sigma for Hospitals, McGraw-Hill (2011).
K. Yamauchi et al. (ed.), "Shape Memory and Superelastic Alloys: Applications and Technologies" (2011).
BioResearch Innovations (BRI), "Memodyn Compression Staple," FDA 510(K) disclosure (Jan. 2004).
G. C. Taylor et al., "Complications of Internal Fixation," Podiatry Institute Educational Materials Update Chapter 79 (1992).
Wright Medical Technology, Inc., "Charlotte Compression Staple as described by Robert Anderson, MD; Bruce Cohen, MD; and W. Hodges Davis, MD" (2007).
A. A. Weinbroum et al., "Efficiency of the Operating Room Suite," American Journal of Surgery 244-250 (2003).
G. G. Porto, "Safety by Design: Ten Lessons From Human Factors Research," Journal of Healthcare Risk Management 43-50 (Fall 2011).
Russell, Scott M., Design Considerations for Nitinol Bone Staples, Journals of Materials Engineering and Performance, vol. 18(5-6), Aug. 2009, USA.
International Search Report for PCT/IB2021/050726, dated Apr. 29, 2021, PCT Application Counterpart to U.S. Appl. No. 16/775,680.

* cited by examiner

SHAPE MEMORY IMPLANTS AND A METHOD AND APPARATUS FOR THE LOADING AND IMPLANTING THEREOF

BACKGROUND OF THE INVENTION

1. Field of the Invention

The present invention relates generally to shape memory implants and the implantation thereof using an implantation device and, more particularly, but not way of limitation, to an orthopedic fixation system including a shape memory implant and an implantation device designed for loading with the shape memory implant and for subsequent delivery of the shape memory implant utilizing the implantation device.

2. Description of the Related Art

Shape memory implants are commonly used in surgical procedures that require the reattachment or fusing of tissue or bone. Shape memory implants can be composed of a shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic recovery, and then releases the stored mechanical energy when the constraining instrument is removed. In these types of implants, the implants are mechanically moved into their second shape and maintained in their second shape by instrumentation such that, upon release from the instrumentation, the implants elastically return from their second shape into their first final shape.

In surgical procedures, the elastic property of constrained shape memory implants is used as follows. Bones that require fixating are aligned, and the shape memory implant, which has been mechanically deformed to its second shape, is maintained in instrumentation and inserted across the bones. After insertion, the shape memory implant is released from the instrumentation, whereupon the shape memory implant elastically tries to return to its first final shape such that the shape memory implant maintains the bones fixated together. The shape memory implant because it stores mechanical energy continuously applies force to the fixated bones as the shape memory implant tries to transition from the second shape to the first final shape, which aids in the healing process.

Various types of instrumentation can be used for either maintaining the shape memory implants in their second shape or moving an implant from its first final shape to a temporary second shape. Some companies used metal forceps to open and insert the shape memory implant. These forceps have to be sterilized by a hospital, and then a shape memory implant can be placed on the forceps, opened to a desired position, and used for inserting the implant. Although potentially effective, forceps require the implant to be loaded into the forceps during surgery, which might be cumbersome and time consuming. In addition, forceps might be large which could hinder implantation of the shape memory implant into a patient during surgery. It is also possible that a physician using the forceps might damage the shape memory implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Other instrumentation includes plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the instrumentation allows the shape memory implant to be preloaded prior to surgery. However, using instrumentation that substantially conforms to the profile of the shape memory implant can create several problems for a surgeon. First, this type of instrumentation often makes disengagement of the shape memory staple after implantation problematic. In particular, the shape memory implant sticks to the instrumentation due to the frictional engagement between the shape memory implant, which is trying to compress, and the passage of the instrumentation, resulting in a more difficult surgical procedure and the potential for a less than satisfactory fixation of tissue or bone. Second, this type of instrumentation results in an abrupt and sudden release of stored mechanical energy as the implant is removed from the device. This type of instrumentation accordingly provides no method of slowly transitioning the stored energy in the implant from the instrumentation to the bones being fixated. Finally, this type of instrumentation can result in entanglement during release, in which the implant begins to compress upon release thereby making extraction of this type of instrumentation more difficult.

Another type of plastic and disposable instrument includes arms movable between a disengaged position and an engaged position. The arms terminate in jaws such that, when the arms reside in their engaged position, the jaws contact the shape memory implant to maintain the shape memory implant open for insertion. While the movable arms and jaws release the implant without entanglement and further allow the slow transitioning of the implant, the jaws, due to their location when contacting the shape memory implant as well as their path of travel during removal from the shape memory implant, leave the implant situated above the bone surface such that tamping of the implant to a position flush with the bone surface is required. As a result, the instrument can be impractical for certain surgeries because it is not always possible to tamp and thus seat the implant flush with a bone surface after its release from the instrument, particularly when the implant includes anchoring members of limited length.

Accordingly, an instrument that constrains a shape memory implant in its second shape, allows the shape memory implant to be preloaded and sterilized prior to surgery, controls the rate of tension release, simplifies removal of the shape memory implant after implantation, and releases the shape memory implant at a bone surface thereby eliminating tamping would be beneficial.

SUMMARY OF THE INVENTION

In accordance with the present invention, an orthopedic fixation system includes an implant and an implant insertion device. The implant transitions between a natural shape and an insertion shape. The implant insertion device moves between a loaded position that constrains the implant in its insertion shape and an unloaded position that releases the implant for attempted transition from its insertion shape to its natural shape.

The implant includes a bridge defining a slot with a first end and a second end and first and second anchoring members extending from the bridge. The slot receives the implant insertion device such that the implant insertion device engages the bridge at the first and second ends of the slot thereby constraining the implant in its insertion shape.

The bridge includes a first transition section at a first end thereof and a second transition section at a second end thereof. The first and second transition sections deform to transition the implant between its natural shape and its insertion shape. When the slot of the bridge receives the implant insertion device, the implant insertion device engages the bridge at the first and second transition sections and constrains the implant in its insertion shape. The first anchoring member extends from the first transition section of the bridge and the second anchoring member extends from the second transition section of the bridge. After the slot of the bridge receives the implant insertion device, the implant insertion device engages the first and second anchoring members and constrains the implant in its insertion shape. The bridge in the first embodiment includes a first bridge segment and a second bridge segment that define the slot therebetween.

The bridge alternatively includes a transition section at a center section of the implant. The transition section deforms to transition the implant between its natural shape and its insertion shape. Once the slot of the bridge receives the implant insertion device, the implant insertion device engages the bridge at the first and second ends of the slot and constrains the implant in its insertion shape. The first anchoring member extends from the bridge and the second anchoring member extends from the bridge such that, when the slot of the bridge receives the implant insertion device, the implant insertion device engages the first and second anchoring members and constrains the implant in its insertion shape.

The implant may include third and fourth anchoring members. The third anchoring member resides exterior to the first anchoring member and extends from the bridge at the first end thereof. The fourth anchoring member resides exterior to the second anchoring member and extends from the bridge at the second end thereof. Alternatively, the first anchoring member extends from the bridge at the first end thereof, whereas the second anchoring member extends from the bridge at a second end thereof. The third anchoring member includes a passage and extends from the bridge interior to the first anchoring member. The fourth anchoring member includes a passage and extends from the bridge interior to the second anchoring member. When the slot of the bridge and the passages of the third and fourth anchoring members receive the implant insertion device, the implant insertion device engages the first and second anchoring members and constrains the implant in its insertion shape.

The implant in a further alternative includes the first anchoring member extending from the bridge at the first end thereof offset from the first end of the slot. The second anchoring member resides adjacent the first anchoring member and extends from the bridge at the first end thereof offset from the first end of the slot. The third anchoring member extends from the bridge at a second end thereof adjacent the second end of the slot.

The implant in a still further alternative includes the first anchoring member extending from the bridge at the first end thereof offset from the first end of the slot. The second anchoring member resides adjacent the first anchoring member and extends from the bridge at the first end thereof offset from the first end of the slot. The third anchoring member extends from the bridge at the second end thereof offset from the second end of the slot. The fourth anchoring member resides adjacent the third anchoring member and extends from the bridge at the second end thereof offset from the second end of the slot.

The implant insertion device includes a body with a first end and a second end and an implant grip coupled with the body. The implant grip moves relative to the body between an engaged position and a disengaged position. The implant grip in its engaged position inserts through the slot of the bridge and engages the bridge at the first and second ends of the slot such that the implant grip constrains the implant in its insertion shape. The implant grip in its disengaged position releases the implant for attempted transition from its insertion shape to its natural shape.

The body defines a channel with an exit at the second end of the body. The implant grip includes an actuator and a paddle that inserts into the channel of the body. The actuator connects with the paddle and secures the paddle with the body such that movement of the actuator relative to the body progresses the paddle between an engaged position and a disengaged position. The paddle in its engaged position extends from the channel and inserts through the slot of the bridge to engage the bridge at the first and second ends of the slot and constrain the implant in its insertion shape. The paddle in its disengaged position retracts into the channel to release the implant.

The body defines a stop and a tamp at its second end that abuts the bridge of the implant during loading of the implant insertion device with the implant. When the tamp abuts the bridge, the exit for the channel of the body aligns with the slot of the bridge for the implant such that extension of the paddle from the channel inserts the paddle through the slot of the bridge to engage the bridge at the first and second ends of the slot and constrain the implant in its insertion shape. As the paddle progresses from its disengaged position to its engaged position, the actuator moves along the body towards the stop of the body until the actuator contacts the stop.

The paddle includes a shaft with a first end and a second end and a blade coupled with the shaft at its second end. The blade includes a leading edge between first and second sides. The channel communicates exterior to the body and includes a shaft channel configured to receive the shaft of the paddle therein and a blade channel configured to receive the blade of the paddle therein. Once the paddle inserts into the channel of the body, the shaft at its first end is exposed exterior to the body such that the shaft is engageable with the actuator. Movement of the actuator relative to the body progresses the paddle between its engaged position and its disengaged position. As the paddle progresses to its engaged position, the blade beginning at its leading edge extends from the channel and inserts through the slot of the bridge to engage the bridge with its first and second sides abutting respective first and second ends of the slot thereby constraining the implant in its insertion shape. Conversely, as the paddle progresses to its disengaged position, the blade retracts into the channel to release the implant.

In a method for an orthopedic fixation system, the implant insertion device loads with the implant whereby the implant insertion device inserts through the slot of the bridge and engages the bridge at the first and second ends of the slot such that the implant insertion device constrains the implant in its insertion shape. A surgeon using the implant insertion device positions the implant with its first anchoring member at a first bone, its second anchoring member at a second bone, and its bridge spanning a fusion zone of the first and second bones. The surgeon retracts the implant insertion device from the slot of the bridge while inserting the first anchoring member into the first bone and the second anchoring member into the second bone until the bridge resides adjacent the first and second bones across the fusion zone thereof. The surgeon removes the implant insertion device from the slot of the bridge whereby the implant insertion device releases the bridge at the first and second ends of the slot such that the implant attempts to transition from its insertion shape to its natural shape.

More particularly, the implant grip moves relative to the body whereby the implant grip inserts through the slot of the bridge and engages the bridge at the first and second ends of the slot such that the implant grip constrains the implant in its insertion shape. The surgeon using the body of the implant insertion device positions the implant with its first anchoring member at a first bone, its second anchoring member at a second bone, and its bridge spanning a fusion zone of the first and second bones. The surgeon moves the implant grip relative to the body whereby the implant grip retracts from the slot of the bridge. The surgeon using the body inserts the first anchoring member into the first bone and the second anchoring member into the second bone until the bridge resides adjacent the first and second bones across the fusion zone thereof. The surgeon moves the implant grip relative to the body until the implant grip releases the bridge at the first and second ends of the slot such that the implant attempts to transition from its insertion shape to its natural shape.

Still more particularly, the body is positioned relative to the implant whereby the second end of the body abuts the bridge of the implant and the exit from the channel aligns with the slot of the bridge. The actuator moves relative to the body whereby the paddle extends from the channel and inserts through the slot of the bridge to engage the bridge at the first and second ends of the slot and constrain the implant in its insertion shape. A surgeon using the body of the implant insertion device positions the implant with its first anchoring member at a first bone, its second anchoring member at a second bone, and its bridge spanning a fusion zone of the first and second bones. The surgeon moves the actuator relative to the body whereby the paddle retracts from the slot of the bridge into the channel of the body. The surgeon using the body inserts the first anchoring member into the first bone and the second anchoring member into the second bone until the bridge resides adjacent the first and second bones across the fusion zone thereof. The surgeon moves the actuator relative to the body until the paddle releases the bridge at the first and second ends of the slot such that the implant attempts to transition from its insertion shape to its natural shape. Alternatively, the surgeon using the body inserts the first anchoring member into the first bone and the second anchoring member into the second bone until the paddle contacts the first and second bones. The surgeon pushes on the body whereby the second end of the body via the bridge inserts the first anchoring member into the first bone and the second anchoring member into the second bone further whereby the paddle via its contact with the first and second bones retracts from the slot of the bridge into the channel of the body until the bridge resides adjacent the first and second bones across the fusion zone thereof. The surgeon moves the actuator relative to the body until the paddle releases the bridge at the first and second ends of the slot such that the implant attempts to transition from its insertion shape to its natural shape.

It is therefore an object of the present invention to provide an implant with a slot whereby the implant transitions between a natural shape and an insertion shape.

It is another object of the present invention to provide an implant insertion device that engages the implant at its slot to constrain the implant in its insertion shape.

It is a further object of the present invention to provide the implant insertion device whereby the implant insertion device delivers the implant at a surface of bone, bones, or bone pieces such that tamping of the implant is eliminated.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Figure 1A:
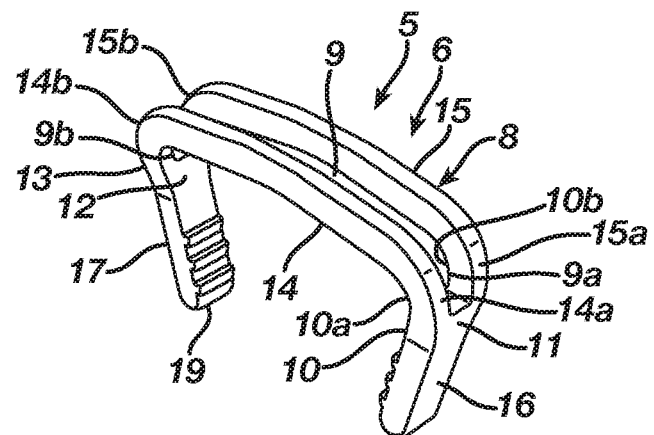
FIG. 1A is an isometric view illustrating a shape memory implant according to a first embodiment in a natural shape.
Figure 1B:
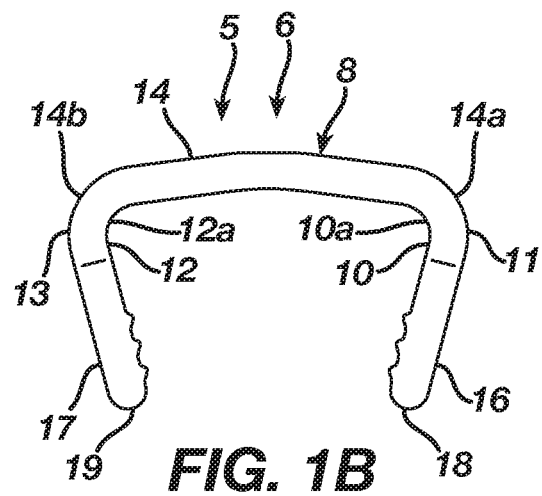
FIG. 1B is a side view thereof.
Figure 1C:
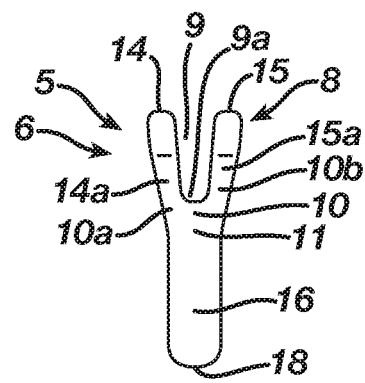
FIG. 1C is an end view thereof.
Figure 1D:
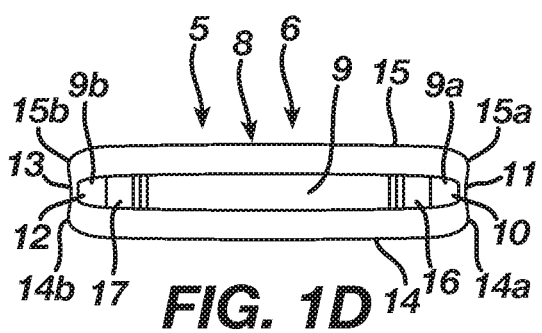
FIG. 1D is a top view thereof.
Figure 1E:
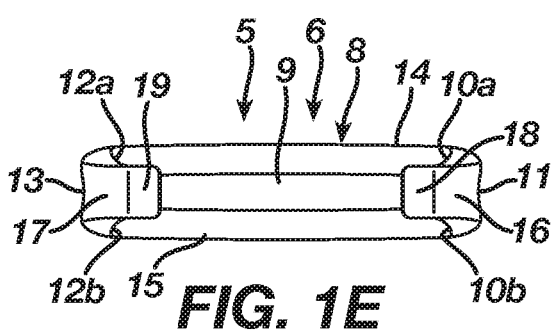
FIG. 1E is a bottom view thereof.

FIGS. 1A-IE illustrate an orthopedic implant 5 according to a first embodiment in a natural shape 6, whereas FIGS. 2A-2E illustrate the orthopedic implant 5 in an insertion shape 7. The implant 5 in the first embodiment may be manufactured from a shape memory material with super-elastic or temperature dependent properties (e.g., Nitinol) such that the implant 5 transitions between its natural shape 6 and its insertion shape 7. The implant 5 when deformed from its natural shape 6 to its insertion shape 7 stores energy deliverable to bone, bones, or bone pieces. In accordance with its manufacture from shape memory material, the implant 5 begins in its natural shape 6, is transitionable to its insertion shape 7, and, once implanted in bone, bones, or bone pieces, attempts to transition from its insertion shape 7 to its natural shape 6 whereby the implant 5 delivers the energy stored therein to the bone, bones, or bone pieces in order to affix the bone, bones, or bone pieces and promote a healing thereof. In the first embodiment, attempted transition of the implant 5 from its insertion shape 7 to its natural shape 6 continuously compresses the bone, bones, or bone pieces to promote fusion thereof.

The implant 5 in the first embodiment includes a bridge 8 defining a slot 9, a transition section 10 at an end 11 of the bridge 8, and a transition section 12 at an end 13 of the bridge 8. The bridge 8 in the first embodiment includes a first bridge segment 14 located substantially parallel with a second bridge segment 15 such that the first and second bridge segments 14 and 15 define the slot 9 therebetween. In the first embodiment, the transition section 10 may incorporate a transition segment 10*a* defined at an end 14*a* of the first bridge segment 14 and a transition segment 10*b* defined at an end 15*a* of the second bridge segment 15. Likewise, the transition section 12 may incorporate a transition segment 12*a* defined at an end 14*b* of the first bridge segment 14 and a transition segment 12*b* defined at an end 15*b* of the second bridge segment 15. The first and second bridge segments 14 and 15 in the first embodiment are substantially identical in size, shape, and length, although one of ordinary skill in the art will recognize that the first and second bridge segments 14 and 15 may be dissimilar in size, shape, and length.

The implant 5 in the first embodiment includes an anchoring member in the form of a leg 16 extending from the transition section 10 of the bridge 8 at its end 11 and an anchoring member in the form of a leg 17 extending from the transition section 12 of the bridge 8 at its end 13. In the first embodiment, the leg 16 is formed integrally with the bridge 8 at the transition section 10, while the leg 17 is formed integrally with the bridge 8 at the transition section 12. More particularly, the leg 16 extends from the transition section 10 below a merge point of the transition segments 10*a* and 10*b* for the transition section 10, whereas the leg 17 extends from the transition section 12 below a merge point of the transition sections 12*a* and 12*b* for the transition section 12. Each leg 16 and 17, which has a respective tip 18 and 19, may include barbs thereon that improve the pull-out resistance of the implant 5. The implant 5 includes anchoring members in the form of legs 16 and 17 in order to facilitate a securing of the implant 5 with bone, bones, or bone pieces whereby the bridge 8 between the legs 16 and 17 traverses a fixation zone of the bone, bones, or bone pieces such that the implant 5, after its insertion and attempted transition from the insertion shape 7 to the natural shape 6, delivers energy to the bone, bones, or bone pieces at the fixation zone.

The regular inherent shape of the implant 5, as illustrated in FIGS. 1A-1E, is its natural shape 6 where the transition sections 10 and 12 locate the bridge 8 in a natural form that places the legs 16 and 17 in a natural position whereby the legs 16 and 17 are convergent and spaced apart at a first distance. Nevertheless, as illustrated in FIGS. 2A-2E, the implant 5 is deformable under the action of superelasticity or temperature dependent shape memory to an insertion shape 7 where the transition sections 10 and 12 deform to store energy while also moving the bridge 8 from its natural form to an insertion form that places the legs 16 and 17 in an insertion position whereby the legs 16 and 17 are substantially parallel and spaced apart at a second distance that is greater than the first distance. Since the insertion shape 7 is not the regular inherent shape of the implant 5, the bridge 8 typically is mechanically constrained using an implant insertion device whereby the implant insertion device maintains the bridge 8 in its insertion form. In order to facilitate engagement of an implant insertion device with the implant 5, the bridge 8 includes the slot 9 that receives the implant insertion device therethrough such that the implant insertion device engages the bridge 8 at each end 9*a* and 9*b* of the slot 9. In particular, the implant insertion device passes through the slot 9 and engages the bridge 8 at its transition sections 10 and 12 thereby constraining the deformed transition sections 10 and 12 to maintain the implant 5 in its insertion shape 7. The implant insertion device of the present invention accordingly passes through the slot 9 after deformation of the transition sections 10 and 12 whereby the implant insertion device is sized to engage the bridge 8 and its deformed transition sections 10 and 12 at each end 9*a* and 9*b* of the slot 9. While the implant insertion device engages the bridge 8 at its transition sections 10 and 12, the implant insertion device may extend beyond the transition sections 10 and 12 and engage the legs 16 and 17 to increase surface area contact between the implant insertion device and the implant 5. After implantation into bone, bones, or bone pieces and a release of the implant insertion device, including if necessary a heating of the implant 5, the implant 5 delivers the energy stored in the transition sections 10 and 12 such that the bridge 8 attempts to transition from its insertion form to its natural form, resulting in the legs 16 and 17 attempting to move from their insertion position to their natural position whereby the implant 5 affixes the bone, bones, or bone pieces through an application of a compressive force thereto.

Figure 2A:
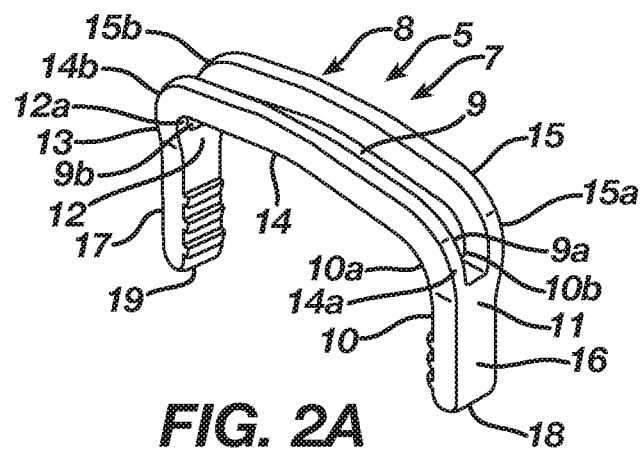
FIG. 2A is an isometric view illustrating the shape memory implant according to the first embodiment in an insertion shape.
Figure 2B:
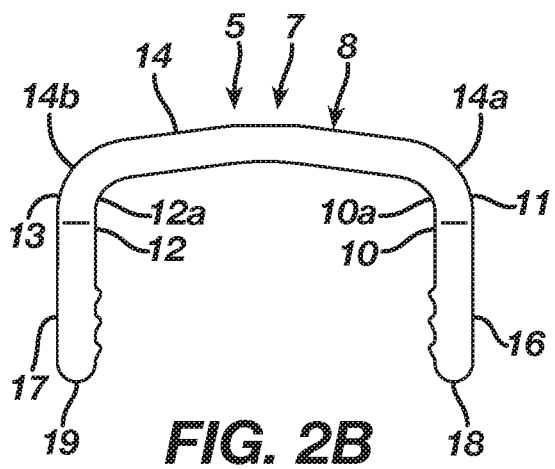
FIG. 2B is a side view thereof.
Figure 2C:
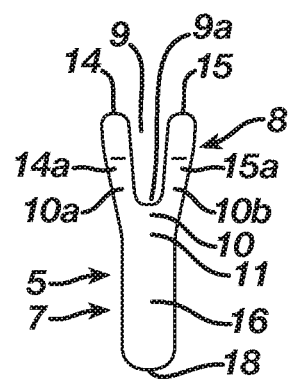
FIG. 2C is an end view thereof.
Figure 2D:
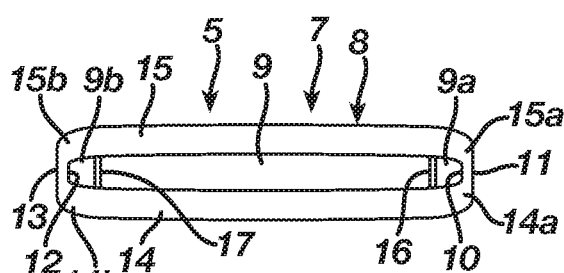
FIG. 2D is a top view thereof.
Figure 2E:
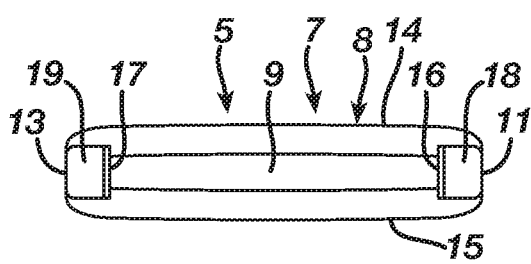
FIG. 2E is a bottom view thereof.
Figure 2F:
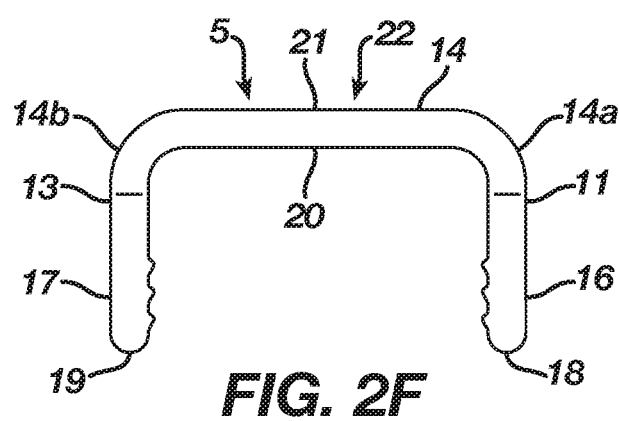
FIG. 2F is a side view illustrating an alternative insertion shape for the shape memory implant according to the first embodiment.

Although the bridge 8 of the implant 5 according to the first embodiment includes the transition sections 10 and 12, the bridge 8, alternatively, may include a transition section 20 located at a center section 21 of the implant 5 and thus the bridge 8. The regular inherent shape of the implant 5, as illustrated in FIGS. 1A-1E, is its natural shape 6 where the transition section 20 locates the bridge 8 in a natural form consisting of a closed or angular profile whereby the ends 11 and 13 reside at a first distance and the legs 16 and 17 reside in a natural position whereby the legs 16 and 17 are convergent and spaced apart at a first distance. Nevertheless, as illustrated in FIG. 2F, the implant 5 is deformable under the action of superelasticity or temperature dependent shape memory to an insertion shape 22 where the transition section 20 deforms to store energy while also moving the bridge 8 from its natural form to an insertion form which is an open or substantially linear profile whereby the ends 11 and 13 reside at a second distance that is greater than the first distance and the legs 16 and 17 reside in an insertion position whereby the legs 16 and 17 are substantially parallel and spaced apart at a second distance that is greater than the first distance. Since the insertion shape 22 is not the regular inherent shape of the implant 5, the bridge 8 typically is mechanically constrained using an implant insertion device whereby the implant insertion device maintains the bridge 8 in its insertion form. In order to facilitate engagement of an implant insertion device with the implant 5, the bridge 8 includes the slot 9 that receives the implant insertion device therethrough such that the implant insertion device engages the bridge 8 at each end 9*a* and 9*b* of the slot 9. In particular, the implant insertion device passes through the slot 9 and engages the bridge 8 interior to its ends 11 and 13 thereby constraining the bridge 8 deformed at the transition section 20 to maintain the implant 5 in its insertion shape 7. The implant insertion device of the present invention accordingly passes through the slot 9 whereby the implant insertion is sized to engage the bridge 8 at each end 9*a* and 9*b* of the slot 9 adjacent the ends 11 and 13 of the bridge 8. While the implant insertion device engages the bridge 8 adjacent its ends 11 and 12, the implant insertion device may extend beyond the bridge 8 and engage the legs 16 and 17 to increase surface area contact between the implant insertion device and the implant 5. After implantation into bone, bones, or bone pieces and a release of the implant insertion device including if necessary a heating of the implant 5, the implant 5 delivers the energy stored in the transition section 20 such that the bridge 8 attempts to transition from its open insertion form to its closed natural form, resulting in the legs 16 and 17 attempting to move from their insertion position to their natural position whereby the implant 5 affixes the bone, bones, or bone pieces through an application of a compressive force thereto.

While the first embodiment of the implant 5 includes either the transition sections 10 and 12 or the transition section 20 to produce deformation thereof, one of ordinary skill in the art will recognize that the bridge 8 of the implant 5 may include both the transition sections 10 and 12 and the transition section 20 to produce deformation thereof. Moreover, while the bridge 8 in the first embodiment includes an angular profile in the natural shape of the implant 5, it should be understood by one of ordinary skill in the art that a bridge 8 incorporating the transition sections 10 and 12 may include a substantially linear profile for the natural shape of the implant 5.

Figure 3A:
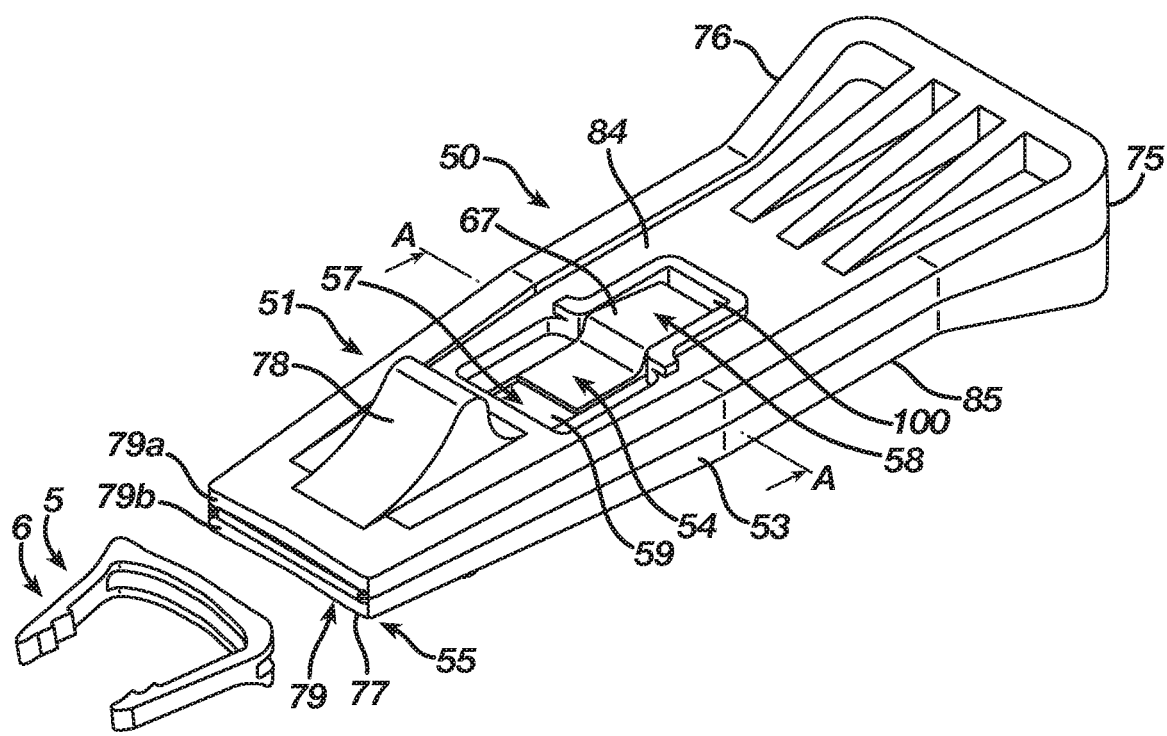
FIG. 3A is an isometric view illustrating an implant insertion device in an unloaded position and a shape memory implant according to the first embodiment in its natural shape.

FIGS. 3A-10E illustrate an implant insertion device 50 that engages an implant 5 and retains the implant 5 in its insertion shape 7. FIGS. 3A-3C illustrate the implant insertion device 50 in an unloaded position 51 prior to its loading with the implant 5 or after its delivery of the implant 5 whereby the implant 5 releases from the implant insertion device 50 without obstruction. FIGS. 4A-4C illustrate the implant insertion device 50 in a loaded position 52 whereby the implant insertion device 50 may be loaded with the implant 5 such that the implant insertion device 50 retains the implant 5 in its insertion shape 7. The implant insertion device 50 allows a surgeon to manipulate the implant 5 and insert the implant 5 into bone, bones, or bone pieces requiring fixation. FIGS. 5A-9 illustrate a body 53 of the implant insertion device 50 and an implant grip 54 of the implant insertion device 50 that is coupled with the body 53 and is movable relative to the body 53 between a disengaged position 55 shown in FIGS. 3A-3C and an engaged position 56 shown in FIGS. 4A-4C.

The implant grip 54 as illustrated in FIGS. 6-9 includes a paddle 57 secured with an actuator 58. The paddle 57 in the preferred embodiment as illustrated in FIGS. 6A-6C includes a first face 86 and a second face 87 and further a shaft 59 with a first end 61 and a second end 62 connected with a blade 60. The first end 61 of the shaft 59 includes at least one opening therethrough and, in the preferred embodiment, openings 63 therethrough that facilitate securing of the actuator 58 with the paddle 57. The blade 60 is elongated relative to the shaft 59 and includes a leading edge 64 between first and second sides 65 and 66. The blade 60 in the preferred embodiment includes a length whereby the blade 60 inserts through the slot 9 while its first and second sides 65 and 66 also abut the bridge 8 at respective ends 9a and 9b of the slot 9. When the implant 5 includes the transition sections 10 and 12 and resides in its insertion shape 7, the blade 60 passes through the slot 9 such that its first and second sides 65 and 66 respectively engage the bridge 8 at the ends 9a and 9b of the slot 9 as well as at the transition sections 10 and 12 thereby constraining the deformed transition sections 10 and 12 to maintain the implant 5 in its insertion shape 7. Alternatively, when the implant 5 includes the transition section 20 and resides in its insertion shape 22, the blade 60 passes through the slot 9 such that its first and second sides 65 and 66 respectively engage the bridge 8 at the ends 9a and 9b of the slot 9 as well as at the bridge 8 interior of its ends 11 and 12 thereby constraining the bridge 8 and the deformed transition section 20 to maintain the implant 5 in its insertion shape 22. The blade 60 in the preferred embodiment further may extend beyond the bridge 8 whereby its first and second sides 65 and 66 respectively engage the legs 16 and 17 to increase surface area contact between the blade 60 and the implant 5. Although the preferred embodiment discloses the blade 60 elongated relative to the shaft 59, one of ordinary skill in the art will recognize that the blade 60 and the shaft 59 may include the same length or any shape suitable to couple with the body 53 while also inserting through the slot 9 and engaging the implant 5.

Figure 7A:
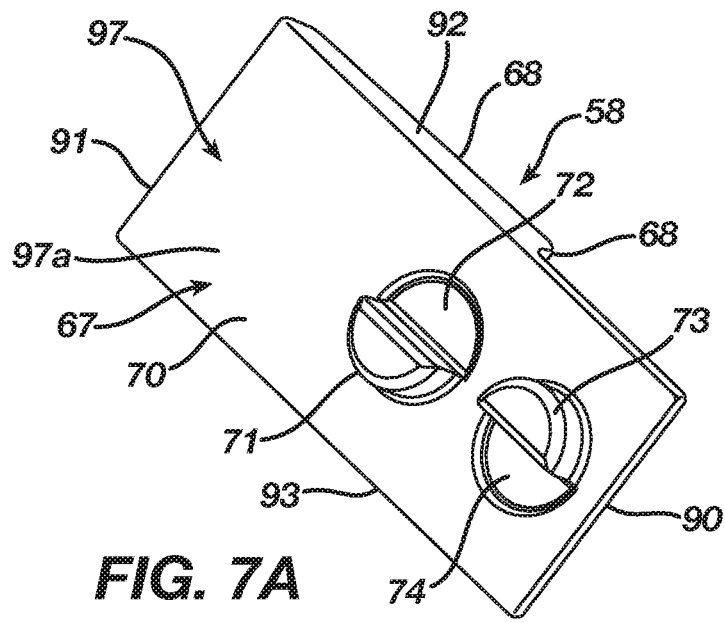
FIG. 7A is an isometric view illustrating an actuator member of an actuator for an implant grip of the implant insertion device.
Figure 7B:
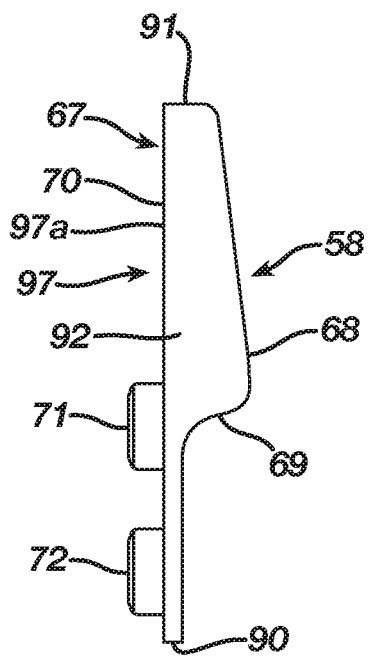
FIG. 7B is a side view illustrating the actuator member of an actuator for an implant grip of the implant insertion device.
Figure 7C:
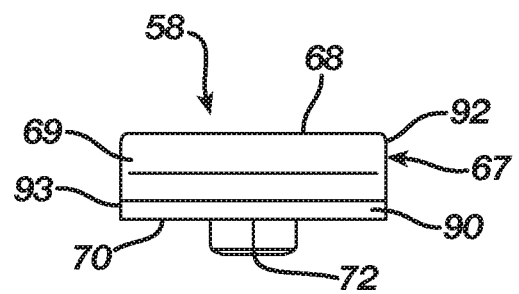
FIG. 7C is a bottom view illustrating the actuator member of an actuator for an implant grip of the implant insertion device.

The actuator 58 includes a slider 67 as illustrated in FIGS. 7A-7C that, in the preferred embodiment, is manufactured to permit coupling of a first slider 67 opposed to a second slider 67 such that the first and second sliders 67 form the actuator 58 secured with the paddle 57. The slider 67 includes first and second ends 90 and 91, first and second sides 92 and 93, and a front surface 68 defining a protrusion 69 that allows manipulation of the slider 67. The slider 67 further includes a rear surface 70 defining at least one peg and at least one adjacent cavity and, in the preferred embodiment, pegs 71 and 72 and respective adjacent cavities 73 and 74. The peg 71 and its adjacent cavity 73 and the peg 72 and its adjacent cavity 74 produce a complementary fit whereby a first slider 67 opposed to a second slider 67 results in first slider pegs 71 and 72 inserting respectively into second slider cavities 73 and 74 and second slider pegs 71 and 72 inserting respectively into first slider cavities 73 and 74 in order to construct the actuator 58. In the preferred embodiment, the openings 63 of the paddle 57 are sized to receive therethrough respectively the pegs 71 or the pegs 72 of both the opposed first and second sliders 67 such that engagement of the pegs 71 and 72 with an opposed cavity 73 and 74 secures the paddle 57 with the actuator 58.

The body 53 as illustrated in FIGS. 5A-5D and 8-9 includes a first end 75 defining a handle 76 and a second end 77 defining a tamp 79 configured to engage the bridge 8 when the implant 5 resides in its insertion shape 7 or its insertion shape 22. The tamp 79 in the preferred embodiment includes a first tamp section 79a that contacts the first bridge segment 14 and a second tamp section 79b contacts the second bridge segment 15. The body 53 further includes a first surface 84 and a second surface 85, which, in the preferred embodiment, are symmetrical. The handle 76 and tabs 77 at the second end 77 facilitate grasping of the implant insertion device 50 during its use in implanting the implant 5 into bone, bones, or bone pieces requiring fixation. The body 53 defines a channel 80 that receives the implant grip 54 such that the implant grip 54 secures with the body 53 and is movable between its disengaged position 55 and its engaged position 56. The channel 80 includes a channel end 81 and a channel exit 83 at the second end 77 of the body 53 that, in the preferred embodiment, is located between the first and second tamp sections 79a and 79b such that the channel exit 83 aligns with the slot 9 defined by the bridge 8 of the implant 5. The channel 80 adjacent the channel end 81 communicates exterior to the body 53 thereby providing the body 53 with an aperture 82 therethrough that facilitates a securing of the actuator 58 with the paddle 60. The channel 80 in the preferred embodiment is complementary in shape with the paddle 57 in order to receive the paddle 57 therein. In particular, the channel 80 includes a shaft channel 88 complementary in shape with the shaft 59 of the paddle 57 to receive therein the shaft 59 and a blade channel 89 complementary in shape with the blade 60 of the paddle 57 to receive therein the blade 60. In the preferred embodiment, a segment 94 of the shaft channel 88 adjacent the channel end 81 provides communication exterior to the body 53, whereas the blade channel 89 and a segment 95 of the shaft channel 88 adjacent the blade channel 89 are enclosed by the body 53 and thus interior thereto. The body 53 through its enclosure of the segment 95 of the shaft channel 88 forms a stop 96 at the juncture of the segments 94 and 95 of the shaft channel 88. The body 53 in the preferred embodiment may be a single piece or two symmetrical halves secured together using any suitable means such as an adhesive.

Figure 8:
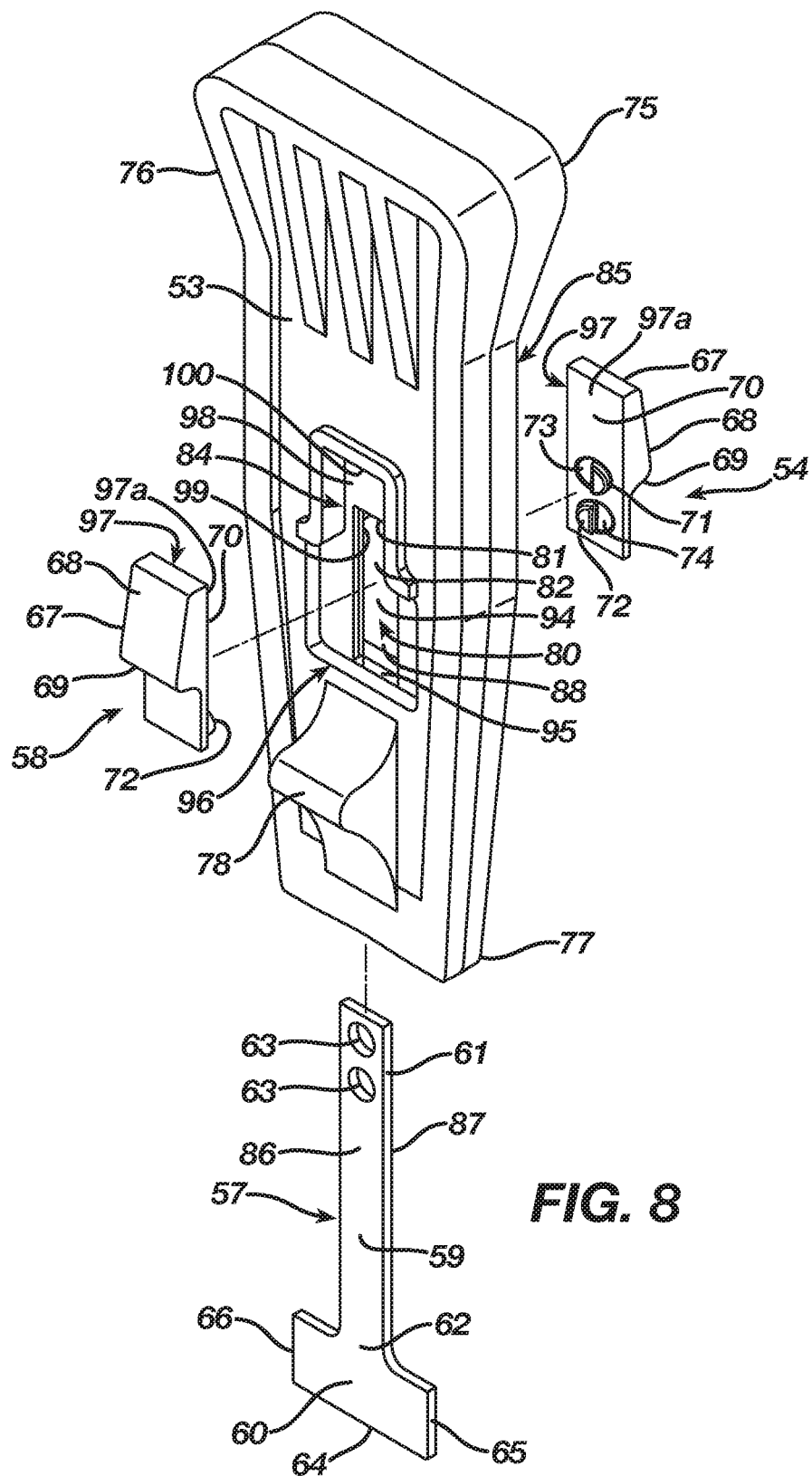
FIG. 8 is an exploded isometric view illustrating the implant insertion device body and the paddle and actuator members of an actuator for the implant grip.
Figure 9:
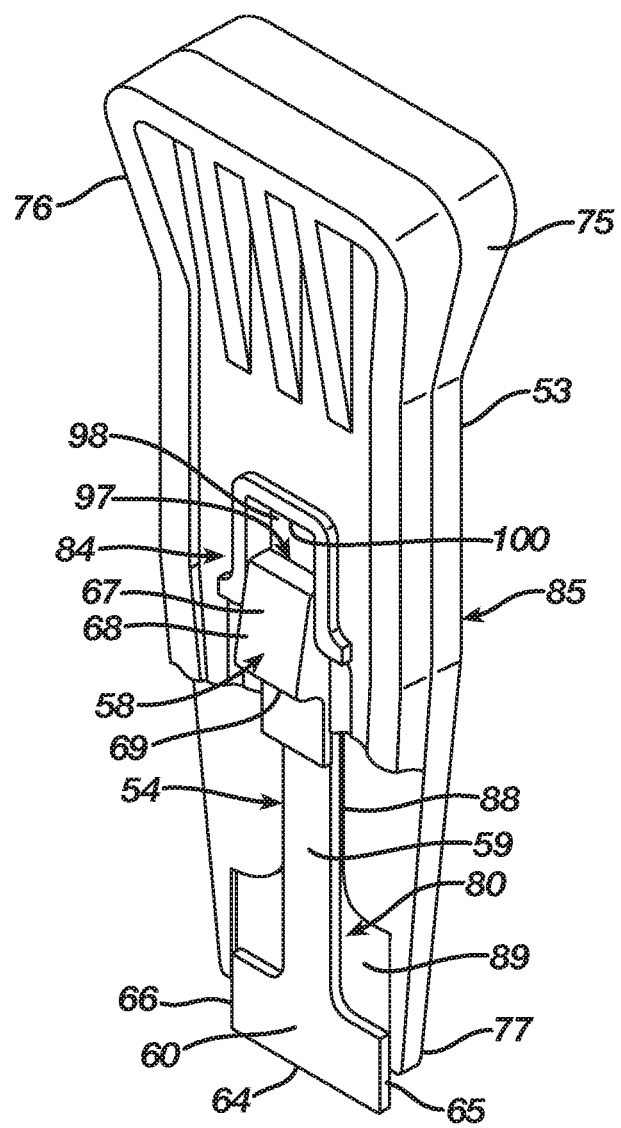
FIG. 9 is an isometric view in partial cross-section taken along lines A-A of FIG. 3A illustrating the implant insertion device.
Figure 10A:
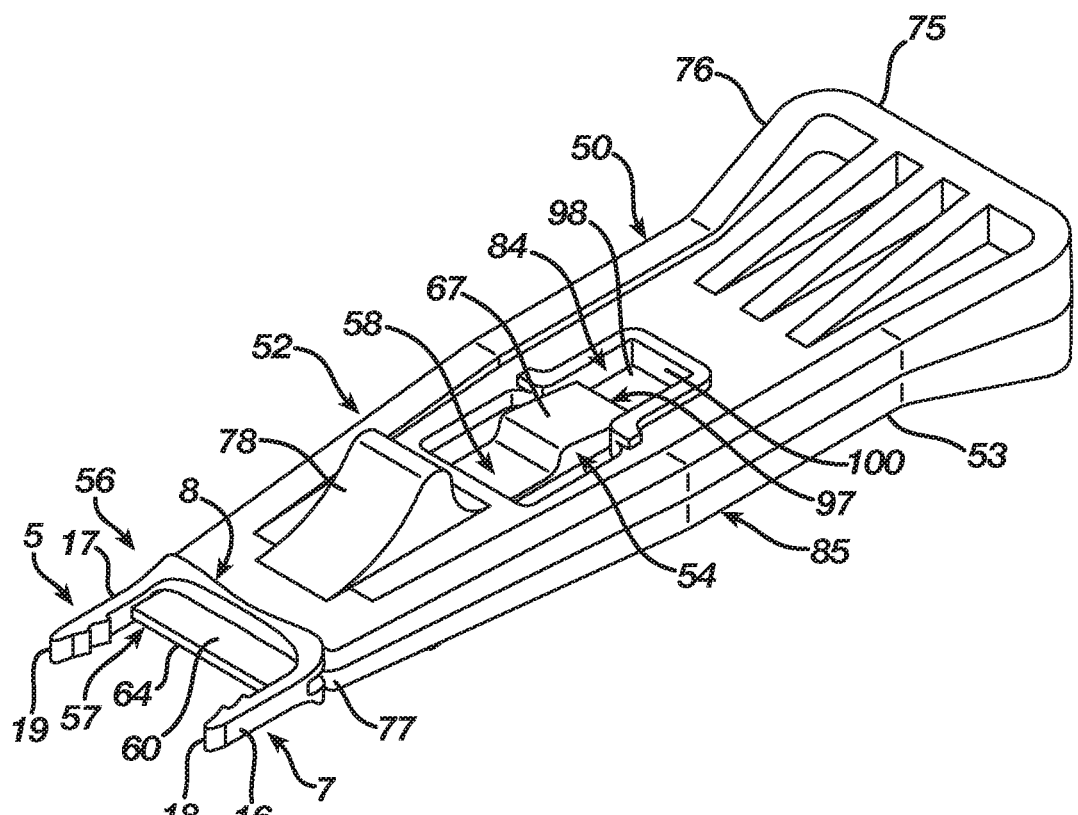
FIG. 10A is an isometric view illustrating the implant insertion device in its loaded position retaining a shape memory implant according to the first embodiment in its insertion shape.
Figure 10B:
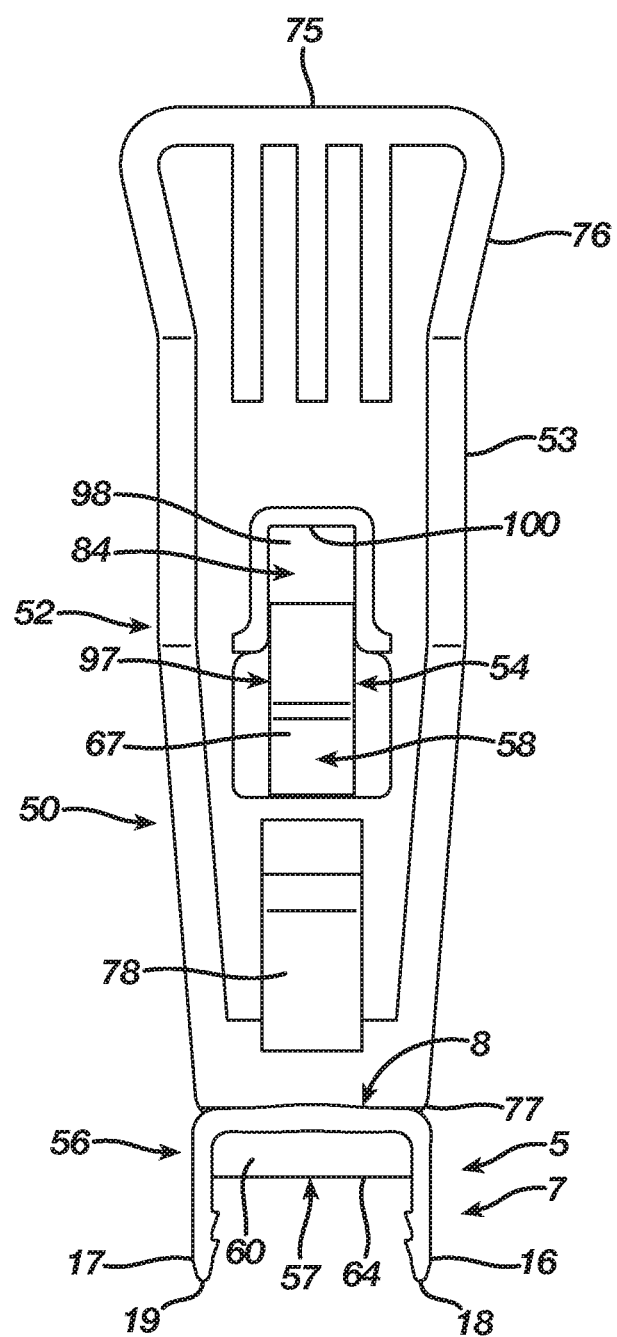
FIG. 10B is a front view illustrating the implant insertion device in its loaded position retaining a shape memory implant according to the first embodiment in its insertion shape.
Figure 10C:
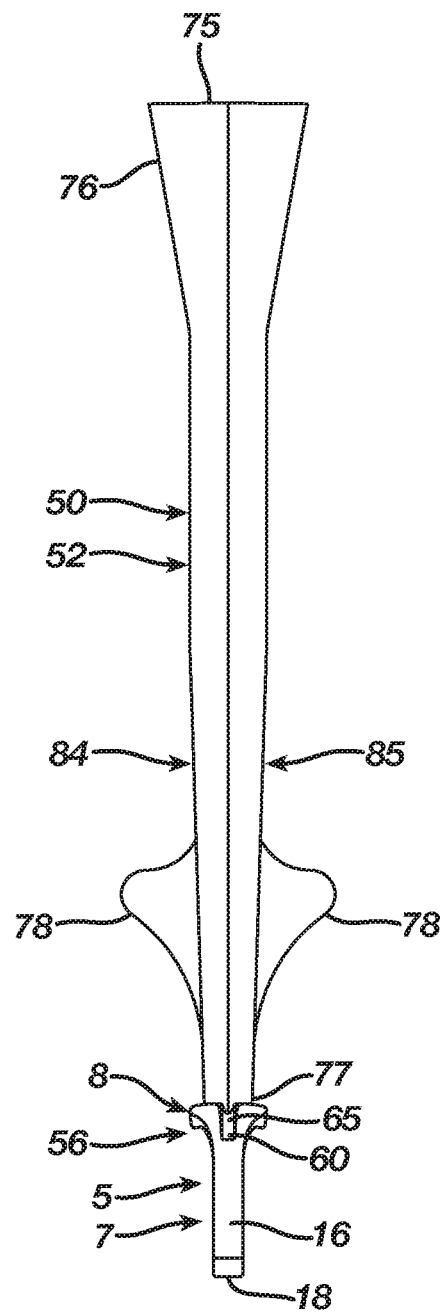
FIG. 10C is a side view illustrating the implant insertion device in its loaded position retaining a shape memory implant according to the first embodiment in its insertion shape.
Figure 10D:
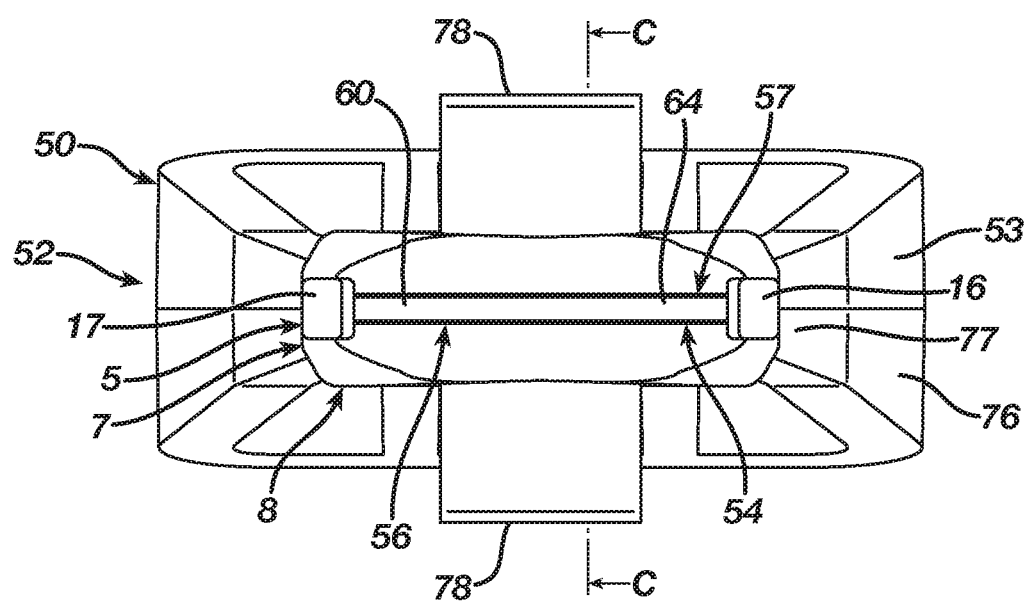
FIG. 10D is a bottom view illustrating the implant insertion device in its loaded position retaining a shape memory implant according to the first embodiment in its insertion shape.
Figure 10E:
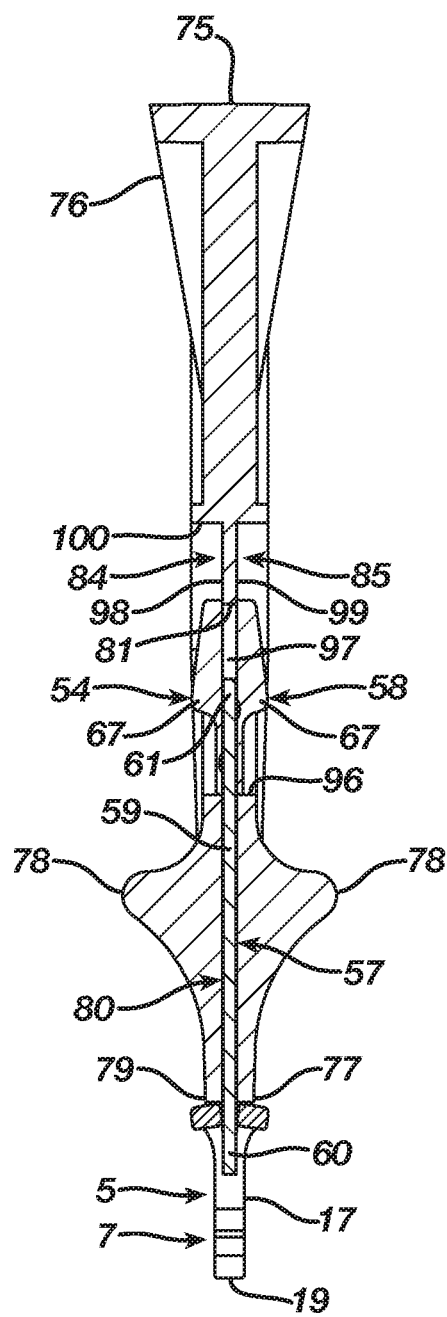
FIG. 10E is a side view in cross-section taken along lines C-C of FIG. 10D illustrating the implant insertion device in its loaded position retaining a shape memory implant according to the first embodiment in its insertion shape.

The channel 80 of the body 53 receives the implant grip 54 and secures the implant grip 54 with the body 53 as follows. The paddle 57 inserts into the channel 80 until the first end 61 resides adjacent the channel end 81 whereby the paddle 57 resides substantially, completely within the channel 80. In particular, the paddle 57 beginning with its shaft 59 at the first end 61 as illustrated in FIGS. 8 and 9 inserts into the channel 80 starting at the channel exit 83. The shaft 59 inserts through the blade channel 89 and into the shaft channel 88 until the shaft 59 resides substantially, completely in the shaft channel 88 with its first end 61 adjacent the channel end 81 and the blade 60 resides substantially, completely in the blade channel 89. The insertion of the paddle 57 into the channel 80 with the first end 61 adjacent the channel end 81 exposes the openings 63 in the shaft 59 exterior to the body 53 via the aperture 82 defined therein. A first slider 67 located at the first surface 84 of the body 53 is placed over the shaft 59 exposed exterior to the body 53 by the segment 88 of the channel 80 such that such that the peg 71 inserts through an upper opening 63 and the peg 72 inserts through a lower opening 63. A second slider 67 located at the second surface 85 of the body 53 is placed over the shaft 59 exposed exterior to the body 53 by the segment 88 of the channel 80 such that such that the peg 71 inserts through the upper opening 63 and the peg 72 inserts through the lower opening 63. The pegs 71 and 72 of the first slider 67 insert respectively into the cavities 73 and 74 of the second slider 67, whereas the pegs 71 and 72 of the second slider 67 insert respectively into the cavities 73 and 74 of the first slider 67. The first and second sliders 67 accordingly frictionally engage over the shaft 59 thereby forming the actuator 58 while also securing the shaft 59 within the body 53 to form the implant grip 54; although an adhesive if desired may be introduced to aid in the securing of the first slider 67 with the second slider 67.

With the first and second sliders 67 coupled together over the paddle 57 to form the actuator 58, the actuator 58 frictionally engages the body 53 in order to introduce a resistance to the movement of the actuator 58 along the body 53 such that a force must be applied to the actuator 58 when moving the implant grip 54 between its disengaged position 55 and its engaged position 56. In particular, the rear surfaces 70 of the first and second sliders 67 adjacent the pegs 71 form a clasp 97 including a clasp surface 97a whereby the clasp 97 frictionally engages the body 53 in that the clasp surface 97a of the first slider 67 contacts the first surface 84 of the body 53 located about the aperture 82 and the clasp surface 97a of the second slider 67 contacts the second surface 85 of the body 53 located about the aperture 82. The first surface 84 of the body 53 in the preferred embodiment may define a clasp receiver 98 configured specifically for frictional contact with the clasp surface 97a of the clasp 97 defined by the first slider 67, whereas the second surface 85 of the body 53 in the preferred embodiment may define a clasp receiver 99 configured specifically for frictional contact with the clasp surface 97a of the clasp 97 defined by the second slider 67.

Figure 3B:
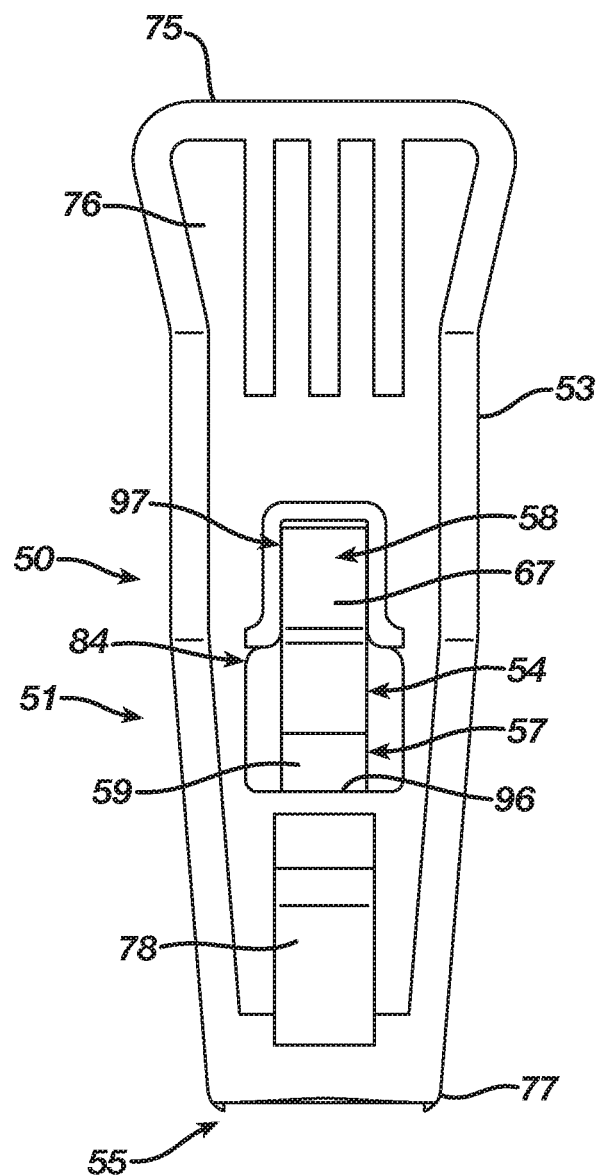
FIG. 3B is a front view illustrating the implant insertion device in its unloaded position.
Figure 3C:
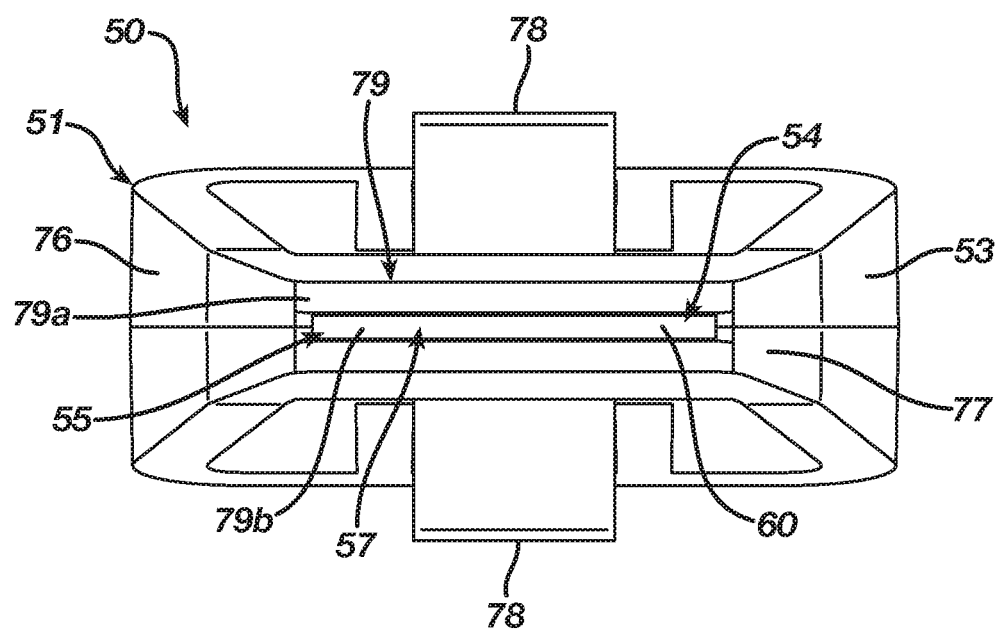
FIG. 3C is a bottom view illustrating the implant insertion device in its unloaded position.
Figure 4A:
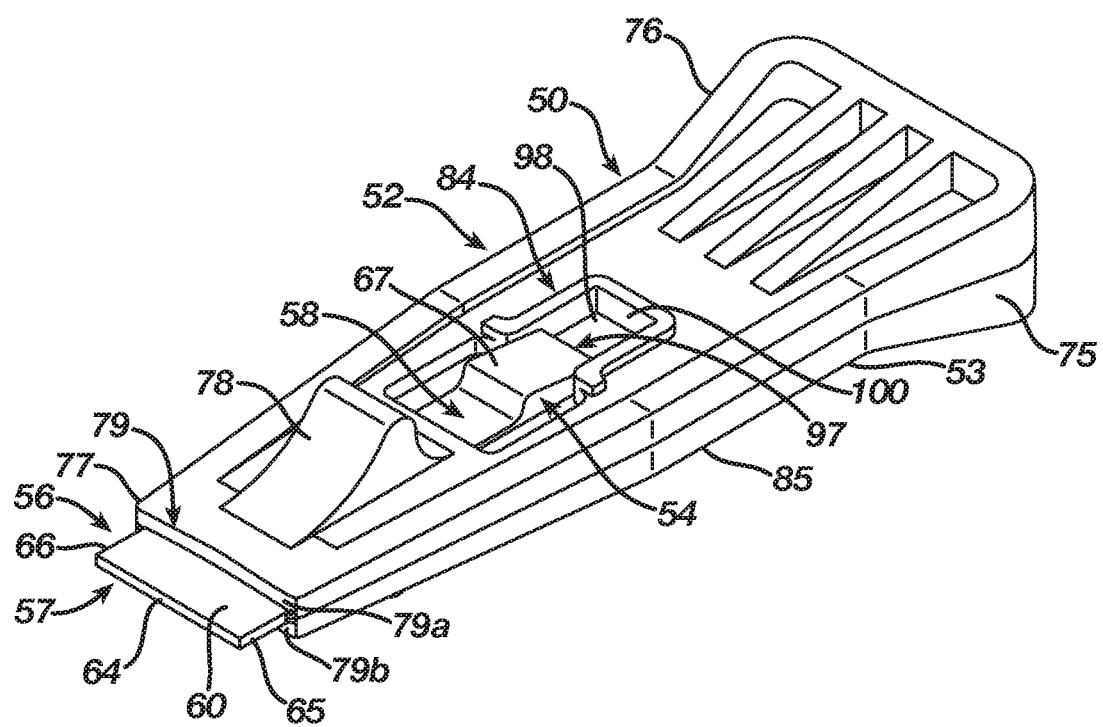
FIG. 4A is an isometric view illustrating the implant insertion device in a loaded position.
Figure 4B:
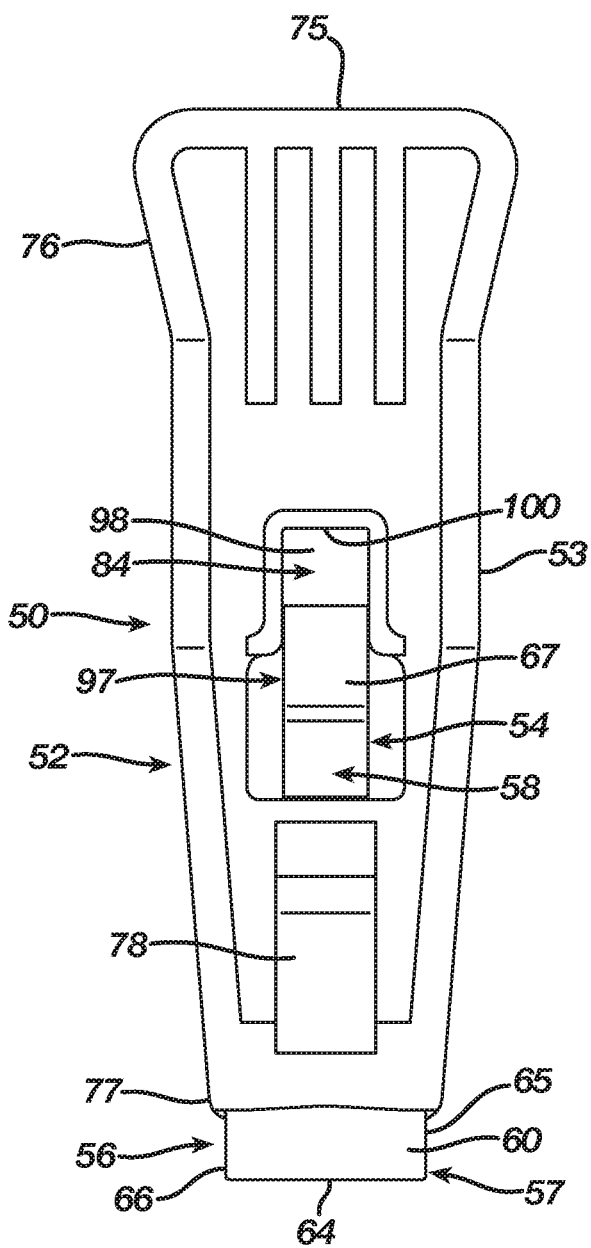
FIG. 4B is a front view illustrating the implant insertion device in its loaded position.
Figure 4C:
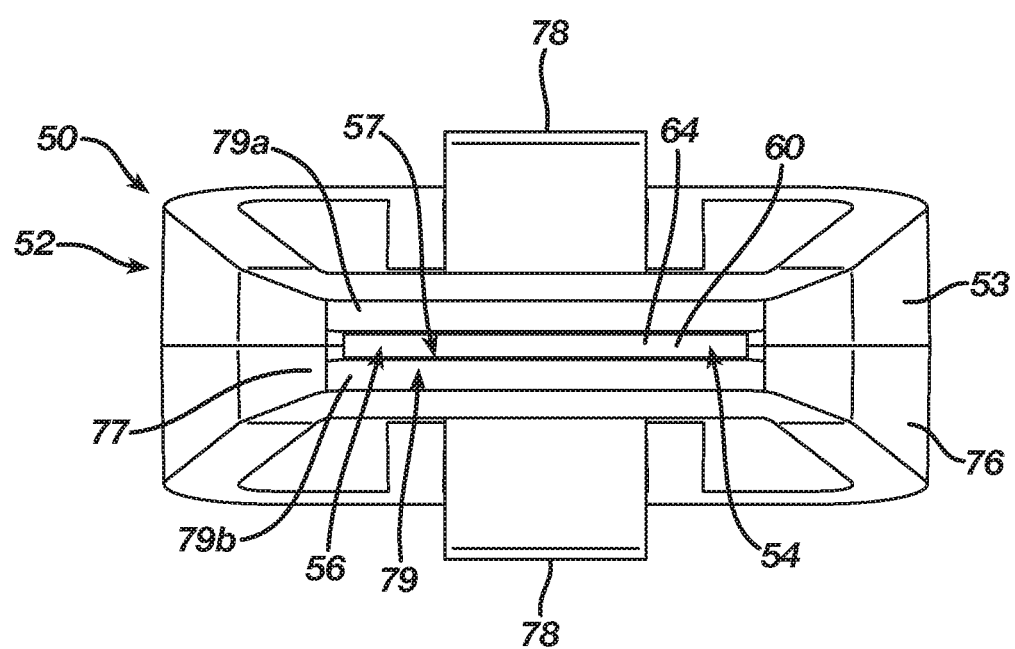
FIG. 4C is a bottom view illustrating the implant insertion device in its loaded position.
Figure 5A:
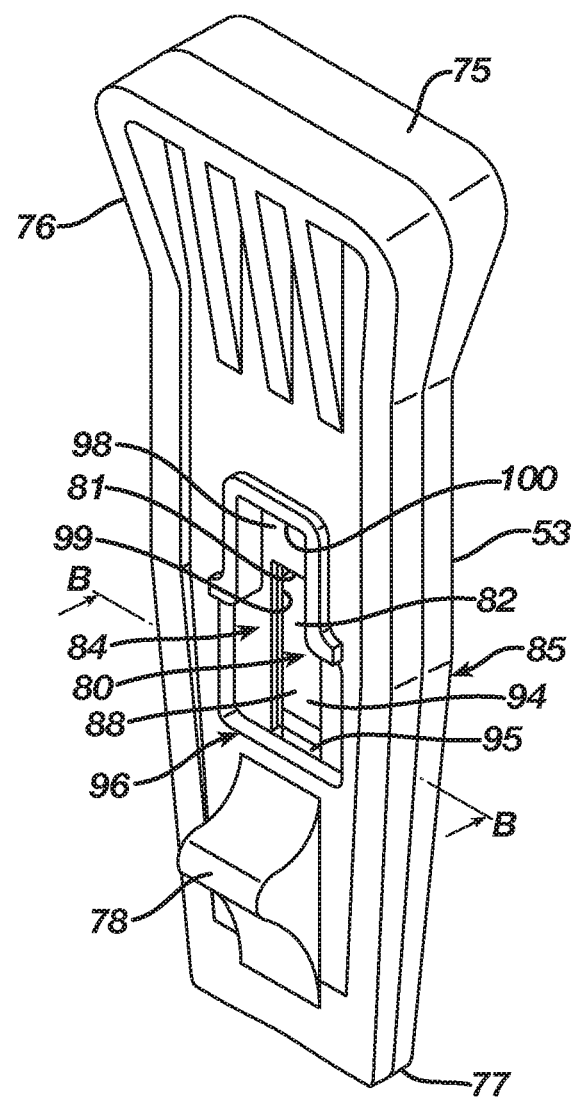
FIG. 5A is an isometric view illustrating an implant insertion device body.
Figure 5B:
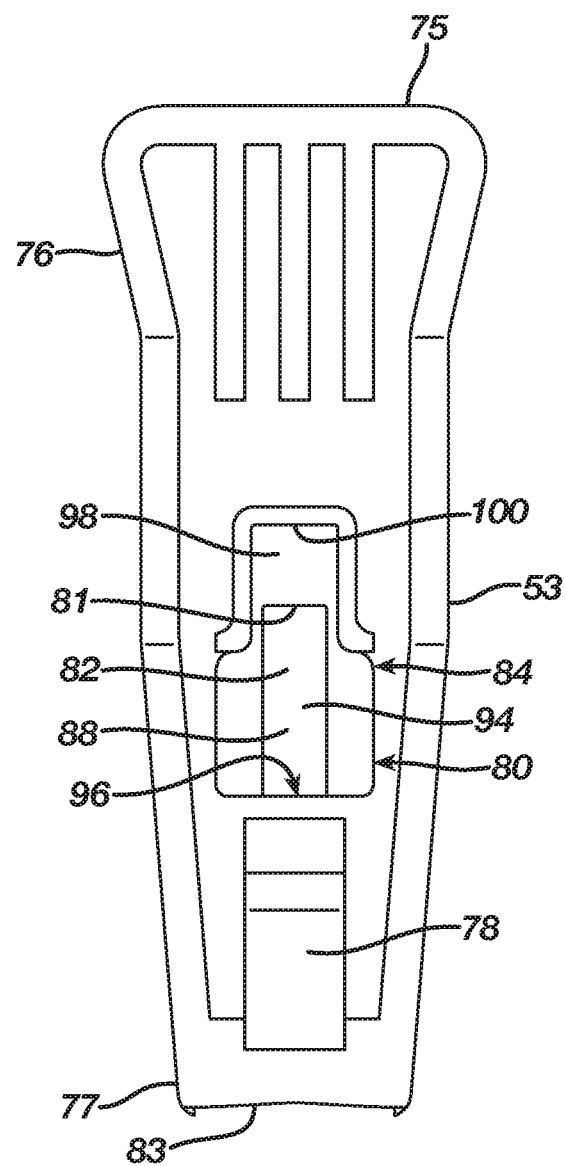
FIG. 5B is a front view illustrating the implant insertion device body.
Figure 5C:
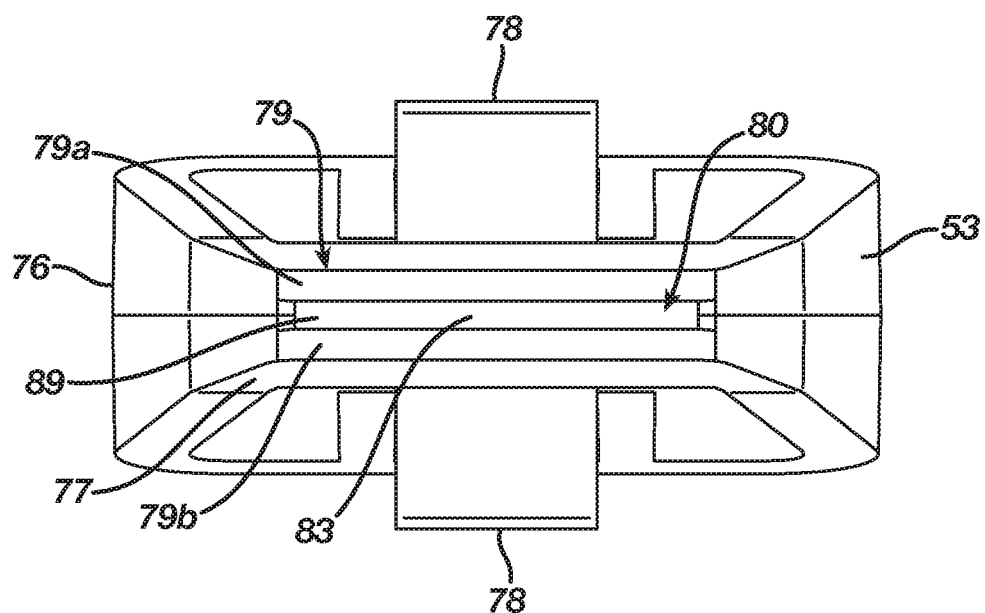
FIG. 5C is a bottom view illustrating the implant insertion device body.
Figure 5D:
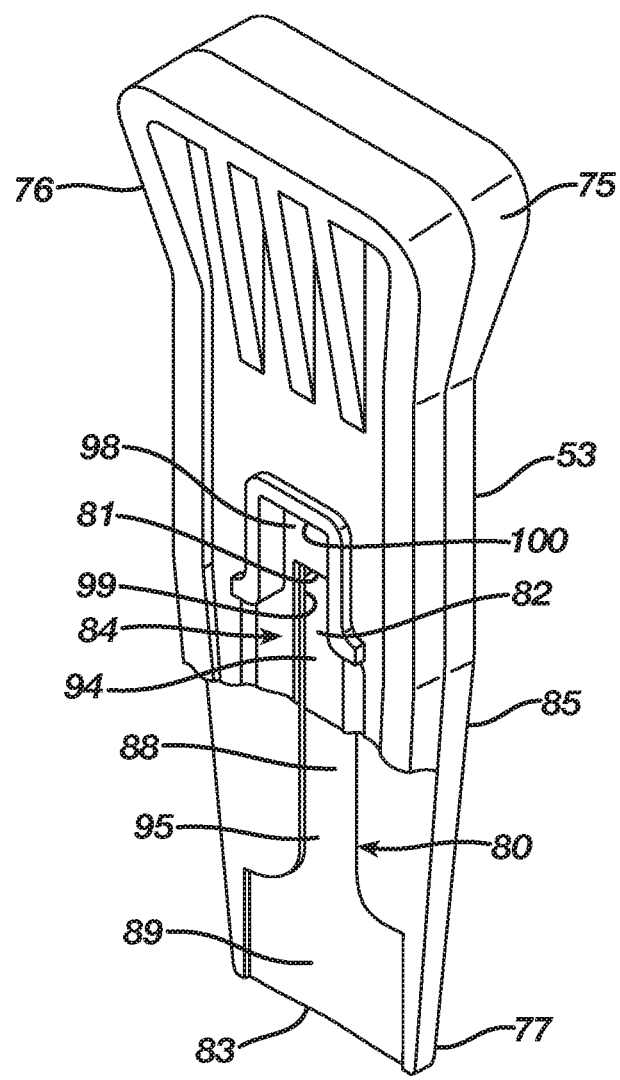
FIG. 5D is an isometric view in partial cross-section taken along lines B-B of FIG. 5A illustrating the implant insertion device body.
Figure 6A:
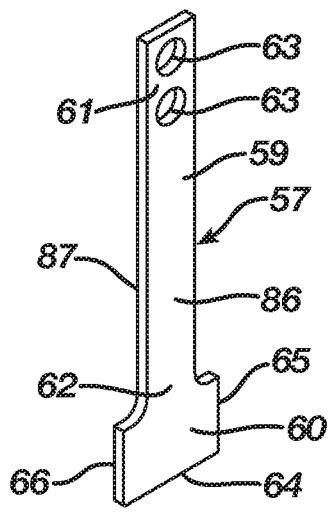
FIG. 6A is an isometric view illustrating a paddle for an implant grip of the implant insertion device.
Figure 6B:
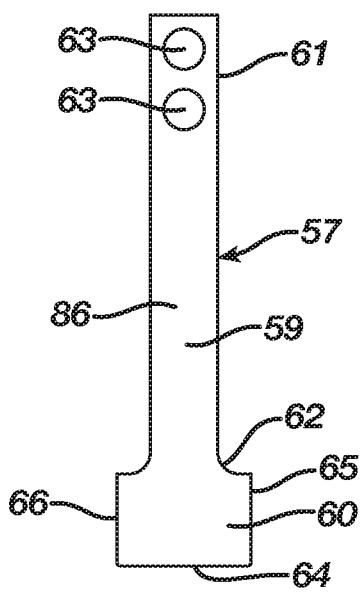
FIG. 6B is a front view illustrating the paddle for an implant grip of the implant insertion device.
Figure 6C:
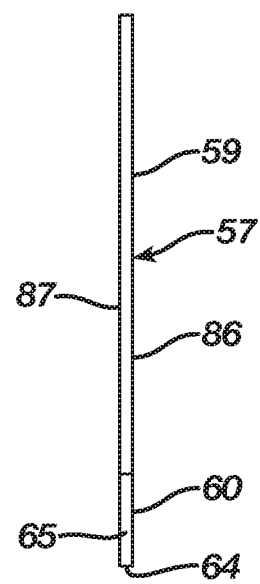
FIG. 6C is a side view illustrating the paddle for an implant grip of the implant insertion device.

The coupling of the actuator 58 and the paddle 57 with the first end 61 thereof located adjacent the channel end 81 of the actuator 58 produces the implant grip 54 configured in its disengaged position 55 as illustrated in FIGS. 3A-3C. Furthermore, the frictional engagement of the clasp 97 for the actuator 58 with the body 53 prevents involuntary movement of the implant grip 54 from its disengaged position 55 such that the paddle 57 remains in the channel 80 and thus retracted within the body 53. An application of a force to the actuator 58 (e.g., pushing on the actuator 58) progresses the implant grip 54 from its disengaged position 55 to its engaged position 56 as illustrated in FIGS. 4A-4C. More particularly, the actuator 58 moves along the body 53 towards the stop 96 of the body 53 until the actuator 58 at the first ends 90 contacts the stop 96 such that the actuator 58 via the shaft 59 advances the blade 60 through the channel exit 83 and exterior to the body 53. An application of a force to the actuator 58 (e.g., pulling on the actuator 58) or to the blade 60 at its leading edge 64 as described herein progresses the implant grip 54 from its engaged position 56 to its disengaged position 55. More particularly, the actuator 58 moves along the body 53 away from the stop 96 of the body 53 such that the actuator 58 via the shaft 59 retracts the blade 60 through the channel exit 83 until the paddle 57 resides substantially, completely in the channel 80 of the body 53. While contact of the first end 61 of the shaft 59 with the channel end 81 limits the retraction of the paddle 57 within the body 53, one or ordinary skill in the art will recognize that the body 53 may include a stop 100 that contacts the actuator 58 at the second ends 91 in order to limit retraction of the paddle 57 within the channel 80 of the body 53. When moving the implant grip 54 between its disengaged position 55 and its engaged position 56, one of ordinary skill in the art will recognize that the actuator 58 due to its frictional engagement with the body 53 may be released at any point between the stop 96 and the stop 100 such that the blade 60 extends from the body 53 at any location between the disengaged position 55 and the engaged position 56.

When receiving the implant 5 in an orthopedic fixation system, the implant insertion device 50 as illustrated in FIG. 3A begins in its unloaded position 51 wherein the implant grip 54 resides in its disengaged position 55. The implant 5 is mechanically deformed from its natural shape 6 to its insertion shape 7 as illustrated in FIGS. 2A-2E or its insertion shape 22 as illustrated in FIG. 2F such that the implant 5 stores mechanical energy. Mechanical deformation of the implant 5 may include cooling of the implant 5 such that the implant 5 transitions from its austenite phase to its martensite phase prior to loading of the implant 5 on the implant insertion device 50. After deformation of the implant 5, the implant insertion device 50 is positioned adjacent the deformed implant 5 whereby the tamp 79 of the body 53 contacts the bridge 8 while the channel exit 83 of the body 53 aligns with the slot 9 defined by the bridge 8; and, in particular, the first tamp section 79a contacts the first bridge segment 14 and the second tamp section 79b contacts the second bridge segment 15.

Once the body 53 of the implant insertion device 50 aligns with the bridge 8 of the implant 5, a force applied to the implant grip 54 moves the implant grip 54 relative to the body 53 from its disengaged position 55 to its engaged position 56 resulting in the implant insertion device 50 as illustrated in FIGS. 10A-10E transitioning from its unloaded position 51 to its loaded position 52 whereby the implant insertion device 50 retains the implant 5 in its insertion shape 7 or 22. The implant grip 54 extends from the body 53 via the channel exit 83 and inserts through the slot 9 while also abutting the bridge 8 at respective ends 9a and 9b of the slot 9 thereby engaging the bridge 8 and constraining the implant 5 in its insertion shape 7 or 22. When the implant 5 includes the transition sections 10 and 12 and resides in its insertion shape 7, the implant grip 54 passes through the slot 9 and engages the bridge 8 at the ends 9a and 9b of the slot 9 as well as at the transition sections 10 and 12 thereby constraining the deformed transition sections 10 and 12 to maintain the implant 5 in its insertion shape 7. Alternatively, when the implant 5 includes the transition section 20 and resides in its insertion shape 22, the implant grip 54 passes through the slot 9 engages the bridge 8 at the ends 9a and 9b of the slot 9 as well as at the bridge 8 interior of its ends 11 and 12 thereby constraining the bridge 8 and the deformed transition section 20 to maintain the implant 5 in its insertion shape 22. The implant grip 54 in the preferred embodiment further may extend beyond the bridge 8 whereby the implant grip 54 engages the legs 16 and 17 to increase surface area contact between the implant grip 54 and the implant 5.

More particularly, a force applied to the actuator 58 progresses the actuator 58 along the body 53 towards the stop 96 of the body 53 until the actuator 58 at the first ends 90 contacts the stop 96 such that the actuator 58 via the shaft 59 advances the blade 60 beginning at its leading edge 64 through the channel exit 83 and exterior to the body 53 such that the blade 60 inserts through the slot 9 while its first and second sides 65 and 66 respectively abut the bridge 8 at the ends 9a and 9b of the slot 9 thereby engaging the bridge 8 and constraining the implant 5 in its insertion shape 7 or 22. When the implant 5 includes the transition sections 10 and 12 and resides in its insertion shape 7, the blade 60 passes through the slot 9 such that its first and second sides 65 and 66 respectively engage the bridge 8 at the ends 9a and 9b of the slot 9 as well as at the transition sections 10 and 12 thereby constraining the deformed transition sections 10 and 12 to maintain the implant 5 in its insertion shape 7. Alternatively, when the implant 5 includes the transition section 20 and resides in its insertion shape 22, the blade 60 passes through the slot 9 such that its first and second sides 65 and 66 respectively engage the bridge 8 at the ends 9a and 9b of the slot 9 as well as at the bridge 8 interior of its ends 11 and 12 thereby constraining the bridge 8 and the deformed transition section 20 to maintain the implant 5 in its insertion shape 22. The blade 60 in the preferred embodiment further may extend beyond the bridge 8 whereby its first and second sides 65 and 66 respectively engage the legs 16 and 17 to increase surface area contact between the blade 60 and the implant 5.

While the implant 5 may be mechanically deformed from its natural shape 6 to its insertion shape 7 or 22 prior to its loading on the implant insertion device 50, the implant insertion device 50 may be employed during its loading with the implant 5 to mechanically deform the implant 5 from its natural shape 6 and to its insertion shape 7 or 22. The implant insertion device 50 is positioned adjacent the implant 5 in its natural shape 6 whereby the tamp 79 of the body 53 contacts the bridge 8 while the channel exit 83 of the body 53 aligns with the slot 9 defined by the bridge 8; and, in particular, the first tamp section 79a contacts the first bridge segment 14 and the second tamp section 79b contacts the second bridge segment 15. Once the body 53 of the implant insertion device 50 aligns with the bridge 8 of the implant 5, a force applied to the implant grip 54 moves the implant grip 54 relative to the body 53 whereby the implant grip 54 extends from the body 53 via the channel exit 83 and inserts through the slot 9. The implant grip 54 abuts the bridge 8 at respective ends 9a and 9b of the slot 9 and due to the force imparted thereto deforms the bridge 8 thereby transitioning the implant 5 from its natural shape 6 to its insertion shape 7 or 22 and constraining the implant 5 as illustrated in FIGS. 10A-10E. When the implant 5 includes the transition sections 10 and 12, the implant grip 54 passes through the slot 9 and engages the bridge 8 at the ends 9a and 9b of the slot 9 as well as at the transition sections 10 and 12 such that the implant grip 54 due to the force imparted thereto deforms the transition sections 10 and 12 thereby transitioning the implant 5 from its natural shape 6 to its insertion shape 7. Alternatively, when the implant 5 includes the transition section 20, the implant grip 54 passes through the slot 9 engages the bridge 8 at the ends 9a and 9b of the slot 9 as well as at the bridge 8 interior of its ends 11 and 12 such that the implant grip 54 due to the force imparted thereto deforms the transition section 20 thereby transitioning the implant 5 from its natural shape 6 to its insertion shape 22. The implant grip 54 in the preferred embodiment further may extend beyond the bridge 8 whereby the implant grip 54 engages the legs 16 and 17 to increase surface area contact between the implant grip 54 and the implant 5.

More particularly, a force applied to the actuator 58 progresses the actuator 58 along the body 53 towards the stop 96 of the body 53 until the actuator 58 at the first ends 90 contacts the stop 96 whereby the actuator 58 via the shaft 59 advances the blade 60 beginning at its leading edge 64 through the channel exit 83 and exterior to the body 53. The blade 60 inserts through the slot 9 while its first and second sides 65 and 66 respectively abut the bridge 8 at the ends 9a and 9b of the slot 9 such that the blade 60 due to the force imparted thereto by the actuator 58 deforms the bridge 8 thereby transitioning the implant 5 from its natural shape 6 to its insertion shape 7 or 22. When the implant 5 includes the transition sections 10 and 12, the blade 60 passes through the slot 9 while its first and second sides 65 and 66 respectively engage the bridge 8 at the ends 9a and 9b of the slot 9 as well as at the transition sections 10 and 12 such that the blade 60 due to the force imparted thereto by the actuator 58 deforms transition sections 10 and 12 thereby transitioning the implant 5 from its natural shape 6 to its insertion shape 7. Alternatively, when the implant 5 includes the transition section 20, the blade 60 passes through the slot 9 while its first and second sides 65 and 66 respectively engage the bridge 8 at the ends 9a and 9b of the slot 9 as well as at the bridge 8 interior of its ends 11 and 12 such that the blade 60 due to the force imparted thereto by the actuator 58 deforms transition section 20 thereby transitioning the implant 5 from its natural shape 6 to its insertion shape 22. The blade 60 in the preferred embodiment further may extend beyond the bridge 8 whereby its first and second sides 65 and 66 respectively engage the legs 16 and 17 to increase surface area contact between the blade 60 and the implant 5.

When delivering the implant 5 to bone, bones, or bone pieces, the implant insertion device 50 as illustrated in FIGS. 10A-10E begins in its loaded position 52 wherein the implant grip 54 in its engaged position 56 constrains the implant 5 in its insertion shape 7 or 22. In order to release the implant 5 from the implant insertion device 50, a force applied to the implant grip 54 either at the leading edge 64 of the blade 60 as described herein or the actuator 58 progresses the implant grip 54 from its engaged position 56 to its disengaged position 55. The implant grip 54 exits from the slot 9 defined by the bridge 8 and retracts into the body 53 via the channel exit 83 such that the implant grip 54 releases the bridge 8 at respective ends 9a and 9b of the slot 9 resulting in an attempted transition of the implant 5 from its insertion shape 7 or 22 to its natural shape 6 whereby the implant 5 delivers the energy stored therein to the bone, bones, or bone pieces. More particularly, progression of the actuator 58 along the body 53 to the stop 100 thereof moves the blade 60 via the shaft 59 such that the blade 60 exits from the slot 9 defined by the bridge 8 and retracts into the body 53 via the channel exit 83. The blade 60 at its first and second ends 65 and 66 releases the bridge 8 at respective ends 9a and 9b of the slot 9 thereby allowing an attempted transition of the implant 5 from its insertion shape 7 or 22 to its natural shape 6. When the implant 5 includes the transition sections 10 and 12, the blade 60 releases the transition sections 10 and 12 as well as the bridge 8 at the ends 9a and 9b of the slot 9. Alternatively, when the implant 5 includes the transition section 20, the blade 60 releases the bridge 8 interior of its ends 11 and 12 as well as the bridge 8 at the ends 9a and 9b of the slot 9. The blade 60 further disengages from the legs 16 and 17 when the blade 60 extends beyond the bridge 8 and to the legs 16 and 17 in order to increase surface area contact between the blade 60 and the implant 5.

Figure 11A:
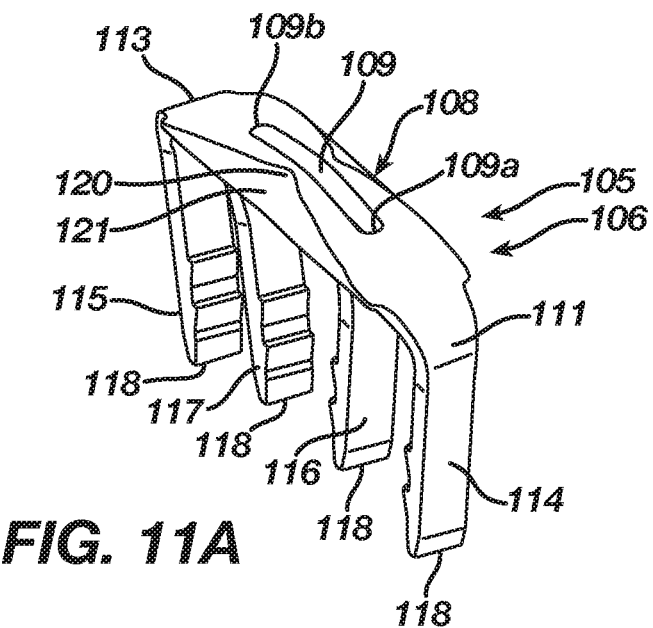
FIG. 11A is an isometric view illustrating a shape memory implant according to a second embodiment in a natural shape.
Figure 11B:
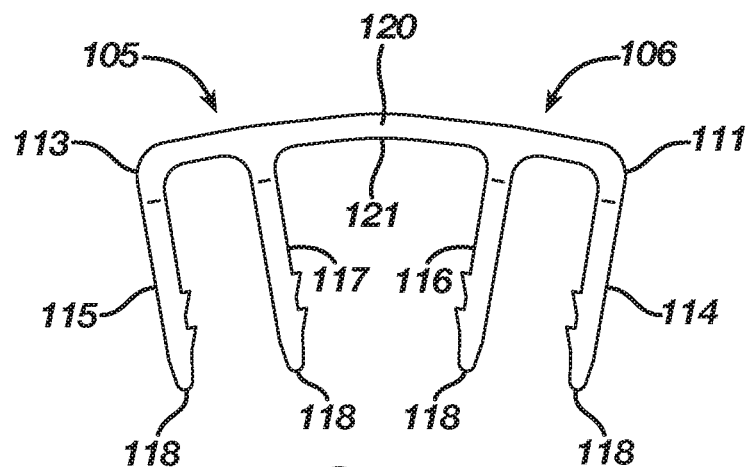
FIG. 11B is a side view thereof.
Figure 12A:
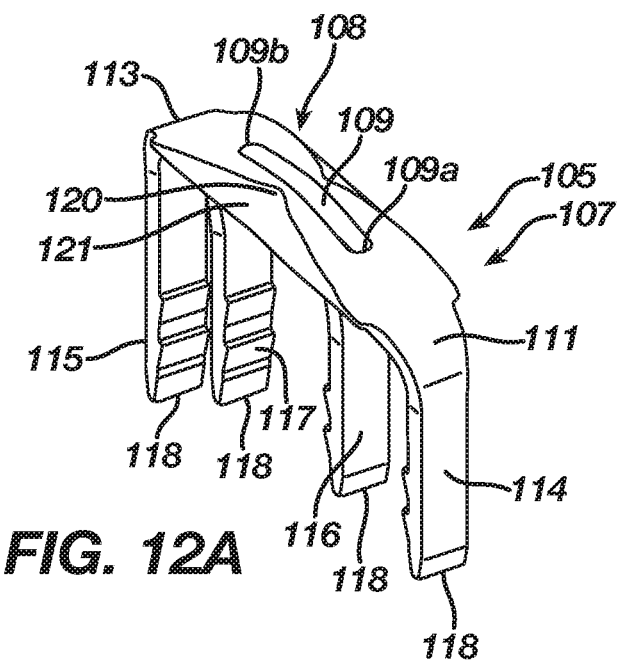
FIG. 12A is an isometric view illustrating the shape memory implant according to the second embodiment in an insertion shape.
Figure 12B:
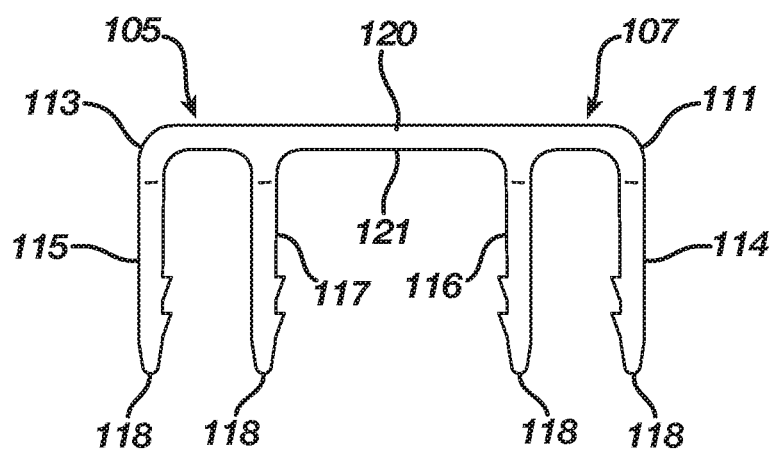
FIG. 12B is a side view thereof.

FIGS. 11A-11B illustrate an orthopedic implant 105 according to a second embodiment in a natural shape 106, whereas FIGS. 12A-12B illustrate the orthopedic implant 105 in an insertion shape 107. The implant 105 in the second embodiment may be manufactured from a shape memory material with superelastic or temperature dependent properties (e.g., Nitinol) such that the implant 105 transitions between its natural shape 106 and its insertion shape 107. The implant 105 when deformed from its natural shape 106 to its insertion shape 107 stores energy deliverable to bone, bones, or bone pieces. In accordance with its manufacture from shape memory material, the implant 105 begins in its natural shape 106, is transitionable to its insertion shape 107, and, once implanted in bone, bones, or bone pieces, attempts to transition from its insertion shape 107 to its natural shape 106 whereby the implant 105 delivers the energy stored therein to the bone, bones, or bone pieces in order to affix the bone, bones, or bone pieces and promote a healing thereof. In the second embodiment, attempted transition of the implant 105 from its insertion shape 107 to its natural shape 106 continuously compresses the bone, bones, or bone pieces to promote fusion thereof.

The implant 105 in the second embodiment includes a bridge 108 defining a slot 109 with ends 109a and 109b and a transition section 120 located at a center section 121 of the implant 105 and thus the bridge 108. The implant 105 in the second embodiment includes an anchoring member in the form of a leg 114 extending from the bridge 108 at an end 111 thereof and an anchoring member in the form of a leg 115 extending from the bridge 108 at an end 113 thereof. The implant 105 in the second embodiment includes an anchoring member in the form of a leg 116 interior of the leg 114 and extending from the bridge 108 adjacent the end 109a of the slot 109 and an anchoring member in the form of a leg 117 interior of the leg 115 and extending from the bridge 108 adjacent the end 109b of the slot 109. In the second embodiment, the legs 114-117 are formed integrally with the bridge 108. Each leg 114-117, which has a respective tip 118, may include barbs thereon that improve the pull-out resistance of the implant 105. The implant 105 includes anchoring members in the form of legs 114-117 in order to facilitate a securing of the implant 105 with bone, bones, or bone pieces whereby the bridge 108 between the legs 114 and 117 traverses a fixation zone of the bone, bones, or bone pieces such that the implant 105, after its insertion and attempted transition from the insertion shape 107 to the natural shape 106, delivers energy to the bone, bones, or bone pieces at the fixation zone.

The regular inherent shape of the implant 105, as illustrated in FIGS. 11A-11B, is its natural shape 106 where the transition section 120 locates the bridge 108 in a natural form consisting of a closed or angular profile whereby the ends 111 and 113 reside at a first distance and the legs 114-117 reside in a natural position whereby the legs 116 and 117 are convergent and spaced apart at a first distance and the legs 114 and 115 are convergent and spaced apart at a first distance. Nevertheless, as illustrated in FIGS. 12A-12B, the implant 105 is deformable under the action of superelasticity or temperature dependent shape memory to an insertion shape 107 where the transition section 120 deforms to store energy while also moving the bridge 108 from its natural form to an insertion form which is an open or substantially linear profile whereby the ends 111 and 113 reside at a second distance that is greater than the first distance and the legs 114-117 reside in an insertion position whereby the legs 116 and 117 are substantially parallel and spaced apart at a second distance that is greater than the first distance and the legs 114 and 115 are substantially parallel and spaced apart at a second distance that is greater than the first distance. Since the insertion shape 107 is not the regular inherent shape of the implant 105, the bridge 108 typically is mechanically constrained using the implant insertion device 50 whereby the implant insertion device 50 maintains the bridge 108 in its insertion form. In order to facilitate engagement of an implant insertion device 50 with the implant 105, the bridge 108 includes the slot 109 that receives the implant insertion device 50 therethrough such that the implant insertion device 50 engages the bridge 108 at each end 109a and 109b of the slot 109. In particular, the implant insertion device 50 passes through the slot 109 and engages the bridge 108 where the bridge 108 adjoins the legs 116 and 117 thereby constraining the bridge 108 deformed at the transition section 120 to maintain the implant 105 in its insertion shape 107. The implant insertion device 50 of the present invention accordingly passes through the slot 109 whereby the implant insertion device 50 is sized to engage the bridge 108 at each end 109a and 109b of the slot 109 adjacent the legs 116 and 117. While the implant insertion device 50 engages the bridge 108 adjacent the legs 116 and 117, the implant insertion device 50 may extend beyond the bridge 108 and engage the legs 116 and 117 to increase surface area contact between the implant insertion device 50 and the implant 105. After implantation into bone, bones, or bone pieces and a release of the implant insertion device 50, including if necessary a heating of the implant 105, the implant 105 delivers the energy stored in the transition section 120 such that the bridge 108 attempts to transition from its open insertion form to its closed natural form, resulting in the legs 114-117 attempting to move from their insertion position to their natural position whereby the implant 105 affixes the bone, bones, or bone pieces through an application of a compressive force thereto.

When receiving the implant 105 in an orthopedic fixation system, the implant insertion device 50 begins in its unloaded position 51 wherein the implant grip 54 resides in its disengaged position 55. The implant 105 is mechanically deformed from its natural shape 106 to its insertion shape 107 as illustrated in FIGS. 12A-12B such that the implant 105 stores mechanical energy. Mechanical deformation of the implant 105 may include cooling of the implant 105 such that the implant 105 transitions from its austenite phase to its martensite phase prior to loading of the implant 105 on the implant insertion device 50. After deformation of the implant 105, the implant insertion device 50 is positioned adjacent the deformed implant 105 whereby the tamp 79 of the body 53 contacts the bridge 108 while the channel exit 83 of the body 53 aligns with the slot 109 defined by the bridge 108; and, in particular, the first tamp section 79*a* and the second tamp section 79*b* contact the bridge 108 on opposite sides of the slot 109.

Figure 13A:
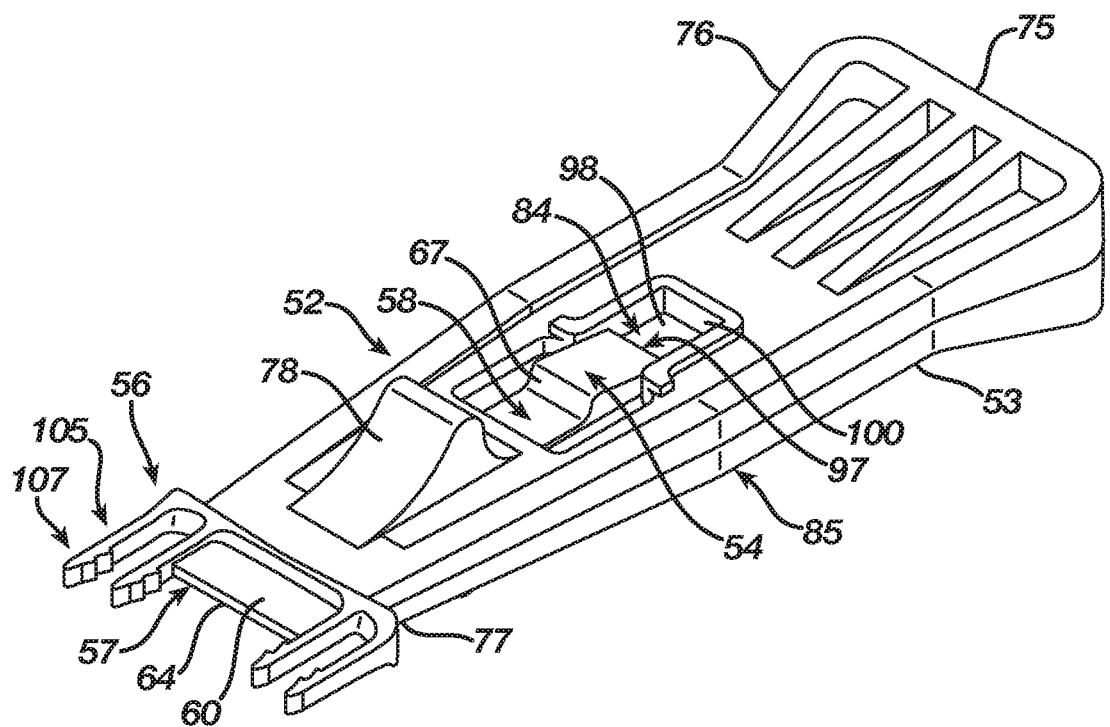
FIG. 13A is an isometric view illustrating the implant insertion device in its loaded position retaining a shape memory implant according to the second embodiment in its insertion shape.
Figure 13B:
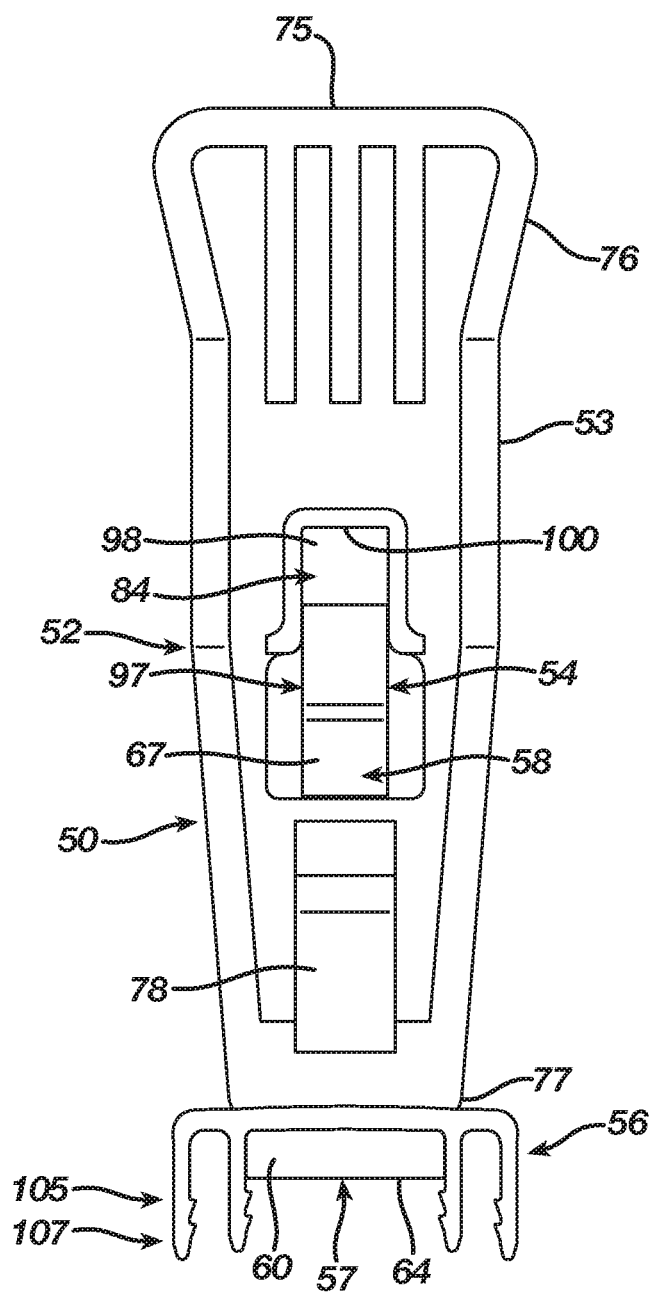
FIG. 13B is a front view illustrating the implant insertion device in its loaded position retaining a shape memory implant according to the second embodiment in its insertion shape.

Once the body 53 of the implant insertion device 50 aligns with the bridge 108 of the implant 105, a force applied to the actuator 58 progresses the actuator 58 along the body 53 towards the stop 96 of the body 53 until the actuator 58 at the first ends 90 contacts the stop 96 such that the actuator 58 via the shaft 59 advances the blade 60 beginning at its leading edge 64 through the channel exit 83 and exterior to the body 53 such that the blade 60 inserts through the slot 109 while its first and second sides 65 and 66 respectively abut the bridge 108 at the ends 109*a* and 109*b* of the slot 109 thereby engaging the bridge 108 and constraining the implant 105 in its insertion shape 107 as illustrated in FIGS. 13A-13B. The blade 60 accordingly passes through the slot 109 such that its first and second sides 65 and 66 respectively engage the bridge 108 at the ends 109*a* and 109*b* of the slot 109 as well as at the bridge 108 where the bridge 108 adjoins the legs 116 and 117 thereby constraining the bridge 108 and the deformed transition section 120 to maintain the implant 105 in its insertion shape 107. The blade 60 in the preferred embodiment further may extend beyond the bridge 108 whereby its first and second sides 65 and 66 respectively engage the legs 116 and 117 to increase surface area contact between the blade 60 and the implant 105.

While the implant 105 may be mechanically deformed from its natural shape 106 to its insertion shape 107 prior to its loading on the implant insertion device 50, the implant insertion device 50 may be employed during its loading with the implant 105 to mechanically deform the implant 105 from its natural shape 106 and to its insertion shape 107. The implant insertion device 50 is positioned adjacent the implant 105 in its natural shape 106 whereby the tamp 79 of the body 53 contacts the bridge 108 while the channel exit 83 of the body 53 aligns with the slot 109 defined by the bridge 108; and, in particular, the first tamp section 79*a* and the second tamp section 79*b* contact the bridge 108 on opposite sides of the slot 109. Once the body 53 of the implant insertion device 50 aligns with the bridge 108 of the implant 105, a force applied to the actuator 58 progresses the actuator 58 along the body 53 towards the stop 96 of the body 53 until the actuator 58 at the first ends 90 contacts the stop 96 whereby the actuator 58 via the shaft 59 advances the blade 60 beginning at its leading edge 64 through the channel exit 83 and exterior to the body 53. The blade 60 inserts through the slot 109 while its first and second sides 65 and 66 respectively abut the bridge 108 at the ends 109*a* and 109*b* of the slot 109 such that the blade 60 due to the force imparted thereto by the actuator 58 deforms the bridge 108 thereby transitioning the implant 105 from its natural shape 106 to its insertion shape 107 and constraining the implant 105 as illustrated in FIGS. 13A-13B. The blade 60 accordingly passes through the slot 109 while its first and second sides 65 and 66 respectively engage the bridge 108 at the ends 109*a* and 109*b* of the slot 109 as well as at the bridge 108 where the bridge 108 adjoins the legs 116 and 117 such that the blade 60 due to the force imparted thereto by the actuator 58 deforms transition section 120 thereby transitioning the implant 105 from its natural shape 106 to its insertion shape 107. The blade 60 in the preferred embodiment further may extend beyond the bridge 108 whereby its first and second sides 65 and 66 respectively engage the legs 116 and 117 to increase surface area contact between the blade 60 and the implant 105.

When delivering the implant 105 to bone, bones, or bone pieces, the implant insertion device 50 as illustrated in FIGS. 13-13B begins in its loaded position 52 wherein the implant grip 54 in its engaged position 56 constrains the implant 105 in its insertion shape 107. In order to release the implant 105 from the implant insertion device 50, a force applied to the implant grip 54 either at the leading edge 64 of the blade 60 as described herein or the actuator 58 progresses the implant grip 54 from its engaged position 56 to its disengaged position 55. The implant grip 54 exits from the slot 109 defined by the bridge 108 and retracts into the body 53 via the channel exit 83 such that the implant grip 54 releases the bridge 108 at respective ends 109*a* and 109*b* of the slot 109 resulting in an attempted transition of the implant 105 from its insertion shape 107 to its natural shape 106 whereby the implant 105 delivers the energy stored therein to the bone, bones, or bone pieces. More particularly, progression of the actuator 58 along the body 53 to the stop 100 thereof moves the blade 60 via the shaft 59 such that the blade 60 exits from the slot 109 defined by the bridge 108 and retracts into the body 53 via the channel exit 83. The blade 60 at its first and second ends 65 and 66 releases the bridge 108 at respective ends 109*a* and 109*b* of the slot 109 thereby allowing an attempted transition of the implant 105 from its insertion shape 107 to its natural shape 106. The blade 60 accordingly releases the bridge 108 where the bridge 108 adjoins the legs 116 and 117 as well as the bridge 108 at the ends 109*a* and 109*b* of the slot 109. The blade 60 further disengages from the legs 116 and 117 when the blade 60 extends beyond the bridge 108 and to the legs 116 and 117 in order to increase surface area contact between the blade 60 and the implant 105.

Figure 14A:
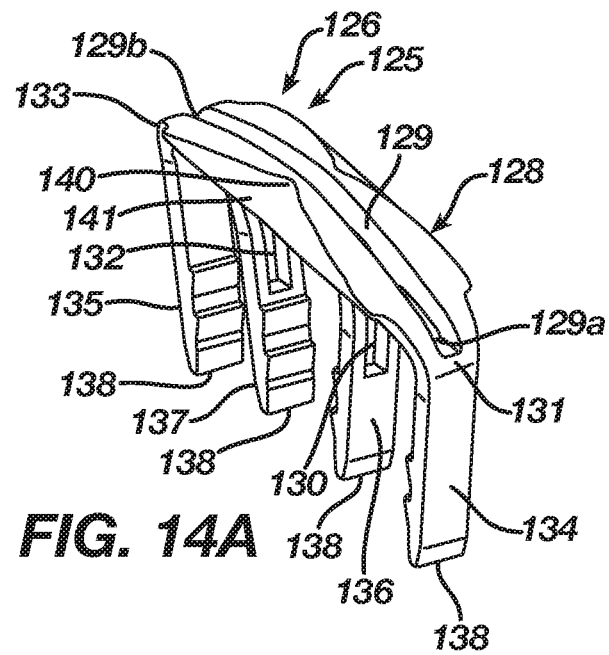
FIG. 14A is an isometric view illustrating a shape memory implant according to a third embodiment in a natural shape.
Figure 14B:
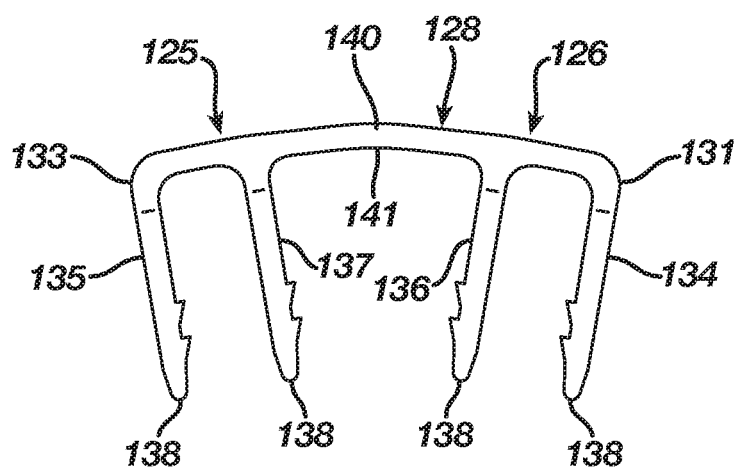
FIG. 14B is a side view thereof.
Figure 15A:
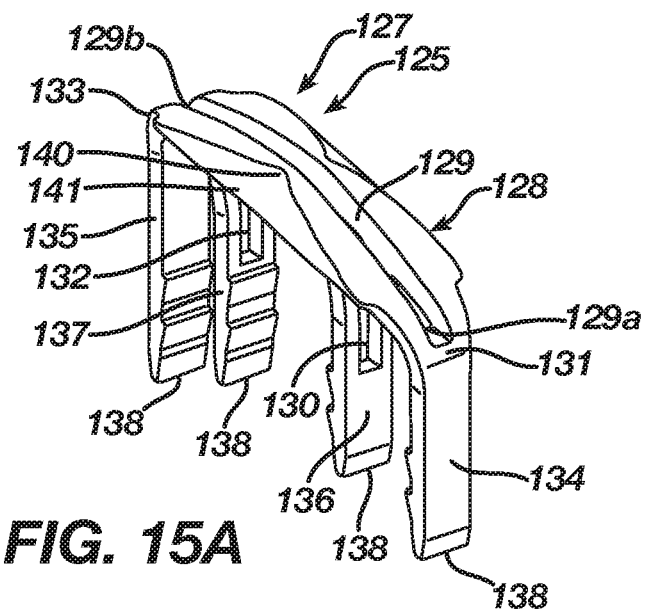
FIG. 15A is an isometric view illustrating the shape memory implant according to the third embodiment in an insertion shape.
Figure 15B:
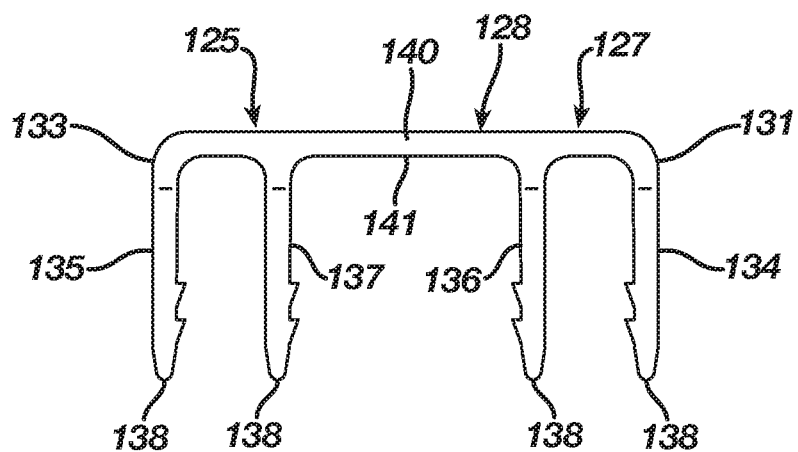
FIG. 15B is a side view thereof.

FIGS. 14A-14B illustrate an orthopedic implant 125 according to a third embodiment in a natural shape 126, whereas FIGS. 15A-15B illustrate the orthopedic implant 125 in an insertion shape 127. The implant 125 in the third embodiment may be manufactured from a shape memory material with superelastic or temperature dependent properties (e.g., Nitinol) such that the implant 125 transitions between its natural shape 126 and its insertion shape 127. The implant 125 when deformed from its natural shape 126 to its insertion shape 127 stores energy deliverable to the bone, bones, or bone pieces. In accordance with its manufacture from shape memory material, the implant 125 begins in its natural shape 126, is transitionable to its insertion shape 127, and, once implanted in bone, bones, or bone pieces, attempts to transition from its insertion shape 127 to its natural shape 126 whereby the implant 125 delivers the energy stored therein to the bone, bones, or bone pieces in order to affix the bone, bones, or bone pieces and promote a healing thereof. In the third embodiment, attempted transition of the implant 125 from its insertion shape 127 to its natural shape 126 continuously compresses the bone, bones, or bone pieces to promote fusion thereof.

The implant 125 in the third embodiment includes a bridge 128 defining a slot 129 with an end 129*a* at an end 131 of the bridge 128 and an end 129*b* at an end 133 of the bridge 128 and a transition section 140 located at a center section 141 of the implant 125 and thus the bridge 128. The implant 125 in the third embodiment includes an anchoring member in the form of a leg 134 extending from the bridge 128 at its end 131 adjacent the end 129*a* of the slot 129 and an anchoring member in the form of a leg 135 extending from the bridge 128 at its end 133 adjacent the end 129*b* of the slot 129. The implant 125 in the third embodiment includes an anchoring member in the form of a leg 136 extending from the bridge 108 interior of the leg 134 and an anchoring member in the form of a leg 137 extending from the bridge 108 interior of the leg 135. In the third embodiment, the leg 136 includes a passage 130 and the leg 137 includes the passage 132 whereby the passages 130 and 132 permit engagement of the blade 60 for the implant insertion device 50 with the legs 134 and 135. The legs 134-137 in the third embodiment are formed integrally with the bridge 128. Each leg 134-137, which has a respective tip 138, may include barbs thereon that improve the pull-out resistance of the implant 125. The implant 125 includes anchoring members in the form of legs 134-137 in order to facilitate a securing of the implant 125 with bone, bones, or bone pieces whereby the bridge 128 between the legs 134 and 137 traverses a fixation zone of the bone, bones, or bone pieces such that the implant 125, after its insertion and attempted transition from the insertion shape 127 to the natural shape 126, delivers energy to the bone, bones, or bone pieces at the fixation zone.

The regular inherent shape of the implant 125, as illustrated in FIGS. 14A-14B, is its natural shape 126 where the transition section 140 locates the bridge 128 in a natural form consisting of a closed or angular profile whereby the ends 131 and 133 reside at a first distance and the legs 134-137 reside in a natural position whereby the legs 136 and 137 are convergent and spaced apart at a first distance and the legs 134 and 135 are convergent and spaced apart at a first distance. Nevertheless, as illustrated in FIGS. 15A-15B, the implant 125 is deformable under the action of superelasticity or temperature dependent shape memory to an insertion shape 127 where the transition section 140 deforms to store energy while also moving the bridge 128 from its natural form to an insertion form which is an open or substantially linear profile whereby the ends 131 and 133 reside at a second distance that is greater than the first distance and the legs 134-137 reside in an insertion position whereby the legs 136 and 137 are substantially parallel and spaced apart at a second distance that is greater than the first distance and the legs 134 and 135 are substantially parallel and spaced apart at a second distance that is greater than the first distance. Since the insertion shape 127 is not the regular inherent shape of the implant 125, the bridge 128 typically is mechanically constrained using the implant insertion device 50 whereby the implant insertion device 50 maintains the bridge 128 in its insertion form. In order to facilitate engagement of an implant insertion device 50 with the implant 125, the bridge 128 includes the slot 129 that receives the implant insertion device 50 therethrough such that the implant insertion device 50 engages the bridge 128 at each end 129a and 129b of the slot 129. In particular, the implant insertion device 50 passes through the slot 129 and engages the bridge 128 where the bridge 128 adjoins the legs 134 and 135 thereby constraining the bridge 128 deformed at the transition section 140 to maintain the implant 125 in its insertion shape 127. The implant insertion device 50 of the present invention accordingly passes through the slot 129 whereby the implant insertion device 50 is sized to engage the bridge 128 at each end 129a and 129b of the slot 129 adjacent the legs 134 and 135. While the implant insertion device 50 engages the bridge 128 adjacent the legs 134 and 135, the implant insertion device 50 may extend beyond the bridge 128 and into the passages 130 and 132 of the legs 136 and 137 to engage the legs 134 and 135 to increase surface area contact between the implant insertion device 50 and the implant 125. After implantation into bone, bones, or bone pieces and a release of the implant insertion device 50, including if necessary a heating of the implant 125, the implant 125 delivers the energy stored in the transition section 140 such that the bridge 128 attempts to transition from its open insertion form to its closed natural form, resulting in the legs 134-137 attempting to move from their insertion position to their natural position whereby the implant 125 affixes the bone, bones, or bone pieces through an application of a compressive force thereto.

When receiving the implant 125 in an orthopedic fixation system, the implant insertion device 50 begins in its unloaded position 51 wherein the implant grip 54 resides in its disengaged position 55. The implant 125 is mechanically deformed from its natural shape 126 to its insertion shape 127 as illustrated in FIGS. 15A-15B such that the implant 125 stores mechanical energy. Mechanical deformation of the implant 125 may include cooling of the implant 125 such that the implant 125 transitions from its austenite phase to its martensite phase prior to loading of the implant 125 on the implant insertion device 50. After deformation of the implant 125, the implant insertion device 50 is positioned adjacent the deformed implant 125 whereby the tamp 79 of the body 53 contacts the bridge 128 while the channel exit 83 of the body 53 aligns with the slot 129 defined by the bridge 128; and, in particular, the first tamp section 79a and the second tamp section 79b contact the bridge 128 on opposite sides of the slot 129.

Figure 16A:
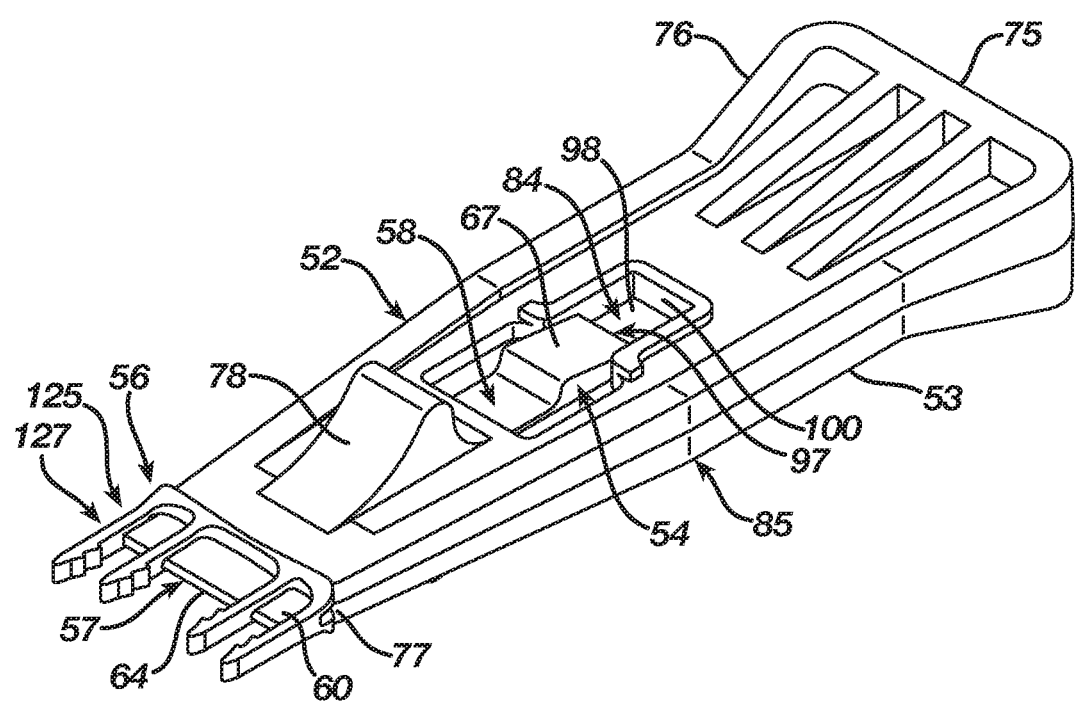
FIG. 16A is an isometric view illustrating the implant insertion device in its loaded position retaining a shape memory implant according to the third embodiment in its insertion shape.
Figure 16B:
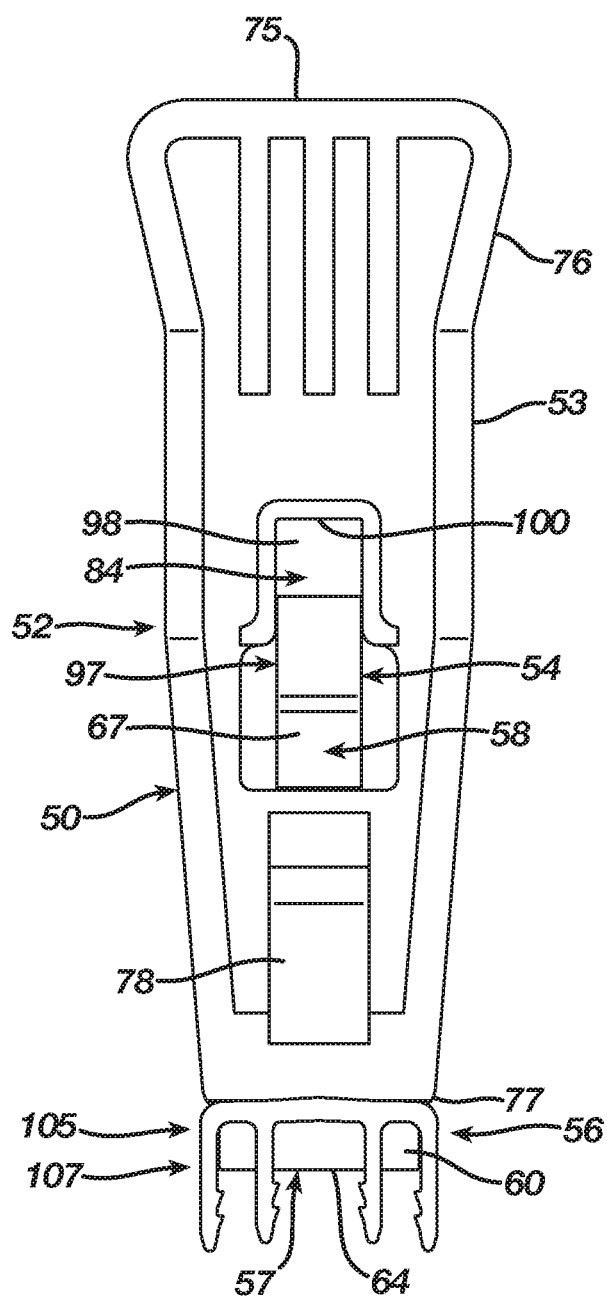
FIG. 16B is a front view illustrating the implant insertion device in its loaded position retaining a shape memory implant according to the third embodiment in its insertion shape.

Once the body 53 of the implant insertion device 50 aligns with the bridge 128 of the implant 125, a force applied to the actuator 58 progresses the actuator 58 along the body 53 towards the stop 96 of the body 53 until the actuator 58 at the first ends 90 contacts the stop 96 such that the actuator 58 via the shaft 59 advances the blade 60 beginning at its leading edge 64 through the channel exit 83 and exterior to the body 53 such that the blade 60 inserts through the slot 129 while its first and second sides 65 and 66 respectively abut the bridge 128 at the ends 129a and 129b of the slot 129 thereby engaging the bridge 128 and constraining the implant 125 in its insertion shape 127 as illustrated in FIGS. 16A-16B. The blade 60 accordingly passes through the slot 129 such that its first and second sides 65 and 66 respectively engage the bridge 128 at the ends 129a and 129b of the slot 129 as well as at the bridge 128 where the bridge 128 adjoins the legs 134 and 135 thereby constraining the bridge 128 and the deformed transition section 140 to maintain the implant 125 in its insertion shape 127. The blade 60 in the preferred embodiment further may extend beyond the bridge 128 and into the passages 130 and 132 of the legs 136 and 137 whereby its first and second sides 65 and 66 respectively engage the legs 134 and 135 to increase surface area contact between the blade 60 and the implant 125.

While the implant 125 may be mechanically deformed from its natural shape 126 to its insertion shape 127 prior to its loading on the implant insertion device 50, the implant insertion device 50 may be employed during its loading with the implant 125 to mechanically deform the implant 125 from its natural shape 126 and to its insertion shape 127. The implant insertion device 50 is positioned adjacent the implant 125 in its natural shape 126 whereby the tamp 79 of the body 53 contacts the bridge 128 while the channel exit 83 of the body 53 aligns with the slot 129 defined by the bridge 128; and, in particular, the first tamp section 79a and the second tamp section 79b contact the bridge 128 on opposite sides of the slot 129. Once the body 53 of the implant insertion device 50 aligns with the bridge 128 of the implant 125, a force applied to the actuator 58 progresses the actuator 58 along the body 53 towards the stop 96 of the body 53 until the actuator 58 at the first ends 90 contacts the stop 96 whereby the actuator 58 via the shaft 59 advances the blade 60 beginning at its leading edge 64 through the channel exit 83 and exterior to the body 53. The blade 60 inserts through the slot 129 while its first and second sides 65 and 66 respectively abut the bridge 128 at the ends 129a and 129b of the slot 129 such that the blade 60 due to the force imparted thereto by the actuator 58 deforms the bridge 128 thereby transitioning the implant 125 from its natural shape 126 to its insertion shape 127 and constraining the implant 125 as illustrated in FIGS. 16A-16B. The blade 60 accordingly passes through the slot 129 while its first and second sides 65 and 66 respectively engage the bridge 128 at the ends 129a and 129b of the slot 129 as well as at the bridge 128 where the bridge 128 adjoins the legs 134 and 135 such that the blade 60 due to the force imparted thereto by the actuator 58 deforms transition section 140 thereby transitioning the implant 125 from its natural shape 126 to its insertion shape 127. The blade 60 in the preferred embodiment further may extend beyond the bridge 128 and into the passages 130 and 132 of the legs 136 and 137 whereby its first and second sides 65 and 66 respectively engage the legs 134 and 135 to increase surface area contact between the blade 60 and the implant 125.

When delivering the implant 125 to bone, bones, or bone pieces, the implant insertion device 50 as illustrated in FIGS. 16-16B begins in its loaded position 52 wherein the implant grip 54 in its engaged position 56 constrains the implant 125 in its insertion shape 127. In order to release the implant 125 from the implant insertion device 50, a force applied to the implant grip 54 either at the leading edge 64 of the blade 60 as described herein or the actuator 58 progresses the implant grip 54 from its engaged position 56 to its disengaged position 55. The implant grip 54 exits from the slot 129 defined by the bridge 128 and retracts into the body 53 via the channel exit 83 such that the implant grip 54 releases the bridge 128 at respective ends 129a and 129b of the slot 129 resulting in an attempted transition of the implant 125 from its insertion shape 127 to its natural shape 126 whereby the implant 125 delivers the energy stored therein to the bone, bones, or bone pieces. More particularly, progression of the actuator 58 along the body 53 to the stop 100 thereof moves the blade 60 via the shaft 59 such that the blade 60 exits from the slot 129 defined by the bridge 128 and retracts into the body 53 via the channel exit 83. The blade 60 at its first and second ends 65 and 66 releases the bridge 128 at respective ends 129a and 129b of the slot 129 thereby allowing an attempted transition of the implant 125 from its insertion shape 127 to its natural shape 126. The blade 60 accordingly releases the bridge 128 where the bridge 128 adjoins the legs 134 and 135 as well as the bridge 128 at the ends 129a and 129b of the slot 129. The blade 60 further disengages from the legs 134 and 135 when the blade 60 extends beyond the bridge 128 and into the passages 130 and 132 of the legs 136 and 137 such that the blade 60 abuts the legs 134 and 135 in order to increase surface area contact between the blade 60 and the implant 125.

Figure 17A:
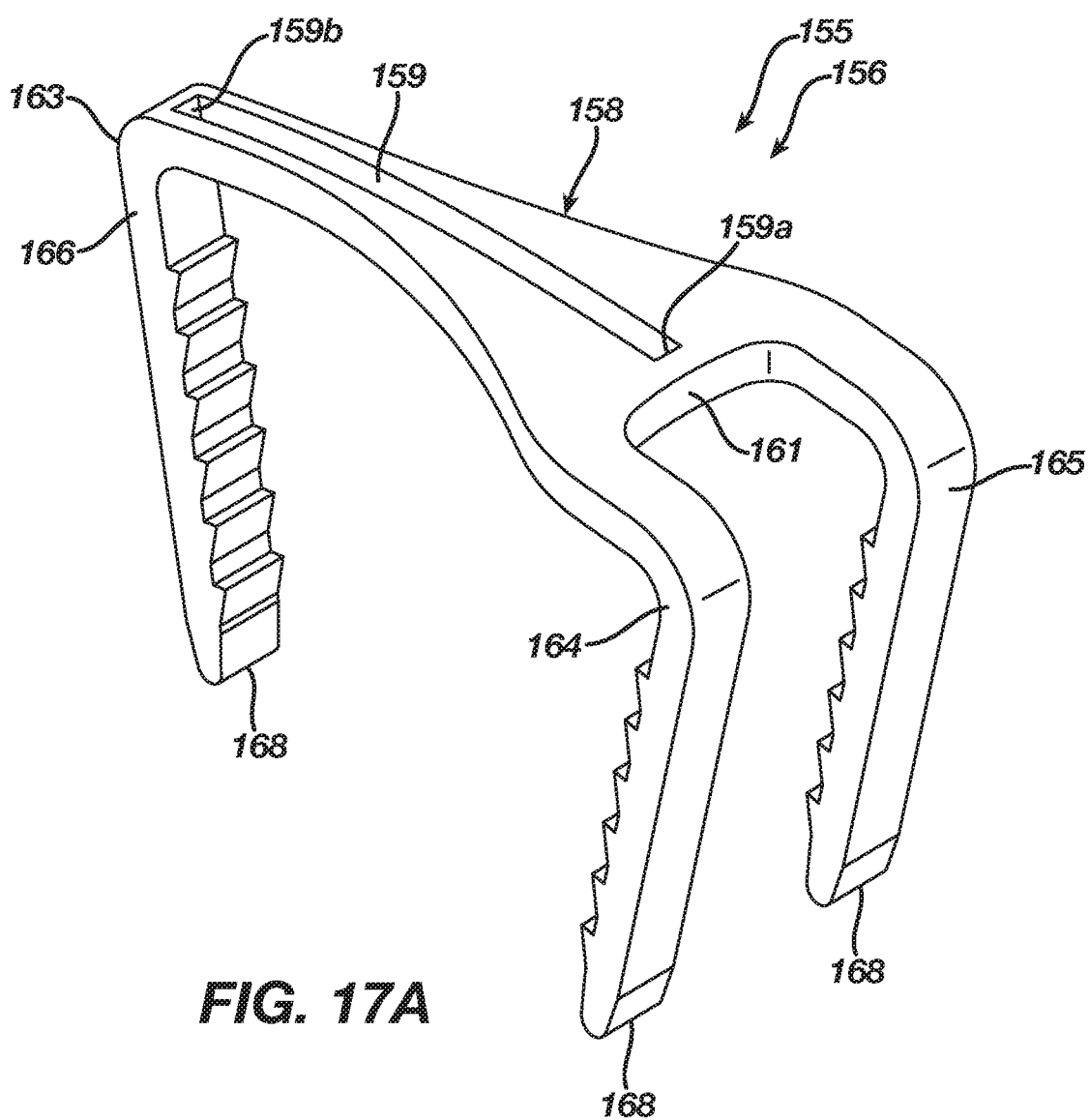
FIG. 17A is an isometric view illustrating a shape memory implant according to a fourth embodiment in a natural shape.
Figure 17B:
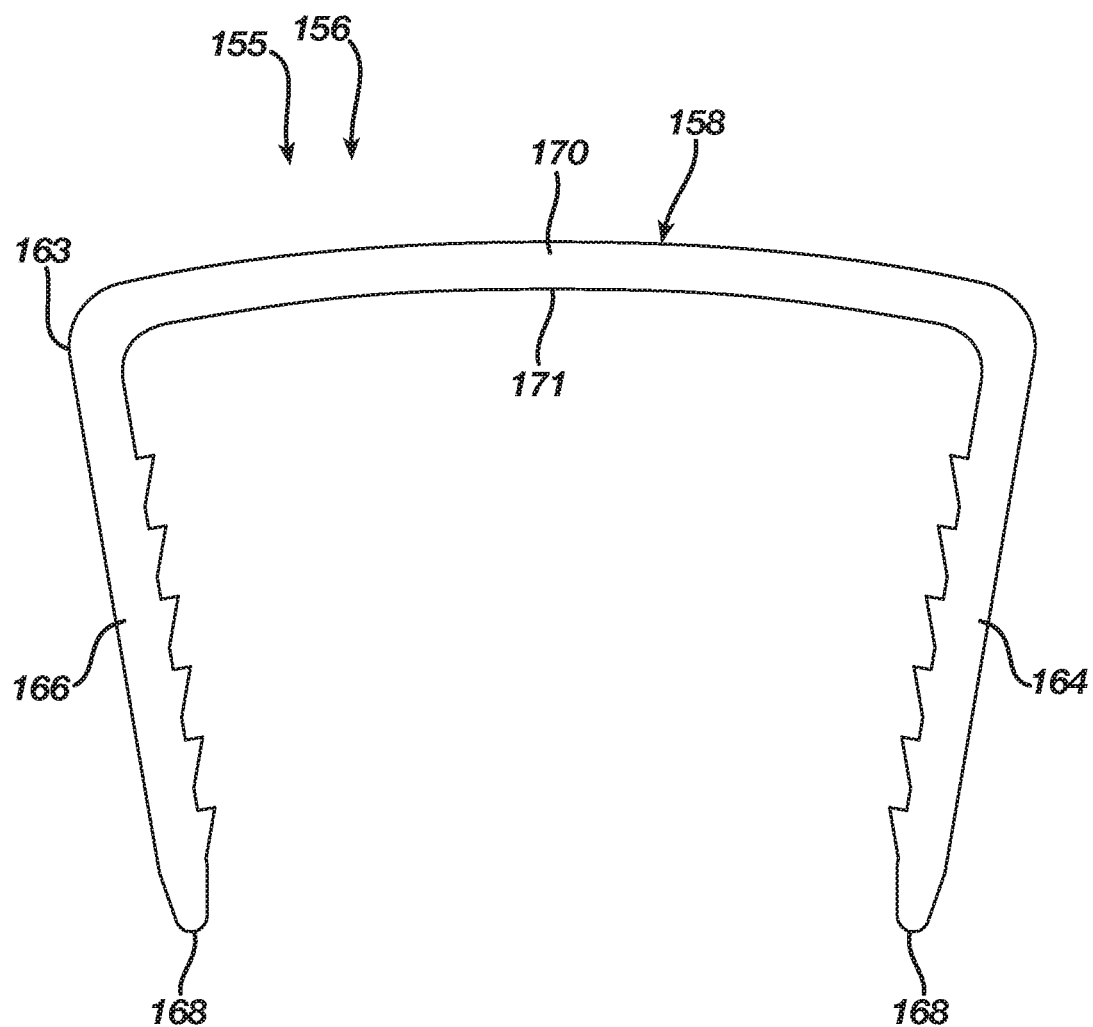
FIG. 17B is a side view thereof.

FIGS. 17A-17B illustrate an orthopedic implant 155 according to a fourth embodiment in a natural shape 156, whereas FIGS. 17A-17B illustrate the orthopedic implant 155 in an insertion shape 157. The implant 155 in the fourth embodiment may be manufactured from a shape memory material with superelastic or temperature dependent properties (e.g., Nitinol) such that the implant 155 transitions between its natural shape 156 and its insertion shape 157. The implant 155 when deformed from its natural shape 156 to its insertion shape 157 stores energy deliverable to bone, bones, or bone pieces. In accordance with its manufacture from shape memory material, the implant 155 begins in its natural shape 156, is transitionable to its insertion shape 157, and, once implanted in bone, bones, or bone pieces, attempts to transition from its insertion shape 157 to its natural shape 156 whereby the implant 155 delivers the energy stored therein to the bone, bones, or bone pieces in order to affix the bone, bones, or bone pieces and promote a healing thereof. In the fourth embodiment, attempted transition of the implant 155 from its insertion shape 157 to its natural shape 156 continuously compresses the bone, bones, or bone pieces to promote fusion thereof.

The implant 155 in the fourth embodiment includes a bridge 158 defining a slot 159 with an end 159a at an end 161 of the bridge 158 and an end 159b at an end 163 of the bridge 158 and a transition section 170 located at a center section 171 of the implant 155 but offset towards the end 161 of the bridge 158. The implant 155 in the fourth embodiment includes an anchoring member in the form of a leg 164 extending from the bridge 158 at its end 161 offset from the end 159a of the slot 159, an anchoring member in the form of a leg 165 located adjacent the leg 164 and extending from the bridge 158 at its end 161 offset from the end 159a of the slot 159, and an anchoring member in the form of a leg 166 extending from the bridge 158 at its end 163 adjacent the end 159b of the slot 159. The legs 164-166 in the fourth embodiment are formed integrally with the bridge 158. Each leg 164-166, which has a respective tip 168, may include barbs thereon that improve the pull-out resistance of the implant 155. The implant 155 includes anchoring members in the form of legs 164-166 in order to facilitate a securing of the implant 155 with bone, bones, or bone pieces whereby the bridge 158 between the legs 164-165 and the leg 166 traverses a fixation zone of the bone, bones, or bone pieces such that the implant 155, after its insertion and attempted transition from the insertion shape 157 to the natural shape 156, delivers energy to the bone, bones, or bone pieces at the fixation zone.

Figure 18A:
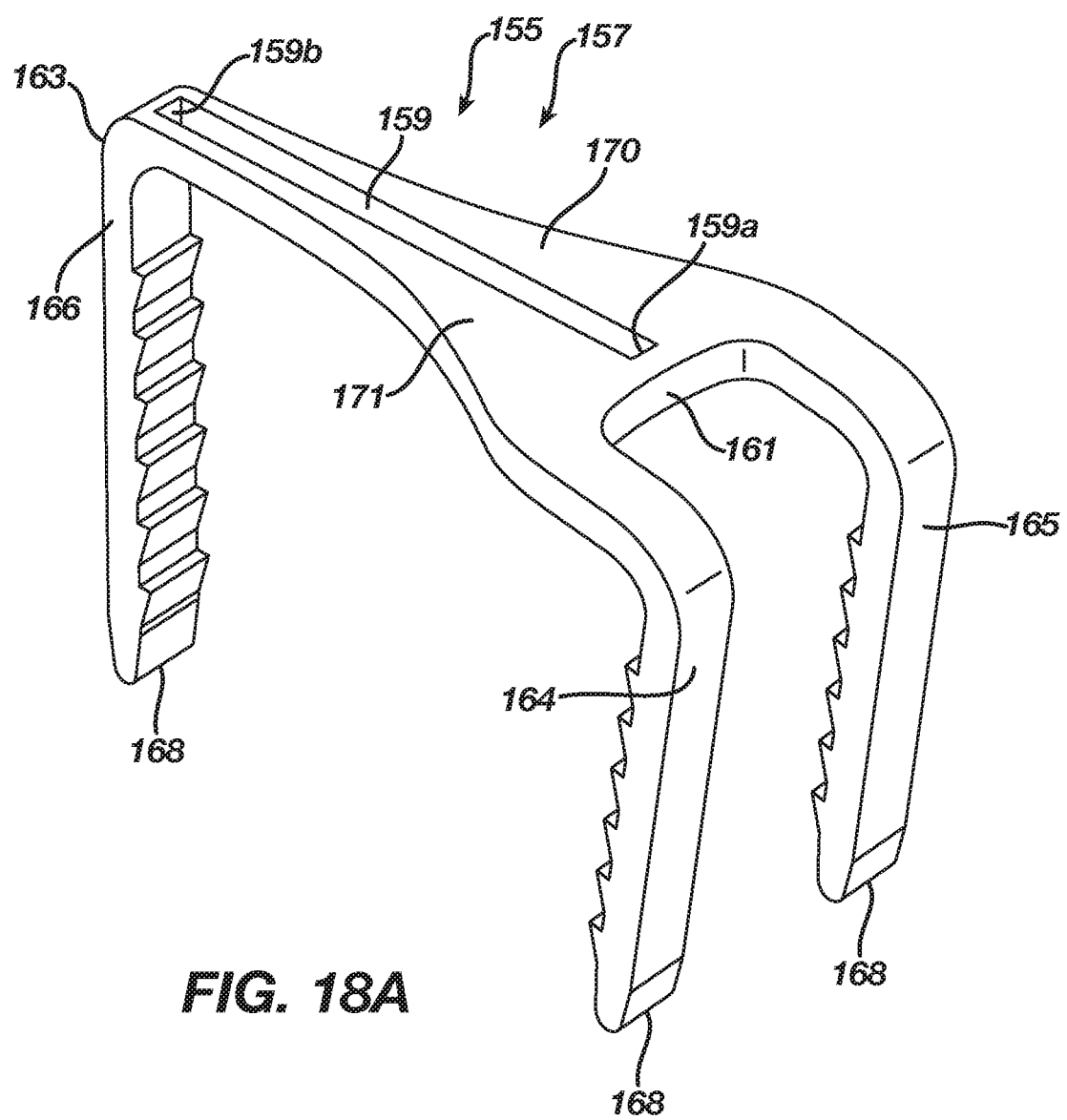
FIG. 18A is an isometric view illustrating the shape memory implant according to the fourth embodiment in an insertion shape.
Figure 18B:
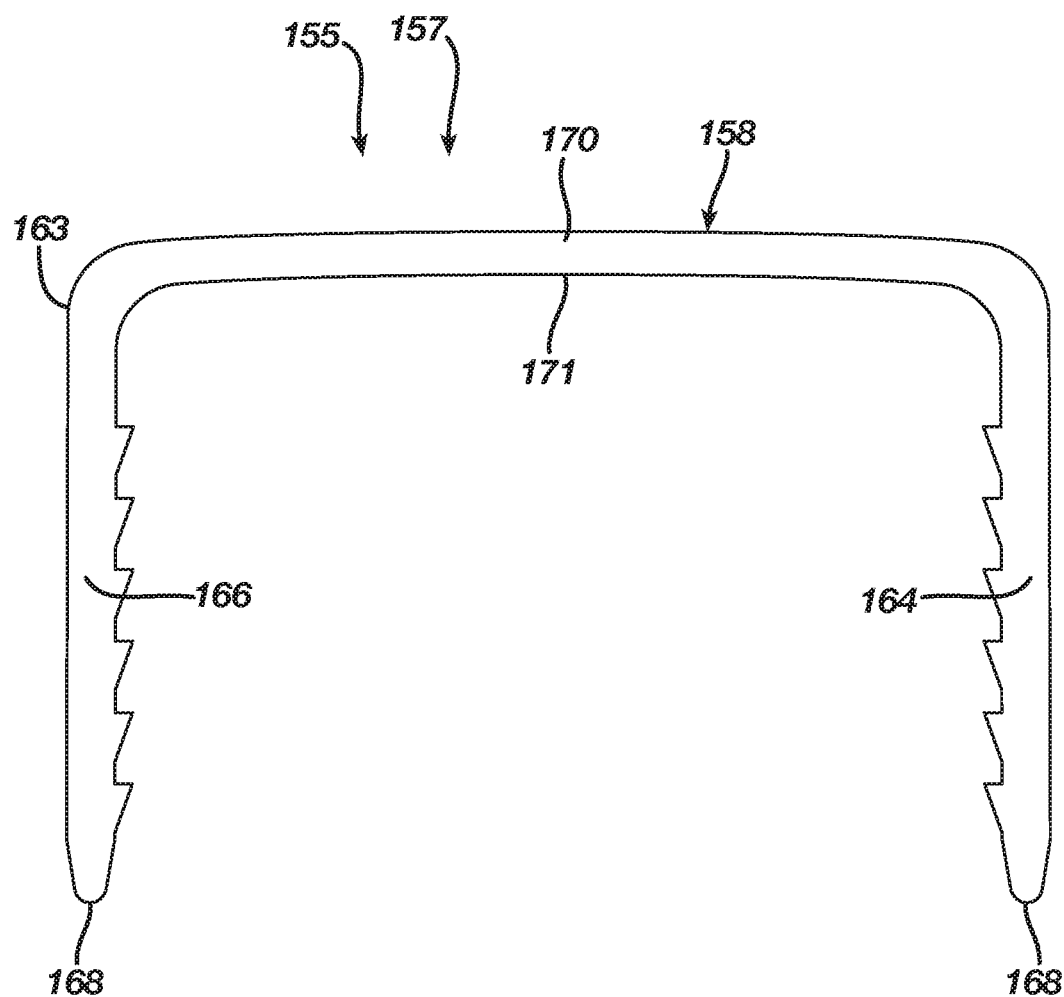
FIG. 18B is a side view thereof.

The regular inherent shape of the implant 155, as illustrated in FIGS. 17A-17B, is its natural shape 156 where the transition section 170 locates the bridge 158 in a natural form consisting of a closed or angular profile whereby the ends 161 and 163 reside at a first distance and the legs 164-165 and the leg 166 reside in a natural position whereby the legs 164-165 and the leg 166 are convergent and spaced apart at a first distance. Nevertheless, as illustrated in FIGS. 18A-18B, the implant 155 is deformable under the action of superelasticity or temperature dependent shape memory to an insertion shape 157 where the transition section 170 deforms to store energy while also moving the bridge 158 from its natural form to an insertion form which is an open or substantially linear profile whereby the ends 161 and 163 reside at a second distance that is greater than the first distance and the legs 164-166 reside in an insertion position whereby the legs 164-165 and the leg 166 are substantially parallel and spaced apart at a second distance that is greater than the first distance. Since the insertion shape 157 is not the regular inherent shape of the implant 155, the bridge 158 typically is mechanically constrained using the implant insertion device 50 whereby the implant insertion device 50 maintains the bridge 158 in its insertion form. In order to facilitate engagement of an implant insertion device 50 with the implant 155, the bridge 158 includes the slot 159 that receives the implant insertion device 50 therethrough such that the implant insertion device 50 engages the bridge 158 at each end 159a and 159b of the slot 159. In particular, the implant insertion device 50 passes through the slot 159 and engages the bridge 158 where the bridge 158 adjoins the leg 166 thereby constraining the bridge 158 deformed at the transition section 170 to maintain the implant 155 in its insertion shape 157. The implant insertion device 50 of the present invention accordingly passes through the slot 159 whereby the implant insertion device 50 is sized to engage the bridge 158 at each end 159a and 159b of the slot 159 adjacent the legs 164-165 and 166. While the implant insertion device 50 engages the bridge 158 adjacent the legs 164-165 and 166, the implant insertion device 50 may extend beyond the bridge 158 and engage the leg 165 to increase surface area contact between the implant insertion device 50 and the implant 155. After implantation into bone, bones, or bone pieces and a release of the implant insertion device 50, including if necessary a heating of the implant 155, the implant 155 delivers the energy stored in the transition section 170 such that the bridge 158 attempts to transition from its open insertion form to its closed natural form, resulting in the legs 164-165 and 166 attempting to move from their insertion position to their natural position whereby the implant 155 affixes the bone, bones, or bone pieces through an application of a compressive force thereto.

When receiving the implant 155 in an orthopedic fixation system, the implant insertion device 50 begins in its unloaded position 51 wherein the implant grip 54 resides in its disengaged position 55. The implant 155 is mechanically deformed from its natural shape 156 to its insertion shape 157 as illustrated in FIGS. 18A-18B such that the implant 155 stores mechanical energy. Mechanical deformation of the implant 155 may include cooling of the implant 155 such that the implant 155 transitions from its austenite phase to its martensite phase prior to loading of the implant 155 on the implant insertion device 50. After deformation of the implant 155, the implant insertion device 50 is positioned adjacent the deformed implant 155 whereby the tamp 79 of the body 53 contacts the bridge 158 while the channel exit 83 of the body 53 aligns with the slot 159 defined by the bridge 158; and, in particular, the first tamp section 79a and the second tamp section 79b contact the bridge 158 on opposite sides of the slot 159.

Figure 19A:
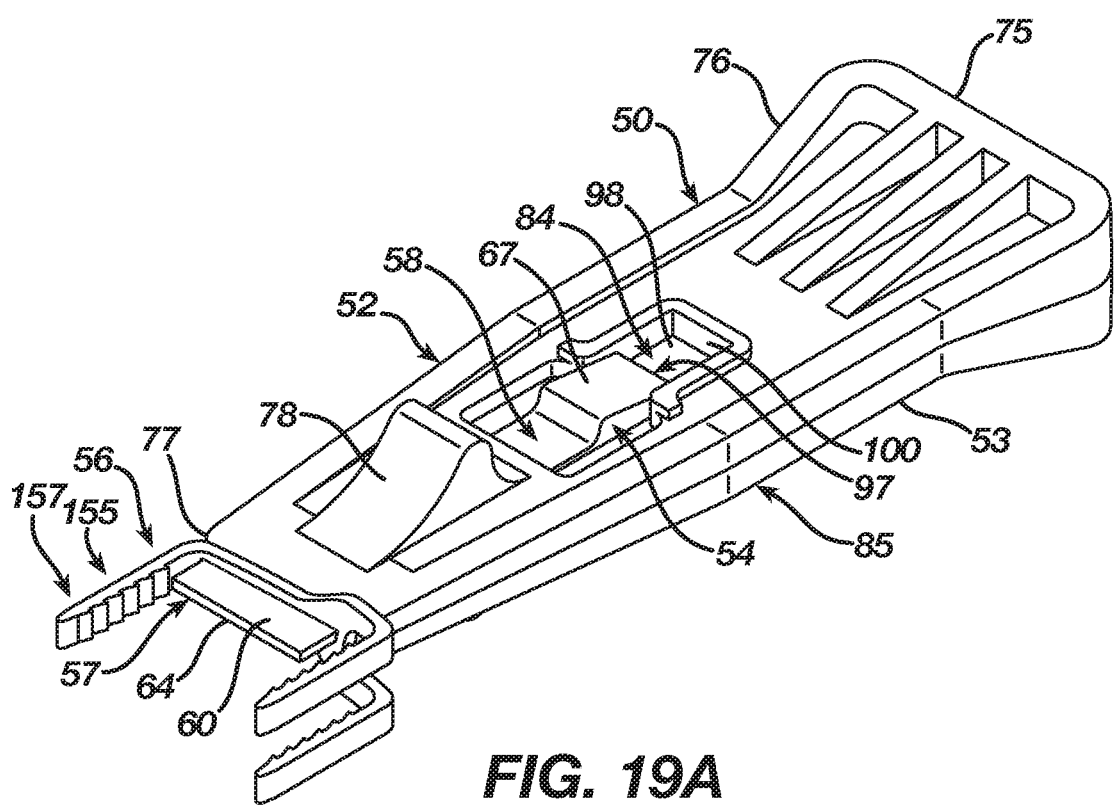
FIG. 19A is an isometric view illustrating the implant insertion device in its loaded position retaining a shape memory implant according to the fourth embodiment in its insertion shape.
Figure 19B:
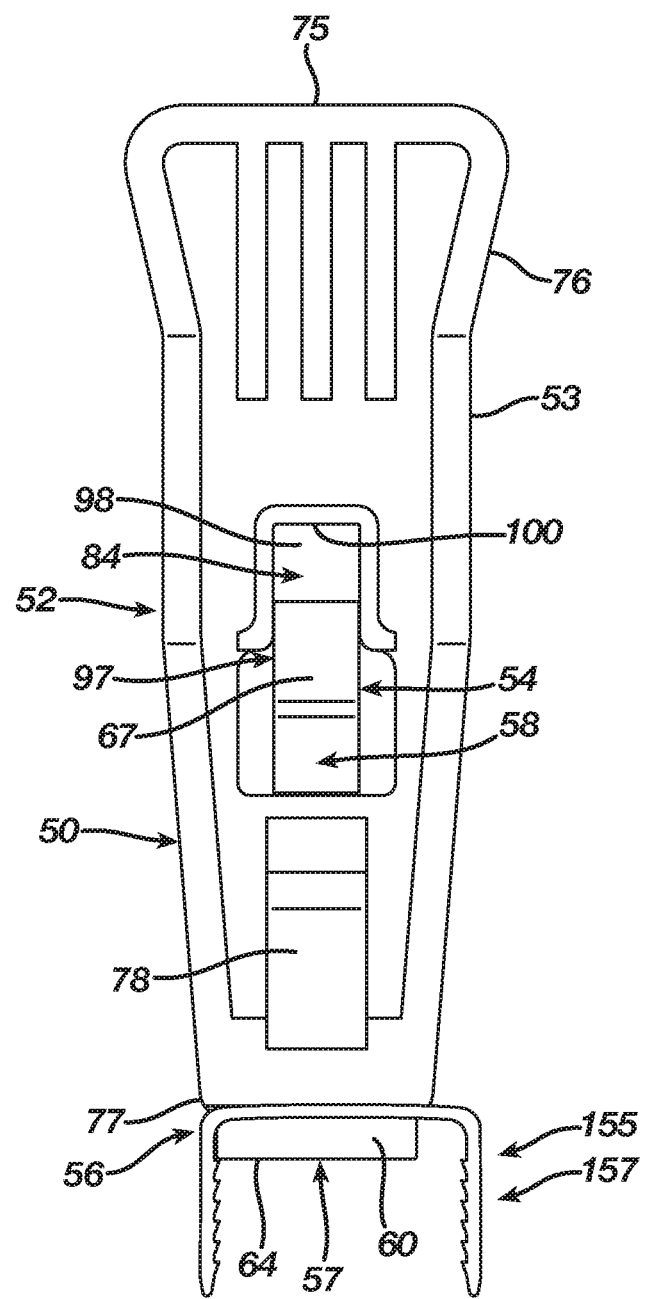
FIG. 19B is a front view illustrating the implant insertion device in its loaded position retaining a shape memory implant according to the fourth embodiment in its insertion shape.

Once the body 53 of the implant insertion device 50 aligns with the bridge 158 of the implant 155, a force applied to the actuator 58 progresses the actuator 58 along the body 53 towards the stop 96 of the body 53 until the actuator 58 at the first ends 90 contacts the stop 96 such that the actuator 58 via the shaft 59 advances the blade 60 beginning at its leading edge 64 through the channel exit 83 and exterior to the body 53 such that the blade 60 inserts through the slot 159 while its first and second sides 65 and 66 respectively abut the bridge 158 at the ends 159a and 159b of the slot 159 thereby engaging the bridge 158 and constraining the implant 155 in its insertion shape 157 as illustrated in FIGS. 19A-19B. The blade 60 accordingly passes through the slot 159 such that its first and second sides 65 and 66 respectively engage the bridge 158 at the ends 159a and 159b of the slot 159 as well as at the bridge 158 where the bridge 158 adjoins the leg 166 thereby constraining the bridge 158 and the deformed transition section 170 to maintain the implant 155 in its insertion shape 157. The blade 60 in the preferred embodiment further may extend beyond the bridge 158 whereby its second side 66 engages the leg 166 to increase surface area contact between the blade 60 and the implant 155.

While the implant 155 may be mechanically deformed from its natural shape 156 to its insertion shape 157 prior to its loading on the implant insertion device 50, the implant insertion device 50 may be employed during its loading with the implant 155 to mechanically deform the implant 155 from its natural shape 156 and to its insertion shape 157. The implant insertion device 50 is positioned adjacent the implant 155 in its natural shape 156 whereby the tamp 79 of the body 53 contacts the bridge 158 while the channel exit 83 of the body 53 aligns with the slot 159 defined by the bridge 158; and, in particular, the first tamp section 79a and the second tamp section 79b contact the bridge 158 on opposite sides of the slot 159. Once the body 53 of the implant insertion device 50 aligns with the bridge 158 of the implant 155, a force applied to the actuator 58 progresses the actuator 58 along the body 53 towards the stop 96 of the body 53 until the actuator 58 at the first ends 90 contacts the stop 96 whereby the actuator 58 via the shaft 59 advances the blade 60 beginning at its leading edge 64 through the channel exit 83 and exterior to the body 53. The blade 60 inserts through the slot 159 while its first and second sides 65 and 66 respectively abut the bridge 158 at the ends 159a and 159b of the slot 159 such that the blade 60 due to the force imparted thereto by the actuator 58 deforms the bridge 158 thereby transitioning the implant 155 from its natural shape 156 to its insertion shape 157 and constraining the implant 155 as illustrated in FIGS. 19A-19B. The blade 60 accordingly passes through the slot 159 while its first and second sides 65 and 66 respectively engage the bridge 158 at the ends 159a and 159b of the slot 159 as well as at the bridge 158 where the bridge 158 adjoins the leg 166 such that the blade 60 due to the force imparted thereto by the actuator 58 deforms transition section 170 thereby transitioning the implant 155 from its natural shape 156 to its insertion shape 157. The blade 60 in the preferred embodiment further may extend beyond the bridge 158 whereby its second side 66 engages the leg 166 to increase surface area contact between the blade 60 and the implant 155.

When delivering the implant 155 to bone, bones, or bone pieces, the implant insertion device 50 as illustrated in FIGS. 19A-19B begins in its loaded position 52 wherein the implant grip 54 in its engaged position 56 constrains the implant 155 in its insertion shape 157. In order to release the implant 155 from the implant insertion device 50, a force applied to the implant grip 54 either at the leading edge 64 of the blade 60 as described herein or the actuator 58 progresses the implant grip 54 from its engaged position 56 to its disengaged position 55. The implant grip 54 exits from the slot 159 defined by the bridge 158 and retracts into the body 53 via the channel exit 83 such that the implant grip 54 releases the bridge 158 at respective ends 159a and 159b of the slot 159 resulting in an attempted transition of the implant 155 from its insertion shape 157 to its natural shape 156 whereby the implant 155 delivers the energy stored therein to the bone, bones, or bone pieces. More particularly, progression of the actuator 58 along the body 53 to the stop 100 thereof moves the blade 60 via the shaft 59 such that the blade 60 exits from the slot 159 defined by the bridge 158 and retracts into the body 53 via the channel exit 83. The blade 60 at its first and second ends 65 and 66 releases the bridge 158 at respective ends 159a and 159b of the slot 159 thereby allowing an attempted transition of the implant 155 from its insertion shape 157 to its natural shape 156. The blade 60 accordingly releases the bridge 158 where the bridge 128 adjoins the leg 166 as well as the bridge 158 at the ends 159a and 159b of the slot 159. The blade 60 further disengages from the leg 166 when the blade 60 extends beyond the bridge 158 and to the leg 166 such that the blade 60 abuts the leg 166 in order to increase surface area contact between the blade 60 and the implant 155.

Figure 20A:
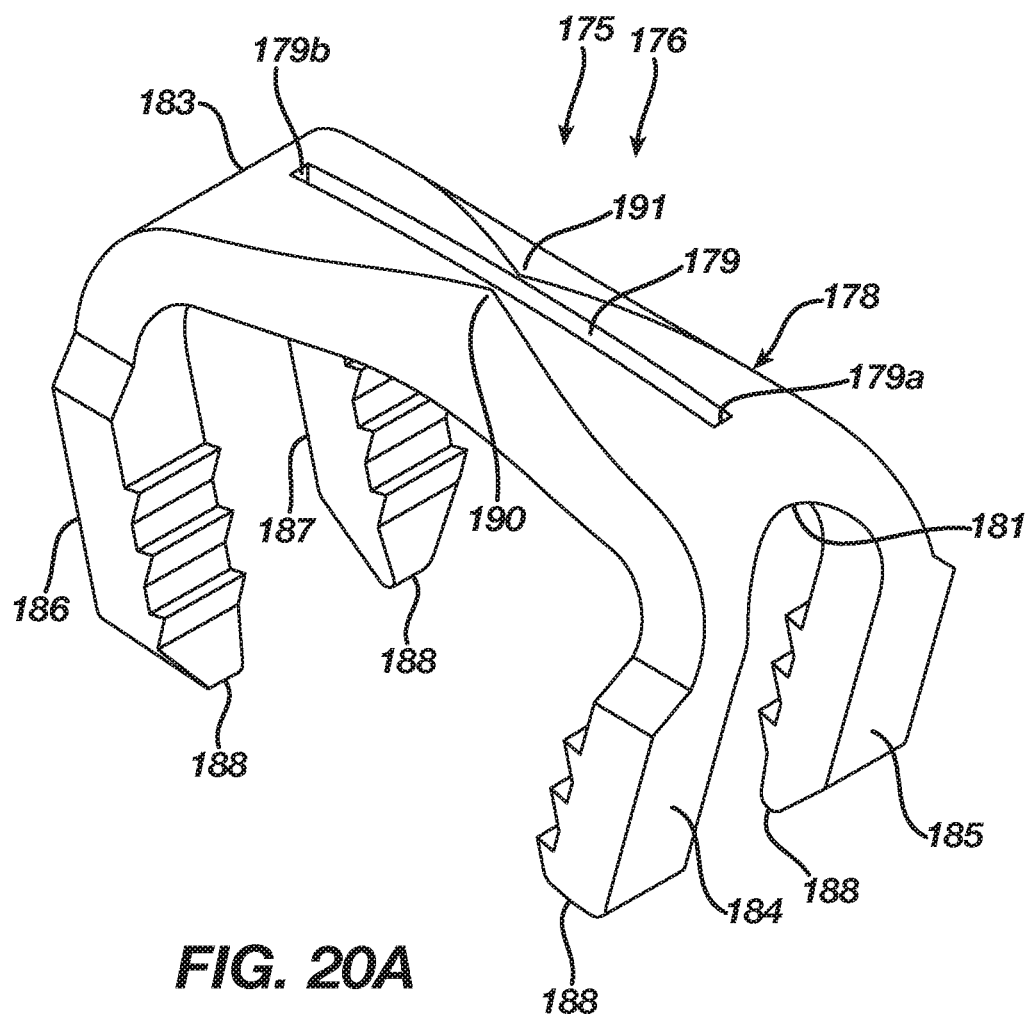
FIG. 20A is an isometric view illustrating a shape memory implant according to a fifth embodiment in a natural shape.
Figure 20B:
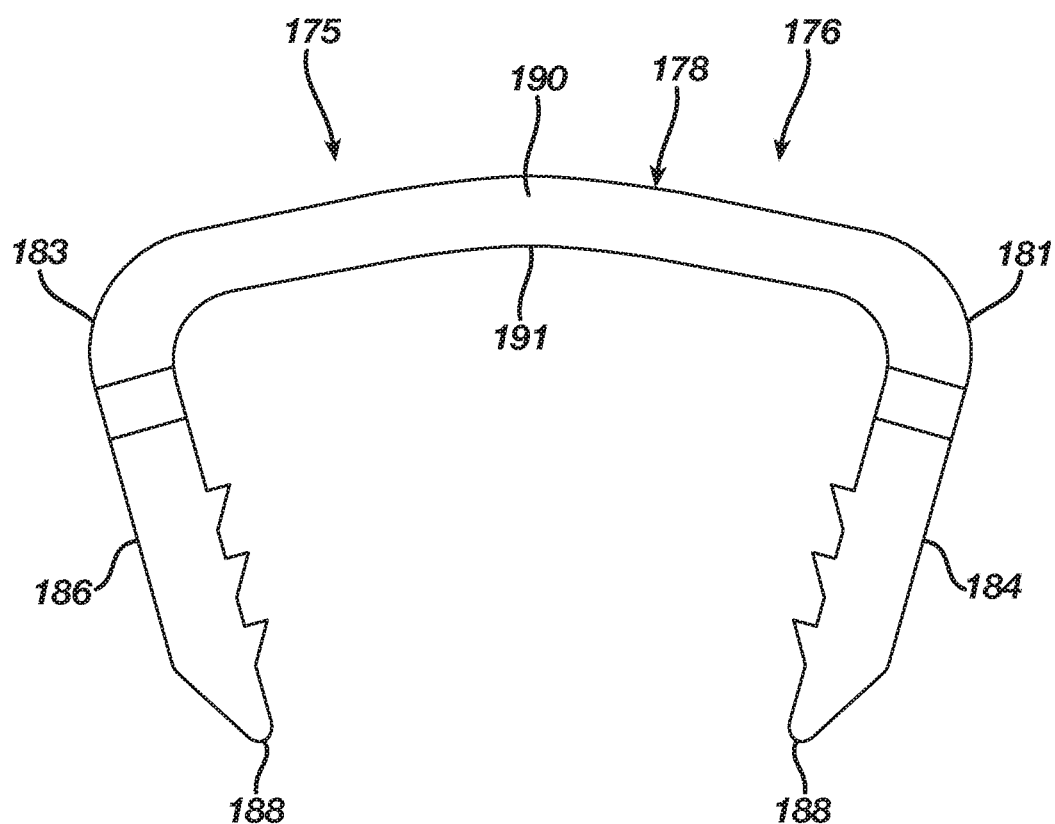
FIG. 20B is a side view thereof.
Figure 21A:
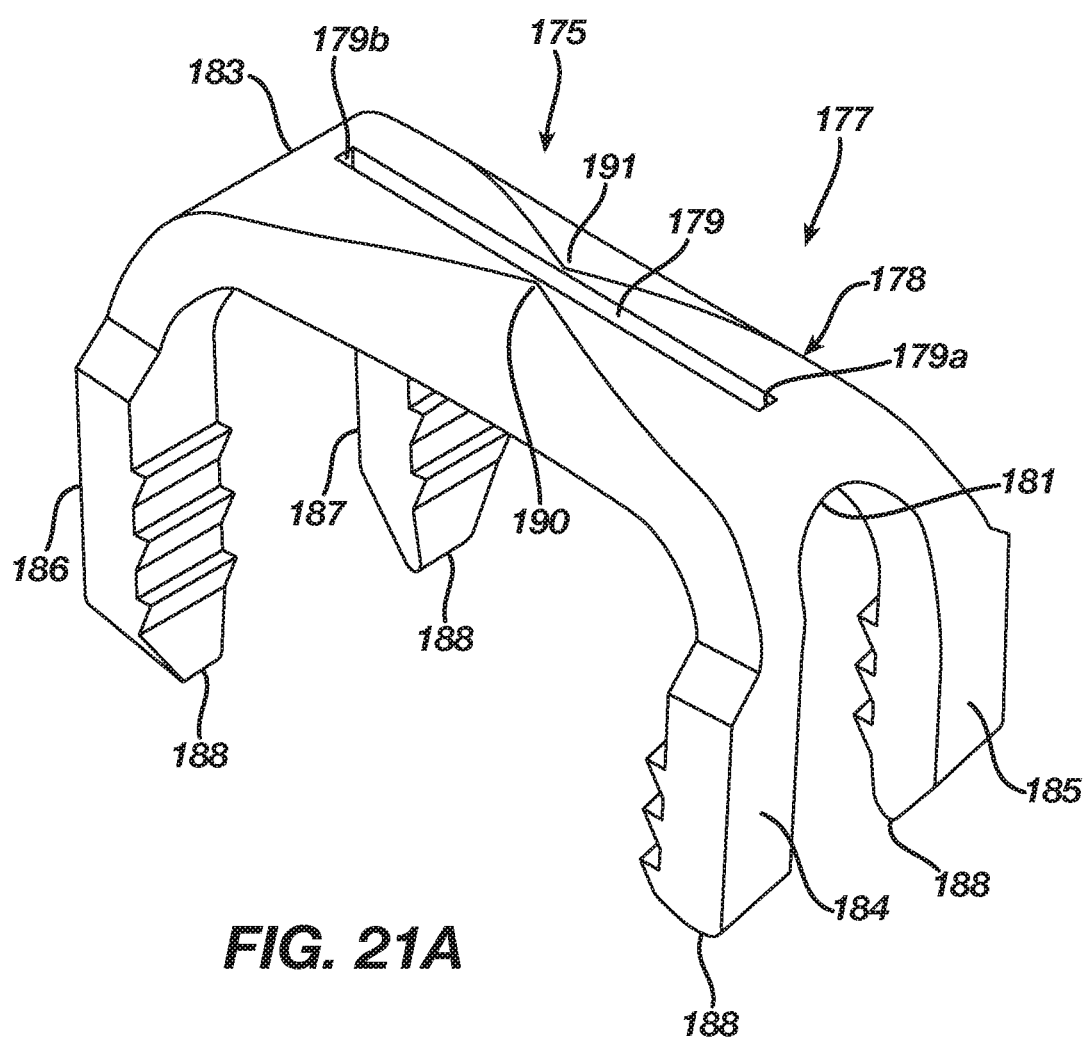
FIG. 21A is an isometric view illustrating the shape memory implant according to the fifth embodiment in an insertion shape.
Figure 21B:
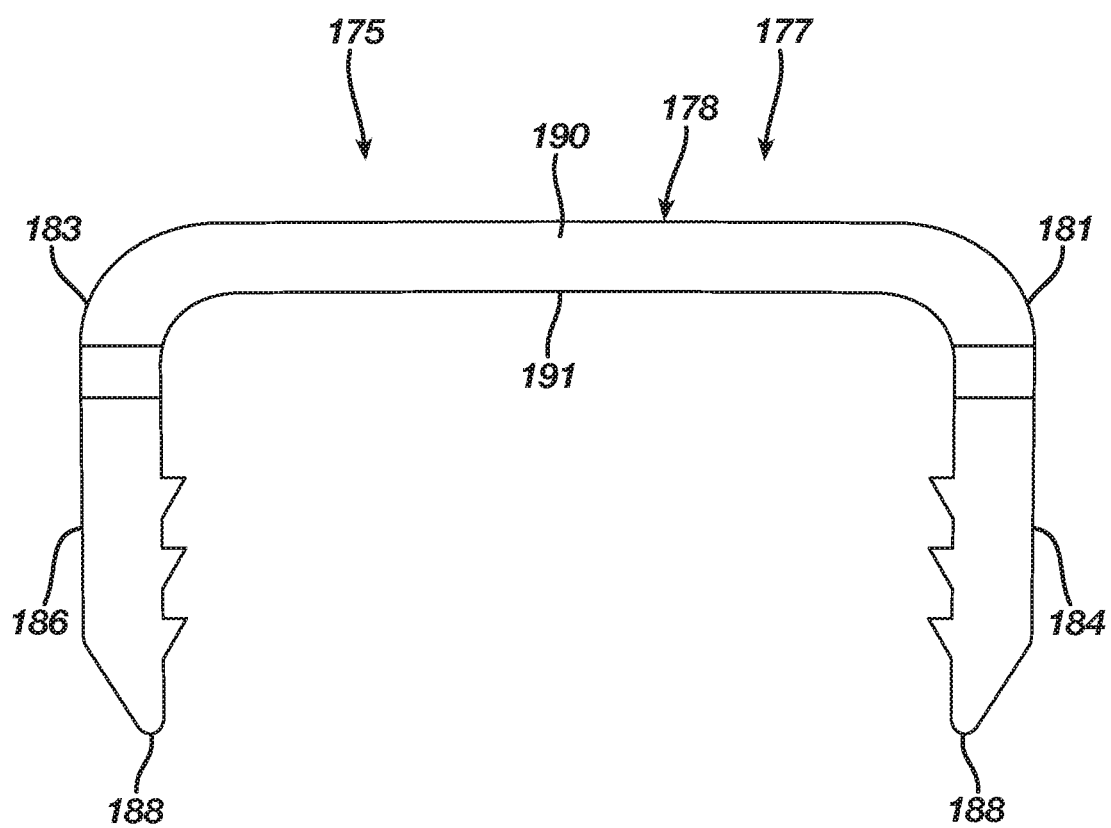
FIG. 21B is a side view thereof.

FIGS. 20A-20B illustrate an orthopedic implant 175 according to a fifth embodiment in a natural shape 176, whereas FIGS. 21A-21B illustrate the orthopedic implant 175 in an insertion shape 177. The implant 175 in the fifth embodiment may be manufactured from a shape memory material with superelastic or temperature dependent properties (e.g., Nitinol) such that the implant 175 transitions between its natural shape 176 and its insertion shape 177. The implant 175 when deformed from its natural shape 176 to its insertion shape 177 stores energy deliverable to bone, bones, or bone pieces. In accordance with its manufacture from shape memory material, the implant 175 begins in its natural shape 176, is transitionable to its insertion shape 177, and, once implanted in bone, bones, or bone pieces, attempts to transition from its insertion shape 177 to its natural shape 176 whereby the implant 175 delivers the energy stored therein to the bone, bones, or bone pieces in order to affix the bone, bones, or bone pieces and promote a healing thereof. In the fifth embodiment, attempted transition of the implant 175 from its insertion shape 177 to its natural shape 176 continuously compresses the bone, bones, or bone pieces to promote fusion thereof.

The implant 175 in the fifth embodiment includes a bridge 178 defining a slot 179 with an end 179a at an end 181 of the bridge 178 and an end 179b at an end 183 of the bridge 178 and a transition section 190 located at a center section 191 of the implant 175 and thus the bridge 178. The implant 175 in the fifth embodiment includes an anchoring member in the form of a leg 184 extending from the bridge 178 at its end 181 offset from the end 179a of the slot 179, an anchoring member in the form of a leg 185 located adjacent the leg 184 and extending from the bridge 178 at its end 181 offset from the end 179a of the slot 179, an anchoring member in the form of a leg 186 extending from the bridge 178 at its end 183 offset from the end 179b of the slot 179, and an anchoring member in the form of a leg 187 located adjacent the leg 186 and extending from the bridge 178 at its end 183 offset from the end 179b of the slot 179. The legs 184-186 in the fifth embodiment are formed integrally with the bridge 178. Each leg 184-187, which has a respective tip 188, may include barbs thereon that improve the pull-out resistance of the implant 175. The implant 175 includes anchoring members in the form of legs 184-187 in order to facilitate a securing of the implant 175 with bone, bones, or bone pieces whereby the bridge 178 between the legs 184-185 and the legs 186-187 traverses a fixation zone of the bone, bones, or bone pieces such that the implant 175, after its insertion and attempted transition from the insertion shape 177 to the natural shape 176, delivers energy to the bone, bones, or bone pieces at the fixation zone.

The regular inherent shape of the implant 175, as illustrated in FIGS. 20A-20B, is its natural shape 176 where the transition section 190 locates the bridge 178 in a natural form consisting of a closed or angular profile whereby the ends 181 and 183 reside at a first distance and the legs 184-185 and the legs 186-187 reside in a natural position whereby the legs 184-185 and the legs 186-187 are convergent and spaced apart at a first distance. Nevertheless, as illustrated in FIGS. 21A-21B, the implant 175 is deformable under the action of superelasticity or temperature dependent shape memory to an insertion shape 177 where the transition section 190 deforms to store energy while also moving the bridge 178 from its natural form to an insertion form which is an open or substantially linear profile whereby the ends 181 and 183 reside at a second distance that is greater than the first distance and the legs 184-186 reside in an insertion position whereby the legs 184-185 and the legs 186-187 are substantially parallel and spaced apart at a second distance that is greater than the first distance. Since the insertion shape 177 is not the regular inherent shape of the implant 175, the bridge 178 typically is mechanically constrained using the implant insertion device 50 whereby the implant insertion device 50 maintains the bridge 178 in its insertion form. In order to facilitate engagement of an implant insertion device 50 with the implant 175, the bridge 178 includes the slot 179 that receives the implant insertion device 50 therethrough such that the implant insertion device 50 engages the bridge 178 at each end 179a and 179b of the slot 179. In particular, the implant insertion device 50 engages the bridge 158 at each end 179a and 179b of the slot 179 and passes through the slot 179 thereby constraining the bridge 178 deformed at the transition section 190 to maintain the implant 175 in its insertion shape 177. The implant insertion device 50 of the present invention accordingly passes through the slot 179 whereby the implant insertion device 50 is sized to engage the bridge 178 at each end 179a and 179b of the slot 179 adjacent the legs 184-185 and the legs 186-187. After implantation into bone, bones, or bone pieces and a release of the implant insertion device 50, including if necessary a heating of the implant 175, the implant 175 delivers the energy stored in the transition section 190 such that the bridge 178 attempts to transition from its open insertion form to its closed natural form, resulting in the legs 184-185 and the legs 186-187 attempting to move from their insertion position to their natural position whereby the implant 175 affixes the bone, bones, or bone pieces through an application of a compressive force thereto.

When receiving the implant 175 in an orthopedic fixation system, the implant insertion device 50 begins in its unloaded position 51 wherein the implant grip 54 resides in its disengaged position 55. The implant 175 is mechanically deformed from its natural shape 176 to its insertion shape 177 as illustrated in FIGS. 21A-21B such that the implant 175 stores mechanical energy. Mechanical deformation of the implant 175 may include cooling of the implant 175 such that the implant 175 transitions from its austenite phase to its martensite phase prior to loading of the implant 175 on the implant insertion device 50. After deformation of the implant 175, the implant insertion device 50 is positioned adjacent the deformed implant 175 whereby the tamp 79 of the body 53 contacts the bridge 178 while the channel exit 83 of the body 53 aligns with the slot 179 defined by the bridge 178; and, in particular, the first tamp section 79a and the second tamp section 79b contact the bridge 178 on opposite sides of the slot 179.

Figure 22A:
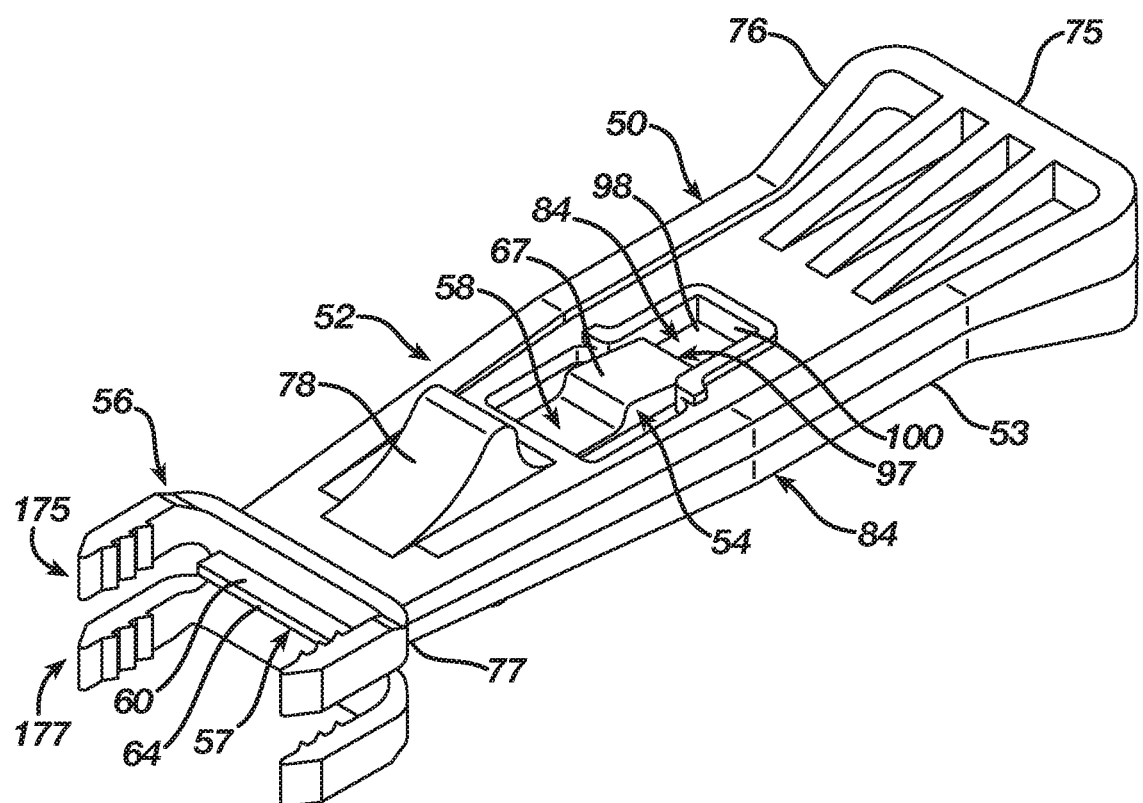
FIG. 22A is an isometric view illustrating the implant insertion device in its loaded position retaining a shape memory implant according to the fifth embodiment in its insertion shape.
Figure 22B:
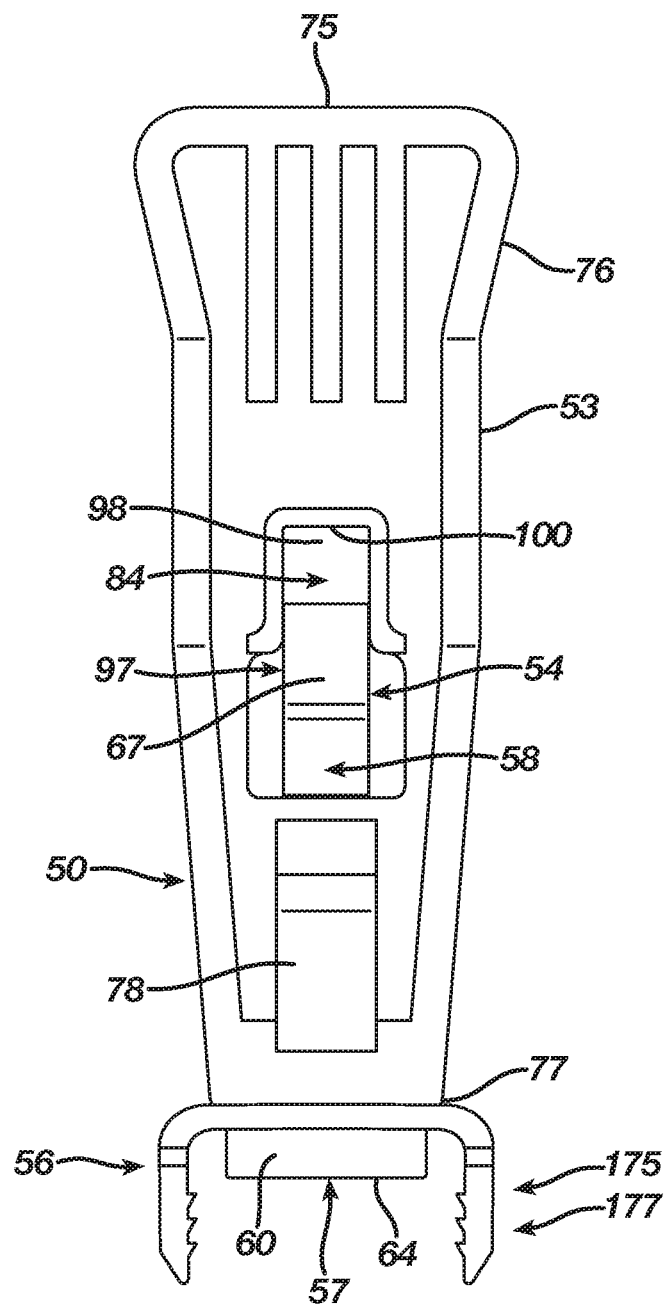
FIG. 22B is a front view illustrating the implant insertion device in its loaded position retaining a shape memory implant according to the fifth embodiment in its insertion shape.

Once the body 53 of the implant insertion device 50 aligns with the bridge 178 of the implant 175, a force applied to the actuator 58 progresses the actuator 58 along the body 53 towards the stop 96 of the body 53 until the actuator 58 at the first ends 90 contacts the stop 96 such that the actuator 58 via the shaft 59 advances the blade 60 beginning at its leading edge 64 through the channel exit 83 and exterior to the body 53 such that the blade 60 inserts through the slot 179 while its first and second sides 65 and 66 respectively abut the bridge 178 at the ends 179a and 179b of the slot 179 thereby engaging the bridge 178 and constraining the implant 175 in its insertion shape 177 as illustrated in FIGS. 22A-22B. The blade 60 accordingly at its first and second sides 65 and 66 respectively engages the bridge 178 at the ends 179a and 179b of the slot 179 and passes through the slot 179 thereby constraining the bridge 178 and the deformed transition section 190 to maintain the implant 175 in its insertion shape 177.

While the implant 175 may be mechanically deformed from its natural shape 176 to its insertion shape 177 prior to its loading on the implant insertion device 50, the implant insertion device 50 may be employed during its loading with the implant 175 to mechanically deform the implant 175 from its natural shape 176 and to its insertion shape 177. The implant insertion device 50 is positioned adjacent the implant 175 in its natural shape 176 whereby the tamp 79 of the body 53 contacts the bridge 178 while the channel exit 83 of the body 53 aligns with the slot 179 defined by the bridge 178; and, in particular, the first tamp section 79*a* and the second tamp section 79*b* contact the bridge 178 on opposite sides of the slot 179. Once the body 53 of the implant insertion device 50 aligns with the bridge 178 of the implant 175, a force applied to the actuator 58 progresses the actuator 58 along the body 53 towards the stop 96 of the body 53 until the actuator 58 at the first ends 90 contacts the stop 96 whereby the actuator 58 via the shaft 59 advances the blade 60 beginning at its leading edge 64 through the channel exit 83 and exterior to the body 53. The blade 60 inserts through the slot 179 while its first and second sides 65 and 66 respectively abut the bridge 178 at the ends 179*a* and 179*b* of the slot 179 such that the blade 60 due to the force imparted thereto by the actuator 58 deforms the bridge 178 thereby transitioning the implant 175 from its natural shape 176 to its insertion shape 177 and constraining the implant 175 as illustrated in FIGS. 22A-22B. The blade 60 accordingly at its first and second sides 65 and 66 respectively engages the bridge 178 at the ends 179*a* and 179*b* of the slot 179 and passes through the slot 179 such that the blade 60 due to the force imparted thereto by the actuator 58 deforms transition section 190 thereby transitioning the implant 175 from its natural shape 176 to its insertion shape 177.

When delivering the implant 175 to bone, bones, or bone pieces, the implant insertion device 50 as illustrated in FIGS. 22A-22B begins in its loaded position 52 wherein the implant grip 54 in its engaged position 56 constrains the implant 175 in its insertion shape 177. In order to release the implant 175 from the implant insertion device 50, a force applied to the implant grip 54 either at the leading edge 64 of the blade 60 as described herein or the actuator 58 progresses the implant grip 54 from its engaged position 56 to its disengaged position 55. The implant grip 54 exits from the slot 179 defined by the bridge 178 and retracts into the body 53 via the channel exit 83 such that the implant grip 54 releases the bridge 178 at respective ends 179*a* and 179*b* of the slot 179 resulting in an attempted transition of the implant 175 from its insertion shape 177 to its natural shape 176 whereby the implant 175 delivers the energy stored therein to the bone, bones, or bone pieces. More particularly, progression of the actuator 58 along the body 53 to the stop 100 thereof moves the blade 60 via the shaft 59 such that the blade 60 exits from the slot 179 defined by the bridge 178 and retracts into the body 53 via the channel exit 83. The blade 60 at its first and second ends 65 and 66 releases the bridge 178 at respective ends 179*a* and 179*b* of the slot 179 thereby allowing an attempted transition of the implant 175 from its insertion shape 177 to its natural shape 176.

Figure 23A:
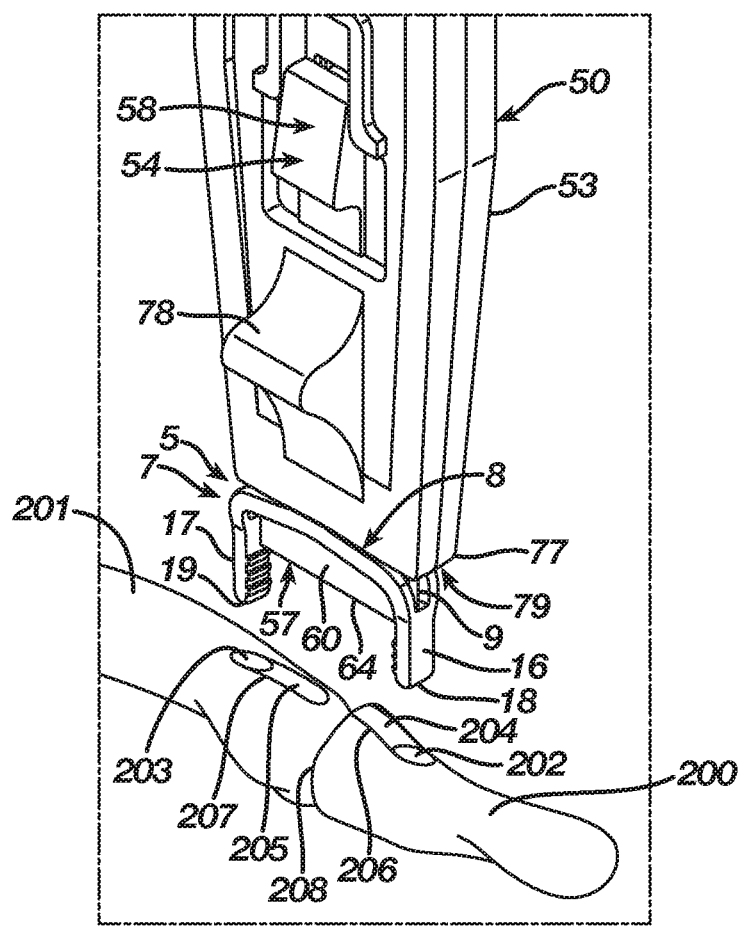
FIGS. 23A-23F are isometric views illustrating insertion of a shape memory implant according to the first embodiment into bone, bones, or bone pieces using an implant insertion device.

FIG. 23A illustrates the implant insertion device 50 with the implant 5 of the first embodiment loaded thereon in an orthopedic fixation system whereby the implant insertion device 50 retains the implant 5 in its insertion shape 7 such that the implant 5 is ready for implantation into bone, bones, or bone pieces, and, in particular, into a first bone 200 and a second bone 201, which are presented herein as an example. A surgeon as illustrated in FIG. 23A aligns the first bone 200 with the second bone 201 at a fusion zone 208 thereof and then drills a first hole 202 in the first bone 200 and a second hole 203 in the second bone 201. The holes 202 and 203 are drilled at a spacing and locations desired for insertion of the leg 16 into the first bone 200 and the leg 17 into the second bone 203 when the implant 5 resides in its insertion shape 7. While not required, the surgeon may create a first groove 204 in the first bone 200 and a second groove 205 in the second bone 201 aligned with the first groove 204 whereby the first and second grooves 204 and 205 facilitate a more flush seating of the bridge 8 for the implant 5 relative to a surface 206 of the first bone 200 and a surface 207 of the second bone 201. The surgeon next utilizes the implant insertion device 50 to position the tip 18 of the leg 16 for the implant 5 adjacent the pre-drilled hole 202 and the tip 19 of the leg 17 for the implant 5 adjacent the pre-drilled hole 203.

Figure 23B:
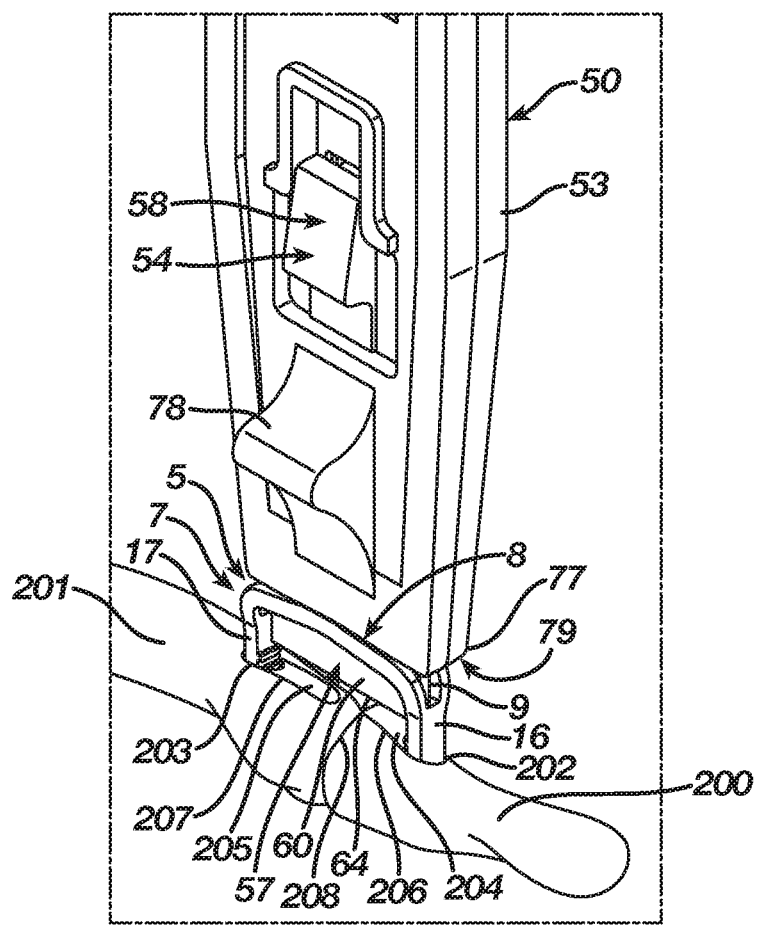
Figure 23C:
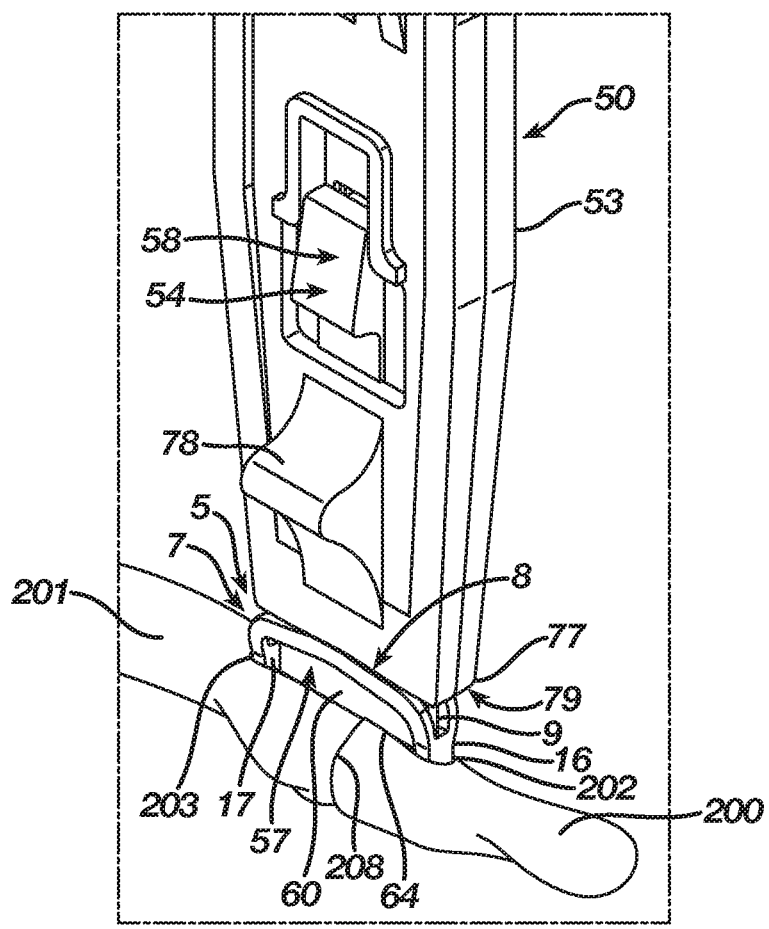

The surgeon as illustrated in FIG. 23B maneuvers the implant insertion device 50 using its body 53 whereby the legs 16 and 17 respectively enter the pre-drilled holes 202 and 203. The surgeon as illustrated in FIG. 23C manipulates the implant insertion device 50 to insert the legs 16 and 17 respectively into the pre-drilled holes 202 and 203 until the implant grip 54 resides on the first and second bones 200 and 202 between the first and second holes 202 and 203. More particularly, the surgeon pushes on the body 53 resulting in the tamp 79 of the body 53 via its contact with the bridge 8 of the implant 5 pushing on the bridge 8, which, in turn, transfers the pushing force to the legs 16 and 17 and respectively inserts the legs 16 and 17 into the pre-drilled holes 202 and 203 until the leading edge 64 of the blade 60 for the paddle 57 abuts the first and second bones 200 and 202 between the first and second holes 202 and 203.

Figure 23D:
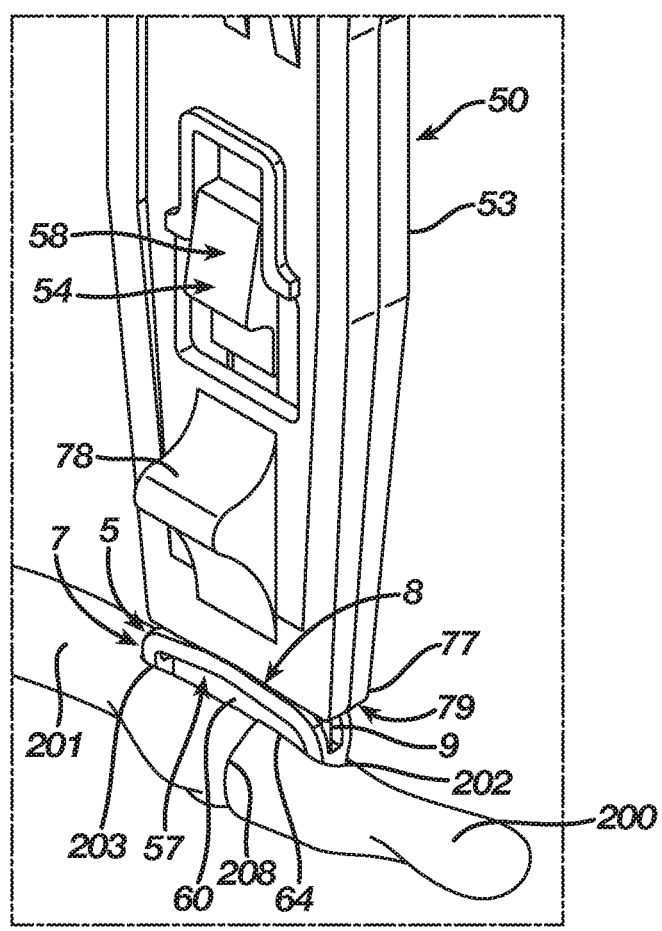
Figure 23E:
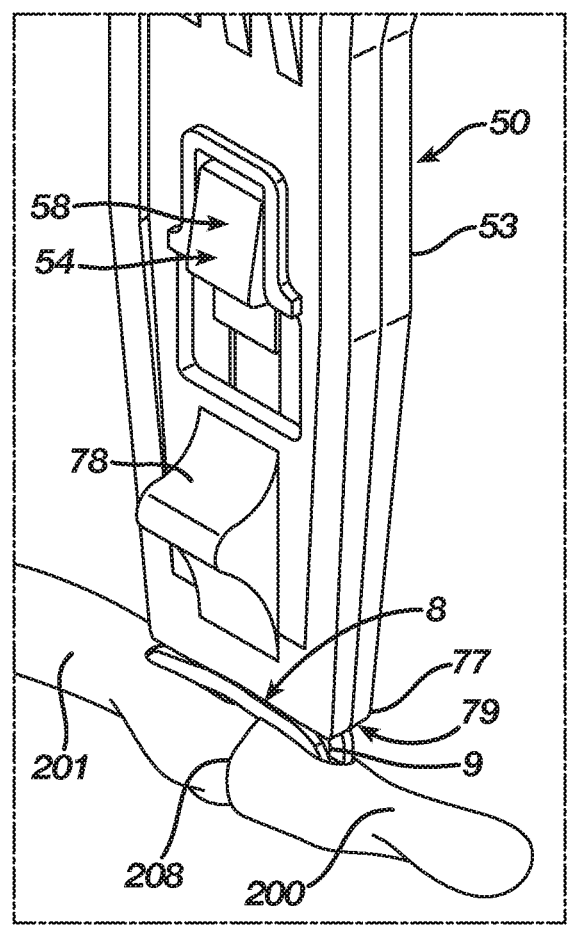
Figure 23F:
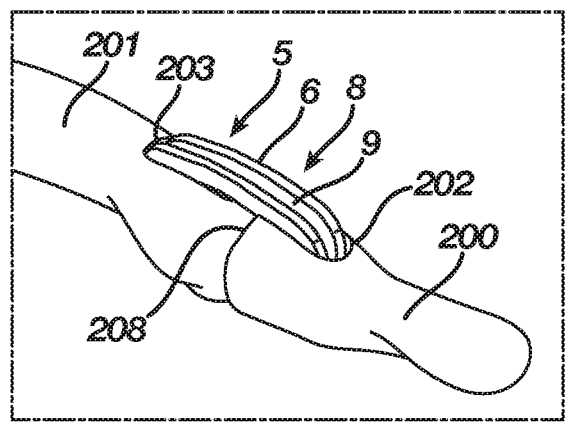

The surgeon as illustrated in FIGS. 23D and 23E continues manipulating the implant insertion device 50 to insert the legs 16 and 17 while progressing the implant grip 54 from its engaged position 56 to its disengaged position 55 thereby releasing the implant 5 from the implant insertion device 50. Progressing the implant grip 54 from its engaged position 56 to its disengaged position 55 includes: 1) the surgeon pulling the actuator 58 along the body 53 from the stop 96 to the stop 100 thereby retracting the paddle 57 into the channel 80 of the body 53 via the channel exit 83 due to the securing of the blade 60 with the actuator 58 via the shaft 59; 2) the surgeon pushing on the body 53 thereby retracting the paddle 57 into the channel 80 of the body 53 via the channel exit 83 based upon the contact of the blade 60 at its leading edge 64 with the first and second bones 200 and 201 as well as moving of the actuator 58 along the body 53 from the stop 96 to the stop 100 due to the securing of the blade 60 with the actuator 58 via the shaft 59; or 3) the surgeon pushing on the body 53 while also pulling on the actuator 58. The surgeon's pushing on the body 53 drives the legs 16 and 17 via the tamp 79 respectively into the pre-drilled holes 202 and 203 until the bridge 8 abuts the first and second bones 200 and 201 and resides in the first and second grooves 204 and 205 if formed by the surgeon. Concurrently with the insertion of the legs 16 and 17 respectively into the first and second holes 202 and 203, the paddle 57 retracts into the channel 80 of the body 53 via the channel exit 83 such that the blade 60 of the paddle 57 at its first and second ends 65 and 66 releases the bridge 8 at respective ends 9*a* and 9*b* of the slot 9. In particular with respect to the implant 5, the blade 60 at its first and second ends 65 and 66 sequentially releases the legs 16 and 17, the bridge 8 where the bridge 8 adjoins the legs 16 and 17, and the bridge 8 at respective ends 9*a* and 9*b* of the slot 9. While an insertion of the implant 5 typically includes pre-drilling of the holes 202 and 203, the surgeon may use the implant insertion device 50 to impact the legs 16 and 17 respectively into the first and second bones 200 and 201 at a desired location. Once the implant insertion device 50 implants the implant 5 into the first and second bones 200 and 201 with its bridge 8 spanning the fusion zone 208 including the implant insertion device 50 traversing to its unloaded position 51 whereby the implant grip 54 in its disengaged position 55 releases the implant 5, the implant 5 as illustrated in FIG. 23F, due to its superelastic or temperature dependent properties, delivers the energy stored in the transition sections 10 and 12 and/or the transition section 20 such that the bridge 8 attempts to transition from its insertion form to its natural form, resulting in the legs 16 and 17 attempting to move from their insertion position to their natural position whereby the implant 5 affixes the first bone 200 and the second bone 201 through an application of a compressive force to the fixation zone 208. The implant insertion device 50 accordingly does not release its constraint of the implant 5 until the legs 16 and 17 of the implant 5 fully insert respectively into the first and second holes 202 and 203 of the first and second bones 200 and 201 and the bridge 8 of the implant 5 completely seats on the first and second bones 200 and 201 such that the implant 5 does not prematurely deliver the energy stored therein to the first and second bones 200 and 201 at the fixation zone 208 thereof.

When implanting any one of the implants 105, 125, 155, and 175 utilizing the implant insertion device 50, one of ordinary skill in the art will recognize that the implant insertion device 50 operates as previously described with reference to the implantation of the implant 5 employing the implant insertion device 50 except that the number of pre-drilled holes will correspond in location, spacing, and number based upon the configuration and legs of the implants 105, 125, 155, and 175.

In view of the foregoing embodiments illustrating an implant insertion device and orthopedic implants according to the present invention, it should be understood that implant insertion devices and orthopedic implants will fall within the scope of the present invention regardless of the body shape and number of legs for an orthopedic implant. Moreover, although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system, comprising:
   an implant transitionable between a natural shape and an insertion shape, whereby the implant upon transition from the natural shape to the insertion shape stores energy, further whereby the implant upon transition from the insertion shape to the natural shape delivers the energy stored therein, the implant, comprising:
      a bridge defining a slot with a first end and a second end, and
      first and second anchoring members extending from the bridge;
   an implant insertion device movable between a loaded position whereby the implant insertion device constrains the implant in its insertion shape and an unloaded position whereby the implant insertion device releases the implant, the implant insertion device, comprising:
      a body including a first end and a second end, wherein the body defines a channel having an exit at the second end of the body, and
      an implant grip including a first end and a second end wherein the channel of the body receives the implant grip such that the implant grip couples with the body at the first end of the body, whereby the implant grip when moving from a disengaged position to an engaged position advances along the channel until the second end of the implant grip passes through the exit and exits the second end of the body such that the second end of the implant grip passes through the slot of the bridge and abuts the bridge at the first and second ends of the slot thereby constraining the implant in its insertion shape, further whereby the implant grip when moving from the engaged position to the disengaged position retracts the second end of the implant grip through the exit at the second end of the body and into the channel until the implant grip exits the slot thereby releasing the implant.

2. The orthopedic fixation system according to claim 1, wherein the body defines a tamp at its second end, whereby the tamp during loading of the implant insertion device with the implant abuts the bridge of the implant such that the exit for the channel of the body aligns with the slot of the bridge for the implant, further whereby, upon advancing the implant grip from the channel, the implant grip passes through the slot of the bridge and abuts the bridge at the first and second ends of the slot thereby constraining the implant in its insertion shape.

3. The orthopedic fixation system according to claim 1, the implant grip, comprising:
   an actuator; and
   a paddle that inserts into the channel of the body, wherein the actuator connects with the paddle and secures the paddle with the body such that movement of the actuator relative to the body progresses the paddle between an engaged position whereby the paddle advances from the channel, passes through the slot of the bridge, and abuts the bridge at the first and second ends of the slot thereby constraining the implant in its insertion shape and a disengaged position whereby the paddle retracts into the channel to release the implant.

4. The orthopedic fixation system according to claim 3, wherein the body defines a tamp at its second end, whereby the tamp during loading of the implant insertion device with the implant abuts the bridge of the implant such that the exit for the channel of the body aligns with the slot of the bridge for the implant, further whereby, upon advancing the implant grip from the channel, the implant grip passes through the slot of the bridge and abuts the bridge at the first and second ends of the slot thereby constraining the implant in its insertion shape.

5. The orthopedic fixation system according to claim 3, wherein the body defines a stop whereby, in progressing the paddle from its disengaged position to its engaged position, the actuator moves along the body towards the stop of the body until the actuator contacts the stop.

6. The orthopedic fixation system according to claim 3, wherein:
   the channel communicates exterior to the body; and
   the paddle, comprises:
      a shaft with a first end and a second end whereby, when the paddle inserts into the channel of the body, the shaft at its first end is exposed exterior to the body such that the shaft is engageable with the actuator, and a blade coupled with the shaft at its second end, the blade including a leading edge between first and second sides, wherein movement of the actuator relative to the body progresses the paddle between an engaged position whereby the blade beginning at its leading edge advances from the channel and passes through the slot of the bridge to engage the bridge with the first and second sides of the blade abutting respective first and second ends of the slot thereby constraining the implant in its insertion shape and a disengaged position whereby the blade retracts into the channel to release the implant.

7. The orthopedic fixation system according to claim 6, wherein the channel comprises a shaft channel configured to receive the shaft of the paddle therein and a blade channel configured to receive the blade of the paddle therein.

8. The orthopedic fixation system according to claim 1, wherein the bridge comprises a first bridge segment and a second bridge segment that define the slot therebetween.

9. The orthopedic fixation system according to claim 1, wherein the bridge includes a first transition section at a first end thereof and a second transition section at a second end thereof whereby the first and second transition sections deform to transition the implant between its natural shape and its insertion shape further whereby the implant grip inserts through the slot of the bridge and engages the bridge at the first and second transition sections such that the implant grip constrains the implant in its insertion shape.

10. The orthopedic fixation system according to claim 9, wherein the first anchoring member extends from the first transition section of the bridge and the second anchoring member extends from the second transition section of the bridge whereby the implant grip inserts through the slot of the bridge and engages the first and second anchoring members such that the implant grip constrains the implant in its insertion shape.

11. The orthopedic fixation system according to claim 1, wherein the bridge includes a transition section at a center section of the implant whereby the transition section deforms to transition the implant between its natural shape and its insertion shape.

12. The orthopedic fixation system according to claim 11, wherein the implant grip inserts through the slot of the bridge and engages the first and second anchoring members such that the implant grip constrains the implant in its insertion shape.

13. The orthopedic fixation system according to claim 12, wherein a third anchoring member exterior to the first anchoring member extends from the bridge at the first end thereof and a fourth anchoring member exterior to the second anchoring member extends from the bridge at the second end thereof.

14. The orthopedic fixation system according to claim 12, wherein:
the first anchoring member extends from the bridge at the first end thereof;
the second anchoring member extends from the bridge at the second end thereof;
a third anchoring member including a passage extends from the bridge interior to the first anchoring member;
a fourth anchoring member including a passage extends from the bridge interior to the second anchoring member; and
the implant grip inserts through the slot of the bridge and the passages of the third and fourth anchoring members whereby the implant grip engages the first and second anchoring members such that the implant grip constrains the implant in its insertion shape.

15. The orthopedic fixation system according to claim 11, wherein:
the first anchoring member extends from the bridge at the first end thereof offset from the first end of the slot;
the second anchoring member adjacent the first anchoring member extends from the bridge at the first end thereof offset from the first end of the slot; and
a third anchoring member extends from the bridge at the second end thereof adjacent the second end of the slot.

16. The orthopedic fixation system according to claim 11, wherein:
the first anchoring member extends from the bridge at the first end thereof offset from the first end of the slot;
the second anchoring member adjacent the first anchoring member extends from the bridge at the first end thereof offset from the first end of the slot; and
a third anchoring member extends from the bridge at the second end thereof offset from the second end of the slot; and
a fourth anchoring member adjacent the third anchoring member extends from the bridge at the second end thereof offset from the second end of the slot.

* * * * *